(12) United States Patent
Quaid et al.

(10) Patent No.: US 9,775,681 B2
(45) Date of Patent: Oct. 3, 2017

(54) HAPTIC GUIDANCE SYSTEM AND METHOD

(75) Inventors: Arthur Quaid, North Miami, FL (US);
Hyosig Kang, Weston, FL (US);
Dennis Moses, Hollywood, FL (US);
Rony Abovitz, Hollywood, FL (US);
Scott Illsley, Waterloo (CA)

(73) Assignee: MAKO Surgical Corp., Fort Lauderdale, FL (US)

( * ) Notice: Subject to any disclaimer, the term of this patent is extended or adjusted under 35 U.S.C. 154(b) by 0 days.

(21) Appl. No.: 13/195,733

(22) Filed: Aug. 1, 2011

(65) Prior Publication Data

US 2012/0109150 A1 May 3, 2012

Related U.S. Application Data

(63) Continuation of application No. 11/357,197, filed on Feb. 21, 2006, now Pat. No. 8,010,180, which is a
(Continued)

(51) Int. Cl.
*A61B 34/30* (2016.01)
*A61B 90/00* (2016.01)
(Continued)

(52) U.S. Cl.
CPC .......... *A61B 34/30* (2016.02); *A61B 17/1675* (2013.01); *A61B 17/1695* (2013.01);
(Continued)

(58) Field of Classification Search
CPC .... A61N 1/0534; A61N 1/3605; A61N 1/372; A61F 2/30942; A61F 2002/4632;
(Continued)

(56) References Cited

U.S. PATENT DOCUMENTS

| 4,747,393 A | 5/1988 | Medwid |
| 4,903,536 A | 2/1990 | Salisbury et al. |

(Continued)

FOREIGN PATENT DOCUMENTS

| EP | 1 059 067 A1 | 12/2000 |
| EP | 1 184 684 A2 | 3/2002 |

(Continued)

OTHER PUBLICATIONS

Acosta, et al., "Development of a Haptic Virtual Environment", Computer-Based Medical Systems, Proceedings 12th IEEE Symposium. pp. 35-39, 1999.
(Continued)

*Primary Examiner* — Long V Le
*Assistant Examiner* — Angela M Hoffa
(74) *Attorney, Agent, or Firm* — Foley & Lardner LLP

(57) ABSTRACT

A surgical apparatus includes a surgical device, configured to be manipulated by a user to perform a procedure on a patient, and a computer system. The computer system is programmed to implement control parameters for controlling the surgical device to provide at least one of haptic guidance to the user and a limit on user manipulation of the surgical device, based on a relationship between an anatomy of the patient and at least one of a position, an orientation, a velocity, and an acceleration of a portion of the surgical device, and to adjust the control parameters in response to movement of the anatomy during the procedure.

21 Claims, 56 Drawing Sheets

Related U.S. Application Data continuation-in-part of application No. 10/621,119, filed on Jul. 16, 2003, now Pat. No. 7,831,292, which is a continuation-in-part of application No. 10/384,078, filed on Mar. 6, 2003, now Pat. No. 8,095,200, which is a continuation-in-part of application No. 10/384,077, filed on Mar. 6, 2003, now Pat. No. 7,206,627, which is a continuation-in-part of application No. 10/384,072, filed on Mar. 6, 2003, now Pat. No. 7,206,626, which is a continuation-in-part of application No. 10/384,194, filed on Mar. 6, 2003, now Pat. No. 7,747,311.

(60) Provisional application No. 60/655,642, filed on Feb. 22, 2005, provisional application No. 60/759,186, filed on Jan. 17, 2006, provisional application No. 60/362,368, filed on Mar. 6, 2002.

(51) Int. Cl.

| | |
|---|---|
| *A61F 2/30* | (2006.01) |
| *G06F 3/01* | (2006.01) |
| *A61B 17/16* | (2006.01) |
| *A61B 34/37* | (2016.01) |
| *A61B 34/35* | (2016.01) |
| *A61N 1/05* | (2006.01) |
| *A61N 1/36* | (2006.01) |
| *A61N 1/372* | (2006.01) |
| *A61F 2/46* | (2006.01) |
| *A61B 5/11* | (2006.01) |
| *A61B 17/17* | (2006.01) |
| *A61B 17/00* | (2006.01) |
| *A61F 2/38* | (2006.01) |
| *A61B 5/00* | (2006.01) |
| *A61B 34/10* | (2016.01) |
| *A61B 34/20* | (2016.01) |
| *A61B 34/00* | (2016.01) |
| *A61B 90/14* | (2016.01) |

(52) U.S. Cl.
CPC ...... *A61B 17/1703* (2013.01); *A61B 17/1764* (2013.01); *A61B 34/10* (2016.02); *A61B 34/20* (2016.02); *A61B 34/35* (2016.02); *A61B 34/37* (2016.02); *A61B 34/70* (2016.02); *A61B 34/71* (2016.02); *A61B 34/74* (2016.02); *A61B 34/76* (2016.02); *A61B 90/36* (2016.02); *A61B 90/361* (2016.02); *A61B 90/37* (2016.02); *A61F 2/30942* (2013.01); *A61N 1/0534* (2013.01); *A61N 1/3605* (2013.01); *A61N 1/372* (2013.01); *G06F 3/016* (2013.01); *A61B 5/1127* (2013.01); *A61B 5/745* (2013.01); *A61B 17/1677* (2013.01); *A61B 17/17* (2013.01); *A61B 17/1739* (2013.01); *A61B 17/1767* (2013.01); *A61B 34/25* (2016.02); *A61B 90/14* (2016.02); *A61B 2017/00115* (2013.01); *A61B 2017/00119* (2013.01); *A61B 2017/00725* (2013.01); *A61B 2034/102* (2016.02); *A61B 2034/105* (2016.02); *A61B 2034/107* (2016.02); *A61B 2034/108* (2016.02); *A61B 2034/207* (2016.02); *A61B 2034/2048* (2016.02); *A61B 2034/2051* (2016.02); *A61B 2034/2055* (2016.02); *A61B 2034/2059* (2016.02); *A61B 2034/2068* (2016.02); *A61B 2034/252* (2016.02); *A61B 2034/254* (2016.02); *A61B 2034/305* (2016.02); *A61B 2090/08021* (2016.02); *A61B 2090/365* (2016.02); *A61B 2090/3937* (2016.02); *A61B 2090/3983* (2016.02); *A61F 2/38* (2013.01); *A61F 2002/4632* (2013.01); *A61F 2002/4633* (2013.01); *G05B 2219/36432* (2013.01); *G05B 2219/39196* (2013.01); *G05B 2219/40478* (2013.01); *G05B 2219/45117* (2013.01); *G05B 2219/45171* (2013.01)

(58) Field of Classification Search
CPC .... A61F 2002/4633; A61F 2/38; G06F 3/016; A61B 2034/2051; A61B 2034/2059; A61B 2090/365; A61B 2034/252; A61B 2034/108; A61B 2034/105; A61B 2034/254; A61B 2034/207; A61B 2034/2068; A61B 2090/3983; A61B 2034/2048; A61B 2034/102; A61B 5/745; A61B 34/30; A61B 90/361; A61B 90/37; A61B 17/1695; A61B 17/1703; A61B 34/71; A61B 34/74; A61B 34/35; A61B 34/10; A61B 34/70; A61B 34/76; A61B 34/37; A61B 34/20; A61B 90/36; A61B 17/1675; A61B 17/1764; A61B 2090/3937; A61B 2017/00115; A61B 17/17; A61B 17/1677; A61B 17/1767; A61B 90/14; A61B 2090/08021; A61B 34/25; A61B 2034/305; A61B 2034/107; A61B 2034/2055; A61B 5/1127; A61B 2017/00119; A61B 2017/00725; G05B 2219/36432

See application file for complete search history.

(56) References Cited

U.S. PATENT DOCUMENTS

| | | |
|---|---|---|
| 4,979,949 A | 12/1990 | Matsen et al. |
| 5,046,375 A | 9/1991 | Salisbury et al. |
| 5,086,401 A | 2/1992 | Glassman et al. |
| 5,142,930 A | 9/1992 | Allen et al. |
| 5,154,717 A | 10/1992 | Matsen et al. |
| 5,207,114 A | 5/1993 | Salisbury et al. |
| 5,230,338 A | 7/1993 | Allen et al. |
| 5,236,432 A | 8/1993 | Matsen et al. |
| 5,299,288 A | 3/1994 | Glassman et al. |
| 5,343,385 A | 8/1994 | Joskowicz et al. |
| 5,388,480 A | 2/1995 | Townsend |
| 5,399,951 A | 3/1995 | Lavallee et al. |
| 5,402,801 A | 4/1995 | Taylor |
| 5,408,409 A | 4/1995 | Glassman et al. |
| 5,445,144 A | 8/1995 | Wodicka et al. |
| 5,445,166 A | 8/1995 | Taylor |
| 5,452,941 A | 9/1995 | Halse et al. |
| 5,551,429 A | 9/1996 | Fitzpatrick et al. |
| 5,572,999 A | 11/1996 | Funda et al. |
| 5,576,727 A | 11/1996 | Rosenberg et al. |
| 5,587,937 A | 12/1996 | Massie et al. |
| 5,611,353 A | 3/1997 | Dance et al. |
| 5,625,576 A | 4/1997 | Massie et al. |
| 5,630,431 A | 5/1997 | Taylor |
| 5,638,819 A | 6/1997 | Manwaring et al. |
| 5,676,673 A | 10/1997 | Ferre et al. |
| 5,682,886 A | 11/1997 | Delp et al. |
| 5,688,280 A | 11/1997 | Booth et al. |
| 5,694,013 A | 12/1997 | Stewart et al. |
| 5,701,140 A | 12/1997 | Rosenberg et al. |
| 5,704,791 A | 1/1998 | Gillio |
| 5,727,554 A | 3/1998 | Kalend et al. |
| 5,766,016 A | 6/1998 | Sinclair et al. |
| 5,769,640 A | 6/1998 | Jacobus et al. |
| 5,792,147 A | 8/1998 | Evans et al. |
| 5,799,055 A | 8/1998 | Peshkin et al. |
| 5,806,518 A | 9/1998 | Mittelstadt |
| 5,831,408 A | 11/1998 | Jacobus et al. |
| 5,855,553 A | 1/1999 | Tajima et al. |
| 5,871,018 A | 2/1999 | Delp et al. |

(56) References Cited

U.S. PATENT DOCUMENTS

| | | | |
|---|---|---|---|
| 5,887,121 A | 3/1999 | Funda et al. | |
| 5,888,220 A | 3/1999 | Felt et al. | |
| 5,898,599 A | 4/1999 | Massie et al. | |
| 5,928,137 A | 7/1999 | Green | |
| 5,950,629 A | 9/1999 | Taylor et al. | |
| 5,976,156 A | 11/1999 | Taylor et al. | |
| 5,978,696 A | 11/1999 | VomLehn et al. | |
| 5,980,535 A | 11/1999 | Barnett et al. | |
| 5,984,930 A | 11/1999 | Maciunas et al. | |
| 5,987,960 A | 11/1999 | Messner et al. | |
| 6,002,859 A | 12/1999 | DiGioia, III et al. | |
| 6,006,126 A | 12/1999 | Cosman | |
| 6,006,127 A | 12/1999 | Van Der Brug et al. | |
| 6,017,305 A | 1/2000 | Bonutti | |
| 6,033,415 A | 3/2000 | Mittelstadt et al. | |
| 6,084,587 A | 7/2000 | Tarr et al. | |
| 6,104,158 A | 8/2000 | Jacobus et al. | |
| 6,109,270 A | 8/2000 | Mah et al. | |
| 6,111,577 A | 8/2000 | Zilles et al. | |
| 6,113,395 A | 9/2000 | Hon | |
| 6,147,674 A | 11/2000 | Rosenberg et al. | |
| 6,161,032 A | 12/2000 | Acker | |
| 6,188,728 B1 | 2/2001 | Hurst | |
| 6,191,796 B1 | 2/2001 | Tarr | |
| 6,205,411 B1 | 3/2001 | DiGioia, III et al. | |
| 6,219,032 B1 | 4/2001 | Rosenberg et al. | |
| 6,223,100 B1 | 4/2001 | Green | |
| 6,226,566 B1 | 5/2001 | Funda et al. | |
| 6,228,089 B1 | 5/2001 | Wahrburg | |
| 6,231,526 B1 | 5/2001 | Taylor et al. | |
| 6,233,504 B1 | 5/2001 | Das et al. | |
| 6,259,806 B1 | 7/2001 | Green | |
| 6,285,902 B1 | 9/2001 | Kienzle et al. | |
| 6,288,705 B1 | 9/2001 | Rosenberg et al. | |
| 6,292,174 B1 | 9/2001 | Mallett et al. | |
| 6,300,936 B1 | 10/2001 | Braun et al. | |
| 6,322,467 B1 | 11/2001 | Hook et al. | |
| 6,322,567 B1 | 11/2001 | Mittelstadt et al. | |
| 6,325,808 B1 | 12/2001 | Bernard et al. | |
| 6,337,994 B1 | 1/2002 | Stoianovici et al. | |
| 6,366,273 B1 | 4/2002 | Rosenberg et al. | |
| 6,377,011 B1 | 4/2002 | Ben-Ur | |
| 6,377,839 B1 | 4/2002 | Kalfas et al. | |
| 6,385,475 B1 | 5/2002 | Cinquin et al. | |
| 6,385,509 B2 | 5/2002 | Das et al. | |
| 6,393,340 B2 | 5/2002 | Funda et al. | |
| 6,405,072 B1 | 6/2002 | Cosman | |
| 6,405,158 B1 | 6/2002 | Massie et al. | |
| 6,417,638 B1 | 7/2002 | Guy et al. | |
| 6,421,048 B1 | 7/2002 | Shih et al. | |
| 6,424,885 B1 | 7/2002 | Niemeyer et al. | |
| 6,430,434 B1 | 8/2002 | Mittelstadt | |
| 6,434,416 B1 | 8/2002 | Mizoguchi et al. | |
| 6,443,894 B1 | 9/2002 | Sumanaweera et al. | |
| 6,466,815 B1 | 10/2002 | Saito et al. | |
| 6,468,265 B1 | 10/2002 | Evans et al. | |
| 6,493,608 B1 | 12/2002 | Niemeyer | |
| 6,494,039 B2 | 12/2002 | Pratt et al. | |
| 6,499,488 B1 | 12/2002 | Hunter et al. | |
| 6,533,737 B1 | 3/2003 | Brosseau et al. | |
| 6,546,277 B1 | 4/2003 | Franck et al. | |
| 6,547,782 B1 | 4/2003 | Taylor | |
| 6,551,325 B2 | 4/2003 | Neubauer et al. | |
| 6,552,722 B1 | 4/2003 | Shih et al. | |
| 6,583,161 B1 | 6/2003 | Medina | |
| 6,642,686 B1 | 11/2003 | Ruch | |
| 6,665,554 B1 * | 12/2003 | Charles et al. | 600/427 |
| 6,671,651 B2 | 12/2003 | Goodwin et al. | |
| 6,674,916 B1 | 1/2004 | Deman et al. | |
| 6,676,669 B2 * | 1/2004 | Charles et al. | 606/130 |
| 6,690,964 B2 | 2/2004 | Bieger et al. | |
| 6,692,485 B1 | 2/2004 | Brock et al. | |
| 6,701,174 B1 | 3/2004 | Krause et al. | |
| 6,702,821 B2 | 3/2004 | Bonutti | |
| 6,704,694 B1 | 3/2004 | Basdogan et al. | |
| 6,711,431 B2 | 3/2004 | Sarin et al. | |
| 6,711,432 B1 | 3/2004 | Krause et al. | |
| 6,748,819 B2 | 6/2004 | Maeguchi et al. | |
| 6,750,877 B2 | 6/2004 | Rosenberg et al. | |
| 6,757,582 B2 | 6/2004 | Brisson et al. | |
| 6,764,445 B2 | 7/2004 | Ramans et al. | |
| 6,770,078 B2 | 8/2004 | Bonutti | |
| 6,778,850 B1 | 8/2004 | Adler et al. | |
| 6,785,572 B2 | 8/2004 | Yanof et al. | |
| 6,786,896 B1 | 9/2004 | Madhani et al. | |
| 6,801,801 B1 | 10/2004 | Sati | |
| 6,810,281 B2 | 10/2004 | Brock et al. | |
| 6,816,148 B2 | 11/2004 | Mallett et al. | |
| 6,831,640 B2 | 12/2004 | Shih et al. | |
| 6,845,691 B2 | 1/2005 | Hsien | |
| 6,850,794 B2 | 2/2005 | Shahidi | |
| 6,853,965 B2 | 2/2005 | Massie et al. | |
| 6,859,661 B2 | 2/2005 | Tuke | |
| 6,877,239 B2 | 4/2005 | Leitner et al. | |
| 6,894,678 B2 | 5/2005 | Rosenberg et al. | |
| 6,920,347 B2 | 7/2005 | Simon et al. | |
| 6,985,133 B1 | 1/2006 | Rodomista et al. | |
| 6,987,504 B2 | 1/2006 | Rosenberg et al. | |
| 7,001,346 B2 | 2/2006 | White | |
| 7,035,716 B2 | 4/2006 | Harris et al. | |
| 7,039,866 B1 | 5/2006 | Rosenberg et al. | |
| 7,104,996 B2 | 9/2006 | Bonutti | |
| 7,131,073 B2 | 10/2006 | Rosenberg et al. | |
| 7,168,042 B2 | 1/2007 | Braun et al. | |
| 7,199,790 B2 | 4/2007 | Rosenberg et al. | |
| 7,206,626 B2 | 4/2007 | Quaid, III | |
| 7,206,627 B2 | 4/2007 | Abovitz et al. | |
| 7,225,115 B2 * | 5/2007 | Jones | 703/7 |
| 7,491,198 B2 | 2/2009 | Kockro | |
| 7,605,800 B2 * | 10/2009 | Rosenberg | 345/156 |
| 7,625,383 B2 | 12/2009 | Charles et al. | |
| 7,660,623 B2 | 2/2010 | Hunter et al. | |
| 7,683,565 B2 * | 3/2010 | Quaid et al. | 318/568.16 |
| 7,742,804 B2 | 6/2010 | Faul | |
| 7,747,311 B2 | 6/2010 | Quaid, III | |
| 7,774,044 B2 | 8/2010 | Sauer et al. | |
| 7,831,292 B2 | 11/2010 | Quaid et al. | |
| 7,853,313 B2 | 12/2010 | Thomson | |
| 7,947,050 B2 * | 5/2011 | Lee et al. | 606/130 |
| 7,947,051 B2 * | 5/2011 | Lee et al. | 606/130 |
| 7,974,677 B2 | 7/2011 | Mire et al. | |
| 7,996,110 B2 * | 8/2011 | Lipow et al. | 700/245 |
| 8,005,571 B2 * | 8/2011 | Sutherland et al. | 700/248 |
| 8,010,180 B2 * | 8/2011 | Quaid et al. | 600/424 |
| 8,095,200 B2 | 1/2012 | Quaid, III | |
| 8,109,942 B2 | 2/2012 | Carson | |
| 8,287,522 B2 * | 10/2012 | Moses et al. | 606/1 |
| 8,391,954 B2 * | 3/2013 | Quaid, III | 600/424 |
| 8,571,628 B2 * | 10/2013 | Kang et al. | 600/407 |
| 2001/0002830 A1 | 6/2001 | Rahn et al. | |
| 2001/0005815 A1 | 6/2001 | Rosenberg et al. | |
| 2001/0034530 A1 | 10/2001 | Malackowski et al. | |
| 2001/0036245 A1 | 11/2001 | Kienzle et al. | |
| 2001/0037064 A1 | 11/2001 | Shahidi | |
| 2001/0039422 A1 | 11/2001 | Carol et al. | |
| 2001/0041838 A1 | 11/2001 | Holupka et al. | |
| 2002/0038085 A1 | 3/2002 | Immerz | |
| 2002/0082498 A1 | 6/2002 | Wendt et al. | |
| 2002/0107521 A1 | 8/2002 | Petersen et al. | |
| 2002/0108054 A1 | 8/2002 | Moore et al. | |
| 2002/0120188 A1 | 8/2002 | Brock et al. | |
| 2002/0133174 A1 | 9/2002 | Charles et al. | |
| 2003/0112281 A1 | 6/2003 | Sriram et al. | |
| 2003/0128187 A1 | 7/2003 | Strubbe | |
| 2003/0208122 A1 | 11/2003 | Melkent et al. | |
| 2003/0209096 A1 | 11/2003 | Pandey et al. | |
| 2004/0024311 A1 | 2/2004 | Quaid, III | |
| 2004/0034282 A1 | 2/2004 | Quaid et al. | |
| 2004/0034283 A1 | 2/2004 | Quaid | |
| 2004/0034302 A1 | 2/2004 | Abovitz et al. | |
| 2004/0102866 A1 | 5/2004 | Harris et al. | |
| 2004/0106916 A1 | 6/2004 | Quaid et al. | |
| 2004/0115606 A1 | 6/2004 | Davies | |
| 2004/0127788 A1 | 7/2004 | Arata | |

(56) References Cited

U.S. PATENT DOCUMENTS

| | | |
|---|---|---|
| 2004/0128026 A1 | 7/2004 | Harris et al. |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0013477 A1 | 1/2005 | Ratti et al. |
| 2005/0027397 A1* | 2/2005 | Niemeyer ............... 700/245 |
| 2005/0062738 A1 | 3/2005 | Handley et al. |
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0137599 A1 | 6/2005 | Masini |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0203536 A1 | 9/2005 | Laffargue et al. |
| 2005/0203539 A1 | 9/2005 | Grimm et al. |
| 2005/0215879 A1 | 9/2005 | Chuanggui |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0098851 A1 | 5/2006 | Shoham et al. |
| 2006/0109266 A1 | 5/2006 | Itkowitz et al. |
| 2006/0133827 A1 | 6/2006 | Becouarn et al. |
| 2006/0142657 A1 | 6/2006 | Quaid et al. |
| 2006/0293598 A1 | 12/2006 | Fraser |
| 2007/0142751 A1 | 6/2007 | Kang et al. |
| 2007/0260140 A1 | 11/2007 | Solar et al. |
| 2007/0270685 A1 | 11/2007 | Kang et al. |
| 2008/0004632 A1* | 1/2008 | Sutherland et al. ......... 606/130 |
| 2008/0004633 A1* | 1/2008 | Arata et al. ................ 606/130 |
| 2008/0010705 A1 | 1/2008 | Quaid et al. |
| 2008/0010706 A1 | 1/2008 | Moses et al. |
| 2008/0058945 A1 | 3/2008 | Hajaj et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2009/0306499 A1* | 12/2009 | Van Vorhis et al. ......... 600/426 |
| 2010/0137882 A1 | 6/2010 | Quaid, III |
| 2010/0198219 A1 | 8/2010 | McFarlin et al. |
| 2011/0082462 A1* | 4/2011 | Suarez et al. ............... 606/99 |
| 2011/0082468 A1* | 4/2011 | Hagag et al. ............... 606/130 |
| 2011/0082587 A1* | 4/2011 | Ziaei et al. ................ 700/260 |
| 2011/0213383 A1* | 9/2011 | Lee et al. .................. 606/130 |
| 2012/0109152 A1* | 5/2012 | Quaid, III .................. 606/130 |
| 2012/0176306 A1* | 7/2012 | Lightcap et al. ........... 345/156 |
| 2013/0053648 A1* | 2/2013 | Abovitz et al. ............. 600/249 |
| 2013/0096573 A1* | 4/2013 | Kang et al. ................ 606/130 |
| 2013/0096574 A1* | 4/2013 | Kang et al. ................ 606/130 |

FOREIGN PATENT DOCUMENTS

| | | |
|---|---|---|
| EP | 1 380 266 A1 | 1/2004 |
| EP | 1 574 186 | 6/2008 |
| JP | 8-215211 | 8/1996 |
| JP | 09-330016 A | 12/1997 |
| JP | 2000-279425 | 10/2000 |
| JP | 2002-102251 | 4/2002 |
| JP | 2003-053684 | 2/2003 |
| JP | 2004-513684 | 5/2004 |
| WO | WO-95/01757 A1 | 1/1995 |
| WO | WO-96/17552 A1 | 6/1996 |
| WO | WO-00/35336 A2 | 6/2000 |
| WO | WO-02/00131 A1 | 1/2002 |
| WO | WO 02/24051 | 3/2002 |
| WO | WO-02/060653 A2 | 8/2002 |
| WO | WO-02/061371 A1 | 8/2002 |
| WO | WO 02/061688 | 8/2002 |
| WO | WO 03/777101 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO-2004/070577 A1 | 8/2004 |
| WO | WO-2004/070580 A2 | 8/2004 |
| WO | WO-2004/070581 A2 | 8/2004 |
| WO | WO-2004/075987 A1 | 9/2004 |
| WO | WO 2005/044894 | 1/2005 |
| WO | WO-2005/009215 A2 | 2/2005 |
| WO | WO 2005-72629 | 8/2005 |
| WO | WO-2005/091220 A1 | 9/2005 |
| WO | WO-2005/120380 A1 | 12/2005 |
| WO | WO-2005/122916 A1 | 12/2005 |
| WO | WO-2006/004894 A2 | 1/2006 |
| WO | WO-2006/091494 A1 | 8/2006 |
| WO | WO-2007/117297 A2 | 10/2007 |

OTHER PUBLICATIONS

Advisory Action for U.S. Appl. No. 10/384,078, mail date Mar. 1, 2010, 3 pages.
Advisory Action for U.S. Appl. No. 10/384,194, mail date May 22, 2009, 3 pages.
Advisory Action for U.S. Appl. No. 10/621,119, mail date Sep. 17, 2008, 3 pages.
Advisory Action for U.S. Appl. No. 11/750,815, mail date Feb. 22, 2011, 3 pages.
Appeal Brief for U.S. Appl. No. 10/384,078, submitted Apr. 22, 2010, 42 pages.
Applicant's response to 1$^{st}$ Office Action for Chinese Application No. 200680012488.3, submitted May 14, 2010 (10 pages).
Applicant's response to 2$^{nd}$ Office Action for Chinese Application No. 200680012488.3, submitted Dec. 7, 2010 (3 pages).
Applicant's Pre-Appeal Brief Conference Request for U.S. Appl. No. 10/384,078, submitted Feb. 25, 2010, 5 pages.
Applicant's response to Final Office Action for U.S. Appl. No. 12/144,526, submitted Mar. 15, 2011.
Applicant's response to non-final Office Action for U.S. Appl. No. 12/144,507, submitted Sep. 15, 2010.
Applicant's response to non-final Office Action for U.S. Appl. No. 12/144,517, submitted Sep. 8, 2010.
Applicant's response to non-final Office Action for U.S. Appl. No. 12/144,526, submitted Jul. 29, 2010.
Applicant's response to Office Action for U.S. Appl. No. 10/384,072, submitted Aug. 21, 2006, 14 pages.
Applicant's response to Office Action for U.S. Appl. No. 10/384,077, submitted Aug. 21, 2006, 22 pages.
Applicant's response to Office Action for U.S. Appl. No. 10/384,078, submitted Apr. 25, 2008, 10 pages.
Applicant's response to Office Action for U.S. Appl. No. 10/384,078, submitted Jan. 7, 2009, 12 pages.
Applicant's response to Office Action for U.S. Appl. No. 10/384,078, submitted Jul. 8, 2009, 17 pages.
Applicant's response to Office Action for U.S. Appl. No. 10/384,078, submitted Feb. 15, 2010, 14 pages.
Applicant's response to Office Action for U.S. Appl. No. 10/384,078, submitted Oct. 19, 2010, 16 pages.
Applicant's response to Office Action for U.S. Appl. No. 10/384,078, submitted Mar. 29, 2011, 16 pages.
Applicant's response to Office Action for U.S. Appl. No. 10/384,194, submitted Nov. 18, 2008, 19 pages.
Applicant's response to Office Action for U.S. Appl. No. 10/384,194, submitted May 1, 2009, 20 pages.
Applicant's response to Office Action for U.S. Appl. No. 10/384,194, submitted Jun. 1, 2009, 20 pages.
Applicant's response to Office Action for U.S. Appl. No. 10/384,194, submitted Feb. 2, 2010, 13 pages.
Applicant's response to Office Action for U.S. Appl. No. 10/621,119, submitted Sep. 14, 2006, 23 pages.
Applicant's response to Office Action for U.S. Appl. No. 10/621,119, submitted Oct. 2, 2006, 25 pages.
Applicant's response to Office Action for U.S. Appl. No. 10/621,119, submitted Dec. 4, 2007, 19 pages.

(56) References Cited

OTHER PUBLICATIONS

Applicant's response to Office Action for U.S. Appl. No. 10/621,119, submitted Aug. 8, 2008, 24 pages.
Applicant's response to Office Action for U.S. Appl. No. 10/621,119, submitted Mar. 9, 2009, 20 pages.
Applicant's response to Office Action for U.S. Appl. No. 10/621,119, submitted Nov. 13, 2009, 19 pages.
Applicant's response to Office Action for U.S. Appl. No. 10/621,119, submitted Apr. 30, 2010, 19 pages.
Applicant's response to Office Action for U.S. Appl. No. 11/750,815, submitted Feb. 10, 2011, 12 pages.
Applicant's response to Office Action for U.S. Appl. No. 11/750,815, submitted Mar. 31, 2010, 18 pages.
Applicant's response to Office Action for U.S. Appl. No. 11/750,815, submitted Nov. 23, 2009, 2 pages.
Applicant's response to Office Action for U.S. Appl. No. 11/750,815, submitted Sep. 13, 2010, 12 pages.
Applicant's response to Office Action for U.S. Appl. No. 11/750,840, submitted May 16, 2011, 11 pages.
Applicant's response to Office Action for U.S. Appl. No. 11/750,840, submitted Oct. 21, 2010, 5 pages.
Bettini, A., et al., "Vision Assisted Control for Manipulation Using Virtual Fixtures," proceedings of the 2001 Institute of Electrical and Electronics Engineers International Conference on Intelligent Robots and Systems, Oct. 29-Nov. 3, 2001, pp. 1171-1176.
Chapter II Demand and Response to Written Opinion for PCT/US2006/005700, submitted Dec. 15, 2006 (16 pages).
Chapter II Demand and Response to Written Opinion for PCT/US2006/049216, submitted Jul. 15, 2008.
Chen et al., "Force Feedback for Surgical Simulation," Proceedings of the IEEE, New York, US, vol. 86, No. 3, Mar. 1, 1998. pp. 524-530.
Colgate, J. Edward, et al., "Cobots: Robots for Collaboration with Human Operators," proceedings of International Mechanical Engineering Congress & Exhibition, DSC-vol. 58, 1996, pp. 433-439.
The PCT Search Report dated May 8, 2008 for corresponding PCT Application No. PCT/US2006/049216 (2 pgs.).
Davies et al, "Acrobot-using Robots and Surgeons Synergistically in Knee Surgery", 1997 British Crown Copyright, 173-178.
English translation of first Office Action for related Chinese Application No. 200680012488.3, dated Jan. 15, 2010 (6 pages).
English translation of Office Action for Chinese Application No. 200480023380.5, dated Jul. 4, 2008 (5 pages).
English translation of Office Action for Chinese Application No. 200480023380.5, dated Jan. 23, 2009 (7 pages).
English translation of Office Action for Japanese Application No. 2006-520381, dated May 19, 2010 (5 pages).
English translation of Office Action for Japanese Application No. 2006-520381, dated Nov. 18, 2010 (5 pages).
Examination report for EP 04757075.9, dated Jan. 12, 2011.
Examiner Interview Summary Record for U.S. Appl. No. 10/384,078 mail dated Oct. 15, 2010, 3 pages.
Examiner Interview Summary Record for U.S. Appl. No. 11/750,815, mail date Sep. 14, 2010, 3 pages.
Fritz, et al., "Design of a Haptic Data Visualization System for People with Visual Impairments", IEEE Trans. on Rehabiliation Engineering, vol. 7, No. 3, Sep. 1999.
Ho, S.C. et al., "Robot Assisted Knee Surgery Establishing a Force Control Strategy Incorporating Active Motion Constraint," IEEE Engineering in Medicine and Biology Magazine, vol. 14, No. 3, May 1, 1995, col. 2-3, p. 293.
Ho, S.C. et al., "Robot Assisted Knee Surgery Establishing a force control strategy incorporating active motion constraint", IEEE Engineering in Medicine & Biology, May/Jun. 1995, vol. No. 3, pp. 292-300.
Hollerbach, J.M. & D. E. Johnson. Virtual Environment Rendering. To appear in *Human and Machine Haptics*, M. Cutkosky, R. Howe, K. Salisbury, and M. Srinivasan (eds.), MIT Press, 2000 (available at http://www.cs.ubc.ca/labs/spin/publications/related/hollerbach00.pdf).

International Preliminary Examination Report for PCT/US2003/007063, dated Sep. 2, 2004 (2 pages).
International Preliminary Report on Patentability for PCT/US2004/022978 including International Search Report and Written Opinion, dated Feb. 13, 2007 (6 pages).
International Preliminary Report on Patentability for PCT/US2006/005700, dated May 8, 2007 (7 pages).
International Preliminary Report on Patentability for PCT/US2006/049216, dated Sep. 10, 2008.
International Search Report and Written Opinion for PCT/US2006/005700, dated Jun. 27, 2006.
International Search Report for PCT/US2003/007063, dated Apr. 16, 2004 (7 pages).
Kanazides, Peter et al., "An Integrated System for Cementless Hip Replacement", Integrated Surgical Systems Department of Orthopedic Surgery, Sutter General Hospital, May/Jun. 1995, pp. 307-313.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "'Acrobot' capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Moore, Carl A., et al., "Cobot Implementation of 3D Virtual Surfaces," proceedings of the 2002 Institute of Electrical and Electronics Engineers International Conference on Robotics & Automation, May 2002, pp. 3242-3247.
Niki, et al., "Simple Haptic Display and Object Data Design", Proceedings of the 2000 IEEE/RSJ International Conference on Intelligent Robots and Systems, pp. 967-972, 2000.
Notice of Allowance and Examiner Interview Summary Record for U.S. Appl. No. 10/621,119, mail date Jun. 11, 2010, 9 pages.
Notice of Allowance for U.S. Appl. No. 10/384,072, mail date Dec. 21, 2006, 7 pages.
Notice of Allowance for U.S. Appl. No. 10/384,077, mail date Dec. 14, 2006, 8 pages.
Notice of Allowance for U.S. Appl. No. 10/384,194, mail date Apr. 15, 2010, 4 pages.
Notice of Appeal and Pre-Appeal Brief Request for Review filed in response to Final Office Action for U.S. Appl. No. 12/144,507, submitted Mar. 22, 2011.
Notice of Appeal and Pre-Appeal Brief Request for Review filed in response to Final Office Action for U.S. Appl. No. 12/144,517, submitted Mar. 22, 2011.
Notice of Non-Compliant or Non-Responsive Amendment for U.S. Appl. No. 10/621,119, mail date Sep. 20, 2006, 2 pages.
Office Action and English translation for Chinese Application No. 200780018181.9, dated Jun. 10, 2010 (10 pages).
Office Action for Chinese Application No. 200480023380.5, dated Jul. 4, 2008 (4 pages).
Office Action for Chinese Application No. 200480023380.5, dated Jan. 23, 2009 (5 pages).
Office Action for Japanese Application No. 2006-520381, dated May 19, 2010 (3 pages).
Office Action for Japanese Application No. 2006-520381, dated Nov. 18, 2010 (3 pages).
Office Action for U.S. Appl. No. 10/384,072, mail date May 18, 2006, 6 pages.
Office Action for U.S. Appl. No. 10/384,077, mail date Jun. 1, 2006, 8 pages.
Office Action for U.S. Appl. No. 10/384,078, mail date Apr. 9, 2009, 13 pages.
Office Action for U.S. Appl. No. 10/384,078, mail date Dec. 30, 2010, 21 pages.
Office Action for U.S. Appl. No. 10/384,078, mail date Feb. 4, 2008, 9 pages.
Office Action for U.S. Appl. No. 10/384,078, mail date Jul. 20, 2010, 12 pages.
Office Action for U.S. Appl. No. 10/384,078, mail date Nov. 25, 2009, 14 pages.

(56) References Cited

OTHER PUBLICATIONS

Office Action for U.S. Appl. No. 10/384,078, mail date Oct. 7, 2008, 8 pages.
Office Action for U.S. Appl. No. 10/384,194, mail date Jun. 18, 2008, 2010, 9 pages.
Office Action for U.S. Appl. No. 10/384,194, mail date Mar. 2, 2009, 2010, 11 pages.
Office Action for U.S. Appl. No. 10/384,194, mail date Nov. 2, 2009, 8 pages.
Office Action for U.S. Appl. No. 10/621,119, mail date Dec. 10, 2008, 10 pages.
Office Action for U.S. Appl. No. 10/621,119, mail date Feb. 3, 2010, 12 pages.
Office Action for U.S. Appl. No. 10/621,119, mail date Jun. 16, 2006, 6 pages.
Office Action for U.S. Appl. No. 10/621,119, mail date Jun. 9, 2008, 9 pages.
Office Action for U.S. Appl. No. 10/621,119, mail date Sep. 4, 2007, 8 pages.
Office Action for U.S. Appl. No. 10/621,119, mail date Sep. 29, 2009, 9 pages.
Office Action for U.S. Appl. No. 11/646,204, mail date Apr. 19, 2011, 7 pages.
Office Action for U.S. Appl. No. 11/750,815, mail date Dec. 31, 2009, 11 pages.
Office Action for U.S. Appl. No. 11/750,815, mail date Jun. 11, 2010, 10 pages.
Office Action for U.S. Appl. No. 11/750,815, mail date Nov. 4, 2010, 11 pages.
Office Action for U.S. Appl. No. 11/750,815, mail date Oct. 27, 2009, 7 pages.
Office Action for U.S. Appl. No. 11/750,840, mail date Jul. 23, 2010, 17 pages.
Office Action for U.S. Appl. No. 11/750,840, mail date Nov. 16, 2010, 10 pages.
Office Action for U.S. Appl. No. 12/144,507, mail date Jun. 17, 2010, 7 pages.
Office Action for U.S. Appl. No. 12/144,507, mail date Nov. 22, 2010, 9 pages.
Office Action for U.S. Appl. No. 12/144,517, mail date Jun. 9, 2010, 7 pages.
Office Action for U.S. Appl. No. 12/144,517, mail date Nov. 22, 2010, 8 pages.
Office Action for U.S. Appl. No. 12/144,526, mail date Apr. 29, 2010, 9 pages.
Office Action for U.S. Appl. No. 12/144,526, mail date Nov. 15, 2010, 11 pages.
Office Action with English translation for Japanese Application No. 2008-551271, dated May 18, 2011 (6 pages).
Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Patent Abstracts of Japan for JP 08-215211 from website of Japanese Patent Office (1 page).
Patent Abstracts of Japan for JP 2000-279425 and machine translation of JP 2000-279425 from website of Japanese Patent Office (29 pages).
Patent Abstracts of Japan for JP 2002-102251 and machine translation of JP 2002-102251 from website of Japanese Patent Office (10 pages).
Patent Abstracts of Japan for JP 2003-053684 from website of Japanese Patent Office (1 page).
PCT/US2006/049216, Partial Intl. Search Report, Jan. 18, 2008 (2 pgs.).
Pre-Appeal Brief Conference Request for U.S. Appl. No. 10/621,119, submitted Oct. 9, 2008, 6 pages.
Pre-Appeal Conference Decision for U.S. Appl. No. 10/384,078, mail date Mar. 15, 2010, 2 pages.
Press Release, "The Acrobot Company Wins Best Surgical Innovation Award," Acrobot Precision Surgical Systems, May 24, 2002, 1 page.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Rosenberg, "Virtual Fixtures: Perceptual Tools for Telerobotic Manipulation", 1993 IEEE, 76-82.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider, O., et al., "Synergistic Robotic Assistance to Cardiac Procedures," presented to Computer Assisted Radiology and Surgery on Jun. 23-26, 1999, 5 pages.
Second Office Action and English translation for related Chinese Application No. 200680012488.3, dated Oct. 12, 2010 (10 pages).
Sensable Technologies, Inc., "Freeform Feel the Difference", 2001, 4 pages.
Sensable Technologies, Inc., "FreeForm Modeling—Technical Features," 2003, 2 pages.
Taylor, Russell et al., "An Image-Directed Robotic System for Precise Orthopaedic Surgery", IEEE Transactions on Robotics and Automation, vol. 10, No. 3, Jun. 1994, pp. 261-275.
Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.
Taylor, Russell et al., "Robotic Joint Replacement Surgery", NSF Engineering Research Center for Computer-Integrated Surgical Systems and Technology, 2000, 2001, 2004.
Terminal Disclaimer for U.S. Appl. No. 10/384,078, submitted Mar. 30, 2011, 1 pages.
Terminal Disclaimer Review Decision for U.S. Appl. No. 10/384,078, mailed Apr. 14, 2011, 1 page.
Tognetti, Lawrence Joseph, "Actuator Design for a Passive Haptic Display," Georgia Institute of Technology, Jun. 1999, 33 pages.
World Wide Web, http://haptics.me.jhu.edu/r.sub.--hapt.html, "Haptic Interfaces and Virtual Environments," printed on Jun. 12, 2003, 2 pages.
World Wide Web, http://haptics.me.jhu.edu/r.sub.--kine.html, "Robot Design and Kinematics," printed on Jun. 12, 2003, 2 pages.
World Wide Web, http://www.acrobot.co.uk/background.html, "The Acrobot Company Limited—Background," printed on Jul. 10, 2002, 1 page.
World Wide Web, http://www.acrobot.co.uk/home.html, "The Acrobot Company Limited—Precision Surgical Systems," printed on Jul. 10, 2002, 1 page.
World Wide Web, http://www.acrobot.co.uk/meetings.html, "The Acrobot Company Limited—Meetings and Publications," printed on Jul. 10, 2002, pp. 1-3.
World Wide Web, http://www.acrobot.co.uk/products.html, "The Acrobot Company Limited—Products," printed on Jul. 10, 2002, pp. 1-6.
World Wide Web, http://www.fcs-cs.com/robotics/content/assistance.htm, "Surgical Assistance," printed on Jun. 12, 2003, 1 page.
World Wide Web, http://www.fcs-cs.com/robotics/content/design.htm, "Virtual Design, Assembly & Maintenance," printed on Jun. 12, 2003, 1 page.
World Wide Web, http://www.fcs-cs.com/robotics/content/endeffectors.htm, "End effectors," printed on Jun. 12, 2003, 1 page.
World Wide Web, http://www.fcs-cs.com/robotics/content/hapticmaster.htm, "HapticMASTER," printed on Jun. 12, 2003, 1 page.
World Wide Web, http://www.fcs-cs.com/robotics/content/reality.htm, "Virtual Reality," printed on Jun. 12, 2003, 1 page.
World Wide Web, http://www.fcs-cs.com/robotics/content/rehabilitation.htm "Rehabilitation," printed on Jun. 12, 2003, 1 page.
World Wide Web, http://www.fcs-cs.com/robotics/content/research.htm, "Research," printed on Jun. 12, 2003, 1 page.

(56) References Cited

OTHER PUBLICATIONS

World Wide Web, http://www.fcs-cs.com/robotics/content/simulation.htm, "Simulation & Training," printed on Jun. 12, 2003, 1 page.
World Wide Web, http://www.fcs-cs.com/robotics/content/software.htm, "Software," printed on Jun. 12, 2003, 1 page.
World Wide Web, http://www.merl.com/projects/surgSim99/, "Knee Arthroscopy Simulation," printed on Jun. 12, 2003, 2 pages.
Written Opinion for PCT/US2006/049216, dated May 8, 2008.
Zilles, et al., "A Constraint-Based God-object Method for Haptic Display", IEEE Proceedings, pp. 146-151, 1995.
Abovitz et al., "The Future Use of Networked Haptic Learning Information Systems in Computer-Assisted Surgery," CAOS 2001, Jul. 6-8, 2001, pp. 337-338.
Abovitz, "Digital surgery: the future of medicine and human-robot symbiotic interaction," Industrial Robot: An International Journal, Oct. 2001, vol. 28, Issue 5, pp. 401-406 (abstract only).
Abovitz, "Human-Interactive Medical Robotics," CAOS 2000, Jun. 15-17, 2000, pp. 71-72.
Abovitz, "Human-Interactive Medical Robotics," CAOS 2001, Jul. 6-8, 2001, pp. 81-82.
Bettini et al., "Vision assisted control for manipulation using virtual fixtures: Experiments at macro and micro scales," in Proc. 2002 IEEE Intl. Conf. on Robotics and Automation, (Washington, DC), May 2002.
Cobb et al., "A robotic system for TKR surgery," in Third Annual North American Program on Computer Assisted Orthopaedic Surgery, (Pittsburgh, PA), pp. 71-74, Jun. 1999.
Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.
Goswami, et al., "Complete Parameter Identification of a Robot Using Partial Pose Information," IEEE Control Systems Magazine, Oct. 1993.
Leeser et al., "Computerassisted teach and play: Novel user-friendly robot teach mode using gravity compensation and backdrivability," in Proceedings of the Robotics International/SME Fifth World Conference on Robotics Research, (Cambridge, MA), Sep. 1994.
Meggiolaro, et al., "Manipulator calibration using a single endpoint contact constraint," in 26th ASME Bienniel Mechanisms Conference, (Baltimore, MD), 2000.
Park et al., "Virtual fixtures for robotic cardiac surgery," in Proc. Medical Image Computing and Computer-Assisted Intervention, (Utrecht, Netherlands), Oct. 2001.
Quaid et al., "Haptic Information Displays for Computer-Assisted Surgery," Proceedings of the 2002 IEEE International Conference on Robotics & Automation, May 2002, pp. 2092-2097.
Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.
Roche, "Changing the way surgeons plan and execute minimally invasive unicompartmental knee surgery," Orthopaedic Product News, pp. 16-18, Jul./Aug. 2006.
Rosenberg, Virtual Fixtures: Perceptual overlays enhance operator performance in telepresence tasks. PhD thesis, Stanford University, Aug. 1994.
Townsend et al., "Teleoperator slave—WAM design methodology," Industrial Robot, vol. 26, No. 3, pp. 167-177, 1999.
T.V. Thompson II, D.E. Johnson & E. Cohen, *Direct haptic rendering of sculptured models*, Proceedings of the Symposium on Interactive 3D Graphics, pp. 167-176, 1997.
K. Salisbury & C. Tar, *Haptic rendering of surfaces defined by implicit functions*, Proceedings of the ASME Dynamic Systems and Control Division, DSC-vol. 61, pp. 61-67, 1997.
E. Colgate, M.C. Stanley & J.M. Brown, *Issues in the haptic display of tool use*, Proceedings of the IEEE/RSJ International Conference on Intelligent Robots and Systems, vol. 3, pp. 140-145, 1995.
Steines et al., Segmentation of Osteoarthritic Femoral Cartilage Using Live Wire, Proc. Intl. Soc. Mag. Reson. Med. 8, 2000, 1 page.
Bainville, et al., Concepts and Methods of Registration for Computer-Integrated Surgery, Computer Assisted Orthopedic Surgery (CAOS), 1999, Hogrefe & Huber Publishers, 22 pages.
Burghart, et al., Robot Controlled Osteotomy in Craniofacial Surgery, 1st International Workshop on Haptic Devices in Medical Applications Proceedings, Institute for Process Control and Robotics, Jun. 23, 1999, 13 pages.
Davies, B., Computer-assisted and robotics surgery, International Congress and Symposium Series No. 223, 1997, Royal Society of Medicine Press Limited, 12 pages.
Harris, et al., Experiences with Robotic Systems for Knee Surgery, CVR Med-MRCAS'97 Proceedings of the First Joint Conference on Computer Vision, Virtual Realty, and Robotics in Medicine and Medial Robotics and Computer-Assisted Surgery, Mar. 1997, Springer, 11 pages.
Communication pursuant to Article 94(3) EPC for EP Application No. 06850614.6, dated Mar. 15, 2017, 3 pages.

\* cited by examiner

81a

82a

82c

83a

83d

Data structure of a voxel bopup table

HAPTIC GUIDANCE SYSTEM AND METHOD

CROSS REFERENCE TO RELATED APPLICATIONS

This application is a continuation of U.S. patent application Ser. No. 11/357,197, filed Feb. 21, 2006, which is a continuation-in-part of U.S. patent application Ser. No. 10/384,072, filed Mar. 6, 2003 (now U.S. Pat. No. 7,206,626); U.S. patent application Ser. No. 10/384,077, filed Mar. 6, 2003 (now U.S. Pat. No. 7,206,627), U.S. patent application Ser. No. 10/384,194, filed Mar. 6, 2003 (now U.S. Pat. No. 7,747,311), and U.S. patent application Ser. No. 10/621,119, filed Jul. 16, 2003 (now U.S. Pat. No. 7,831,292), which is a continuation-in-part of U.S. patent application Ser. No. 10/384,078, filed Mar. 6, 2003, each of which claims the benefit of priority of U.S. Provisional Patent Application No. 60/362,368, filed Mar. 6, 2002, and claims the benefit of priority of U.S. Provisional Patent Application Ser. No. 60/655,642, filed Feb. 22, 2005, and U.S. Provisional Patent Application Ser. No. 60/759,186, filed Jan. 17, 2006. Each of the above-referenced applications is incorporated by reference herein in its entirety.

BACKGROUND OF THE INVENTION

Field of the Invention

The invention relates to a surgical system and, more particularly, to a surgical system and method for orthopedic joint replacement.

Description of Related Art

Minimally invasive surgery (MIS) is the performance of surgery through incisions that are considerably smaller than incisions used in traditional surgical approaches. For example, in an orthopedic application such as total knee replacement surgery, an MIS incision length may be in a range of about 4 to 6 inches whereas an incision length in traditional total knee surgery is typically in a range of about 6 to 12 inches. As a result of the smaller incision length, MIS procedures are generally less invasive than traditional surgical approaches, which minimizes trauma to soft tissue, reduces post-operative pain, promotes earlier mobilization, shortens hospital stays, and speeds rehabilitation.

One drawback of MIS is that the small incision size reduces a surgeon's ability to view and access the anatomy. For example, in minimally invasive orthopedic joint replacement, limited visibility and limited access to the joint increase the complexity of assessing proper implant position and of reshaping bone. As a result, accurate placement of implants may be more difficult. Conventional techniques for counteracting these problems include, for example, surgical navigation, positioning the leg for optimal joint exposure, and employing specially designed, downsized instrumentation and complex surgical techniques. Such techniques, however, typically require a large amount of specialized instrumentation, a lengthy training process, and a high degree of skill. Moreover, operative results for a single surgeon and among various surgeons are not sufficiently predictable, repeatable, and/or accurate. As a result, implant performance and longevity varies among patients.

In orthopedic applications, one drawback of both MIS and traditional surgical approaches is that healthy as well as diseased bone is removed when the bone is prepared to receive the implant. For example, a total knee replacement can require removal of up to ½ inch of bone on each of three compartments of the knee. One conventional solution for preserving healthy bone is to perform a partial (or unicompartmental) knee replacement where only one compartment of the knee is damaged. A unicompartmental approach involves removal of damaged or arthritic portions on only one compartment of the knee. For example, the REPICCI® unicondylar knee system typically requires removal of only about ¼ inch of bone on one compartment of the knee. The REPICCI® system employs freehand sculpting of bone with a spherical burr through a minimally invasive incision typically about 3 inches in length. The spherical burr enables cuts having rounded shapes that cannot be reproduced with a surgical saw. The freehand burring technique, however, is difficult to master and requires more artistic sculpting capability from the surgeon than techniques utilizing traditional cutting jigs or saw guides. As a result, freehand cutting requires a high degree of skill to achieve operable results that are sufficiently predictable, repeatable, and/or accurate. Moreover, the REPICCI® technique and traditional surgical approaches can not produce cuts having complex or highly curved geometries. Thus, such approaches typically require the removal of at least some healthy bone along with the diseased/damaged bone.

Another drawback of both MIS and traditional orthopedic surgical approaches is that such approaches do not enhance the surgeon's inherent surgical skill in a cooperative manner. For example, some conventional techniques for joint replacement include autonomous robotic systems to aid the surgeon. Such systems, however, typically serve primarily to enhance bone machining by performing autonomous cutting with a high speed burr or by moving a drill guide into place and holding the position of the drill guide while the surgeon inserts cutting tools through the guide. Although such systems enable precise bone resections for improved implant fit and placement, they act autonomously (rather than cooperatively with the surgeon) and thus require the surgeon to cede a degree of control to the robot. Additional drawbacks of autonomous systems include the large size of the robot, poor ergonomics, the need to rigidly clamp the bone during registration and cutting, increased incision length for adequate robot access, and limited acceptance by surgeons and regulatory agencies due to the autonomous nature of the system.

Other conventional robotic systems include robots that cooperatively interact with the surgeon. One drawback of conventional interactive robotic systems is that such systems lack the ability to adapt surgical planning and navigation in real-time to a dynamic intraoperative environment. For example, U.S. patent application Ser. No. 10/470,314 (Pub. No. US 2004/0128026), which is hereby incorporated by reference herein in its entirety, discloses an interactive robotic system programmed with a three-dimensional virtual region of constraint that is registered to a patient. The robotic system includes a three degree of freedom (3-DOF) arm having a handle that incorporates force sensors. The surgeon utilizes the handle to manipulate the arm to move the cutting tool. Moving the arm via the handle is required so that the force sensors can measure the force being applied to the handle by the surgeon. The measured force is then used in controlling motors to assist or resist movement of the cutting tool. For example, during a knee replacement operation, the femur and tibia of the patient are fixed in position relative to the robotic system. As the surgeon applies force to the handle to move the cutting tool, the interactive robotic system may apply an increasing degree of resistance to resist movement of the cutting tool as the cutting tool approaches a boundary of the virtual region of constraint. In this manner, the robotic system guides the surgeon in preparing the bone by maintaining the cutting tool within the virtual region of constraint. As with the above-described autonomous systems, however, the interactive robotic system functions primarily to enhance bone machining. The interactive robotic system also requires the relevant anatomy to be rigidly restrained and the robotic system to be fixed in a gross position and thus lacks real-time adaptability to the intraoperative scene. Moreover, the 3-DOF configuration of the arm and the requirement that the surgeon manipulate the arm using the force handle results in limited flexibility and dexterity, making the robotic system unsuitable for certain MIS applications.

In view of the foregoing, a need exists for a surgical system that can replace direct visualization in minimally invasive surgery, spare healthy bone in orthopedic joint replacement applications, enable intraoperative adaptability and surgical planning, and produce operative results that are sufficiently predictable, repeatable, and/or accurate regardless of surgical skill level. A surgical system need not necessarily meet all or any of these needs to be an advance, though a system meeting these needs would be more desirable.

SUMMARY OF THE INVENTION

An aspect of the present invention relates to a surgical apparatus. The surgical apparatus includes a computer system and a surgical device configured to be manipulated by a user to perform a procedure on a patient. The computer system is programmed to implement control parameters for controlling the surgical device to provide at least one of haptic guidance to the user and a limit on user manipulation of the surgical device, based on a relationship between an anatomy of the patient and at least one of a position, an orientation, a velocity, and an acceleration of a portion of the surgical device, and to adjust the control parameters in response to movement of the anatomy during the procedure.

Another aspect of the present invention relates to a surgical apparatus. The surgical apparatus includes a haptic device configured to be manipulated by a user to perform a procedure on a patient. The haptic device includes at least one feedback mechanism configured to supply feedback to the user manipulating the haptic device. The surgical apparatus also includes a computer system programmed to implement control parameters for controlling the at least one feedback mechanism to provide haptic guidance to the user, while the user manipulates the haptic device, based on a relationship between an anatomy of the patient and at least one of a position, an orientation, a velocity, and an acceleration of a portion of the haptic device.

Yet another aspect of the present invention relates to a surgical method. The surgical method includes creating a representation of an anatomy of a patient; associating the anatomy and a surgical device with the representation of the anatomy; manipulating the surgical device to perform a procedure on a patient by moving a portion of the surgical device in a region of the anatomy; controlling the surgical device to provide at least one of haptic guidance and a limit on manipulation of the surgical device, based on a relationship between the representation of the anatomy and at least one of a position, an orientation, a velocity, and an acceleration of a portion of the surgical device; and adjusting the representation of the anatomy in response to movement of the anatomy during the procedure.

Yet another aspect of the present invention relates to a surgical method. The surgical method includes creating a representation of an anatomy of a patient; associating the anatomy and a haptic device with the representation of the anatomy; and manipulating the haptic device to perform a procedure on a patient by moving a portion of the haptic device in a region of the anatomy, where the haptic device includes at least one feedback mechanism configured to supply feedback during manipulation. The surgical method further includes controlling the at least one feedback mechanism to provide haptic guidance, during manipulation of the haptic device, based on a relationship between the representation of the anatomy of the patient and at least one of a position, an orientation, a velocity, and an acceleration of a portion of the haptic device.

Yet another aspect of the present invention relates to a method for joint replacement. The method includes creating a representation of a first bone; creating a representation of a second bone; planning bone preparation for implanting a first implant on the first bone; preparing the first bone to receive the first implant by manipulating a surgical tool to sculpt the first bone; planning bone preparation for implanting a second implant on the second bone after preparing the first bone; and preparing the second bone to receive the second implant by manipulating the surgical tool to sculpt the second bone.

Yet another aspect of the present invention relates to a surgical planning method. The surgical planning method includes detecting a height of a cartilage surface above a bone; creating a representation of the bone and a representation of the height of the cartilage surface; and planning bone preparation for implanting an implant on the bone based at least in part on the detected height of the cartilage surface.

Yet another aspect of the present invention relates to a surgical planning method. The surgical planning method includes creating a representation of a bone of a joint; moving the joint to a first position; identifying a first point corresponding to a first location in the joint, when the joint is in the first position; moving the joint to a second position; identifying a second point corresponding to a second location in the joint, when the joint is in the second, position; and planning bone preparation for implanting an implant on the bone based at least in part on the first and second points.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION OF PREFERRED EMBODIMENTS

Figure 1:
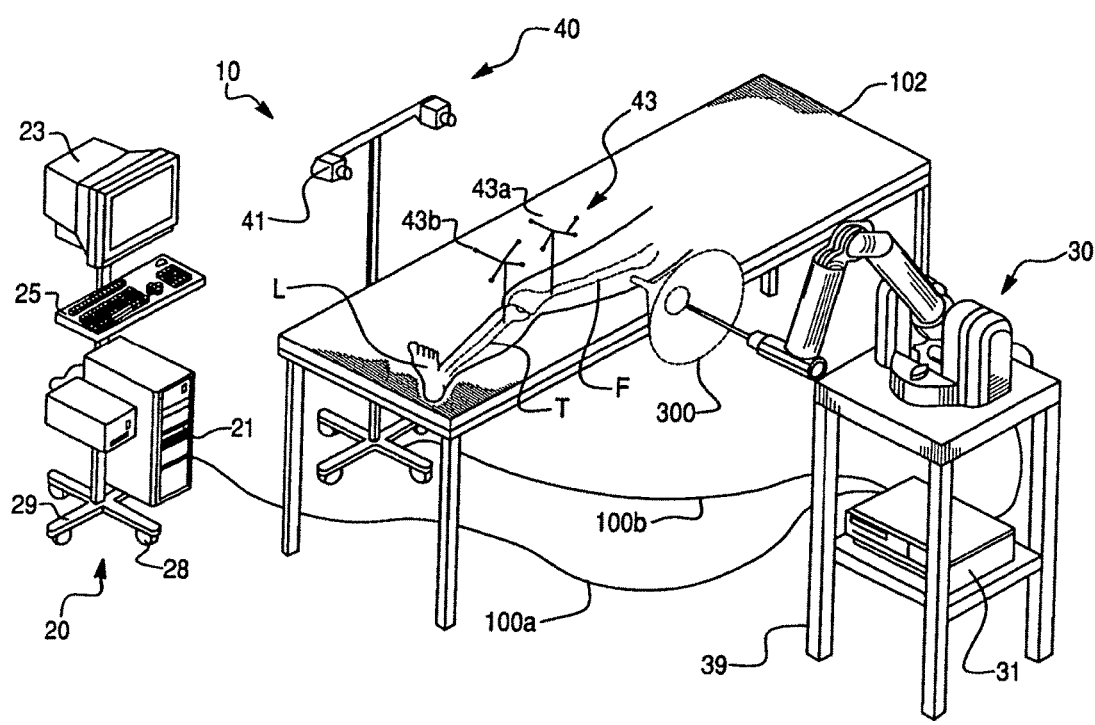
FIG. 1 is a perspective view of an embodiment of a surgical system according to the present invention.

Presently preferred embodiments of the invention are illustrated in the drawings. Although this specification refers primarily to orthopedic procedures involving the knee joint, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants.

FIG. 1 shows an embodiment of a surgical system 10 according to the present invention. The surgical system 10 includes a computing system 20, a haptic device 30, and a tracking (or localizing) system 40. In operation, the surgical system 10 enables comprehensive, intraoperative surgical planning. The surgical system 10 also provides haptic guidance to a user (e.g., a surgeon) and/or limits the user's manipulation of the haptic device 30 as the user performs a surgical procedure.

The computing system 20 includes hardware and software for operation and control of the surgical system 10. As shown in FIG. 1, the computing system 20 includes a computer 21, a display device 23, and an input device 25. The computing system 20 may also include a cart 29.

The computer 21 may be any known computing system but is preferably a programmable, processor-based system. For example, the computer 21 may include a microprocessor, a hard drive, random access memory (RAM), read only memory (ROM), input/output (I/O) circuitry, and any other well-known computer component. The computer 21 is preferably adapted for use with various types of storage devices (persistent and removable), such as, for example, a portable drive, magnetic storage (e.g., a floppy disk), solid state storage (e.g., a flash memory card), optical storage (e.g., a compact disc or CD), and/or network/Internet storage. The computer 21 may comprise one or more computers, including, for example, a personal computer (e.g., an IBM-PC compatible computer) or a workstation (e.g., a SUN or Silicon Graphics workstation) operating under a Windows, MS-DOS, UNIX, or other suitable operating system and preferably includes a graphical user interface (GUI). In one embodiment, the computer 21 includes a Navigation Module available from MAKO SURGICAL CORP.™ and identified by product number 0040TAS00001.

The display device 23 is a visual interface between the computing system 20 and the user. The display device 23 is connected to the computer 21 and may be any device suitable for displaying text, images, graphics, and/or other visual output. For example, the display device 23 may include a standard display screen (e.g., LCD, CRT, plasma, etc.), a touch screen, a wearable display (e.g., eyewear such as glasses or goggles), a projection display, a head-mounted display, a holographic display, and/or any other visual output device. The display device 23 may be disposed on or near the computer 21 (e.g., on the cart 29 as shown in FIG. 1) or may be remote from the computer 21 (e.g., mounted on a wall of an operating room or other location suitable for viewing by the user). The display device 23 is preferably adjustable so that the user can position/reposition the display device 23 as needed during a surgical procedure. For example, the display device 23 may be disposed on an adjustable arm (not shown) that is connected to the cart 29 or to any other location well-suited for ease of viewing by the user. The display device 23 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), digital or video images, registration information, calibration information, patient data, user data, measurement data, software menus, selection buttons, status information, and the like.

In addition to the display device 23, the computing system 20 may include an acoustic device (not shown) for providing audible feedback to the user. The acoustic device is connected to the computer 21 and may be any known device for producing sound. For example, the acoustic device may comprise speakers and a sound card, a motherboard with integrated audio support, and/or an external sound controller. In operation, the acoustic device may be adapted to convey information to the user. For example, the computer 21 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a beep to indicate that a surgical cutting tool is nearing a critical portion of soft tissue.

The input device 25 of the computing system 20 enables the user to communicate with the surgical system 10. The input device 25 is connected to the computer 21 and may include any device enabling a user to provide input to a computer. For example, the input device 25 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick.

The computing system 20 (in whole or in part) may be disposed on the cart 29 to economize space, minimize a physical footprint of the computing system 20, and/or permit portability. The cart 29 may be, for example, a known cart, platform, or equipment stand and is preferably configured for ease of mobility of the computing system 20. For example, as shown in FIG. 1, the cart 29 may include rolling members 28 (e.g., wheels or casters) to enable the cart 29 to be moved. The cart 29 may also include a mechanism for securing the cart 29 in position. For example, the cart 29 may be equipped with wheel locks or brakes for the rolling members 28, a foot pedal locking device, jack stands, and/or any other known mechanism for securing a cart in position. In this manner, the cart 29 enables the computing system 20 to be moved from one location to another, positioned as necessary for each surgical case, and secured in a desired position during storage and surgery. Alternatively, the computing system 20 (in whole or in part) may be installed in a room where a surgical procedure will be performed (e.g., mounted on a wall or workstation), installed in a remote location, integrated with the haptic device 30, integrated with an imaging device (e.g., a computed tomography (CT) device, a magnetic resonance imaging (MRI) device, a fluoroscopic device, an ultrasound device, etc.), and/or integrated with an medical system (e.g., a medical equipment cart in a room where a surgical procedure will be performed).

The computing system 20 is adapted to enable the surgical system 10 to perform various functions related to surgical planning, navigation, image guidance, and/or haptic guidance. For example, the computer 21 may include algorithms, programming, and software utilities related to general operation, data storage and retrieval, computer aided surgery (CAS), applications, haptic control, and/or any other suitable functionality. In one embodiment, the computing system 20 includes software used in a Navigation Module currently available from MAKO SURGICAL CORP.™ and identified by product number 0040TAS00001.

Utilities related to general operation are configured to provide basic computing functions that enable and support overall operation of the surgical system 10. General operation utilities may include, for example, well known features such as functions for fast graphics processing, functions for supporting input/output (I/O) devices, functions for connecting to a hospital network, functions for managing database libraries (e.g., implant and instrument databases), functions for system security (e.g., login features, access restrictions, etc.), and/or any other functionality useful for supporting overall operation of the surgical system 10.

Utilities related to data storage and retrieval are configured to enable storage of and access to various forms of data, such as image data (e.g., two- or three-dimensional image data sets obtained using any suitable imaging modality, such as, for example, x-ray, computed tomography (CT), magnetic resonance (MR), positron emission tomography (PET), single photon emission computed tomography (SPECT), ultrasound, etc.), application data, implant data, instrument data, anatomical model data, patient data, user preference data, and the like. The data storage and retrieval utilities may include any functionality appropriate for storing and handling relevant data.

Utilities related to computer aided surgery are configured to enable surgical planning, navigation, and basic image guided surgery capabilities. For example, as is well known, the CAS utilities may include functions for generating and displaying images from image data sets, functions for determining a position of a tip and an orientation of an axis of a surgical instrument, and functions for registering a patient and an image data set to a coordinate frame of the tracking system 40. These functions enable, for example, the computing system 20 to display on the display device 23 a virtual representation of a tracked surgical instrument overlaid on one or more images of a patient's anatomy and to update the virtual representation of the tracked instrument in real time during a surgical procedure. Images generated from the image data set may be two-dimensional or, in the case of a three-dimensional image data set, a three-dimensional reconstruction based, for example, on segmentation of the image data set. When more than one image is shown on the display device 23, the computing system 20 preferably coordinates the representation of the tracked instrument among the different images. In addition to or in lieu of images generated from image data sets, the computing system 20 may use anatomical models (e.g., based on CAD models, line art, sketches, cartoons, artist renderings, generic or morphed data sets, etc.).

Utilities related to applications of the surgical system 10 include application specific programs configured to assist the user with surgical planning and navigation. Programs associated with the application utilities may be configured for use in various medical procedures and/or may be customized for a specific procedure. For example, the application utilities may include programs related to one or more orthopedic procedures, such as, for example, total knee replacement, partial knee replacement, hip replacement, shoulder replacement, elbow replacement, wrist replacement, ankle replacement, spinal surgery, and/or installation of orthopedic and/or musculoskeletal implants, including implants of conventional materials and more exotic implants, such as orthobiologics, drug delivery implants, and cell delivery implants. The application utilities may be directed to various aspects of surgical planning and navigation, including pre-operative, intra-operative, and post-operative activities. For example, the application utilities may include programs or processes directed to planning and set up, such as, for example, system initialization processes, planning processes, visualization processes, diagnostic imaging processes, registration processes, and calibration processes. The application utilities may also include programs or processes directed to object tracking and system control, such as, for example, coordinate transform processes, interpolation processes, tool and power control processes, anatomy positioning processes, mode control processes, safety processes, occlusion detection algorithms, and forward kinematics algorithms. The application utilities may include programs or processes related to the haptic device 30, such as, for example, haptic force computation processes, haptic force mapping processes, processes for generating haptic objects, and haptic rendering algorithms. The application utilities may also include programs and processes for communicating with the user during a surgical procedure, such as, for example, software for displaying pages or images corresponding to specific steps of a surgical procedure, software for prompting a user to perform a certain task, and software for providing feedback (e.g., visual, audible, tactile, and/or force feedback) to the user.

Utilities related to haptic control are configured to perform various functions related to control, performance, stability, and/or safety of the haptic device 30. For example, the haptic control utilities may include a real time operating system (RTOS), motion control software, hardware and software for generating high frequency updates for control of the haptic device 30, software for ensuring failsafe operation of the haptic device 30 (e.g., control of brakes, monitoring of redundant sensors, etc.), and/or any other utility suitable for improving or promoting performance, stability, and/or safety of the haptic device 30. The haptic control utilities may be executed on the computer 21 of the computing system 20 provided the computer 21 has a computing architecture sufficient to support the operating requirements of the haptic control utilities. For example, processes associated with haptic control typically have higher operational frequency requirements that other processes running on the computer 21. In one embodiment, the haptic control processes operate at a frequency of approximately 2 kHz. In another embodiment, the haptic control processes operate at a frequency in a range of between about 0.1 kHz to about 10 kHz. In yet another embodiment, the haptic control processes operate at a frequency in a range of between about 500 Hz to about 2,400 Hz. In contrast, the computer 21 may operate at a substantially lower frequency, such as, for example, a frequency in a range of about 15 Hz to about 20 Hz. In another embodiment, the frequency of the computer 21 may be in a range of between about 2 Hz to about 60 Hz. In other embodiments, the frequency of the computer 21 may be substantially equivalent to the operating frequency required by the haptic control processes (e.g., approximately 2 kHz). If the computer 21 does not have an architecture sufficient to support operation of the haptic control processes, the computing system 20 may include a computer 31 for execution of the haptic control utilities. In a preferred embodiment, the computer 31 is integrated or embedded with the haptic device 30.

The computer 31 (shown in FIG. 1) may be similar to the computer 21 but is preferably configured to satisfy specific operational requirements of the haptic device 30, such as, for example, the need for higher operating frequencies. The computer 31 may comprise one or more computers. In one embodiment, the computer 31 is an Intel compatible x86 3U CompactPCI single-board computer with a processor clock speed of at least 1.6 GHz, at least 2 GByte of non-volatile storage (e.g., hard disk drive, Compact FLASH, etc.), at least 256 MB of RAM, 400 MHz Front Side Bus or faster, at least 1 MByte of Level 2 cache memory, and a real-time operating system. One such commercially available embodiment includes the ICP-PM-1004-DG-8A computer from Inova Computers GmbH, used with the QNX 6.1 (or later) operating system from QNX Software Systems Ltd.

In addition to the haptic control utilities, the computer 31 may include programs that enable the haptic device 30 to utilize data from the tracking system 40. For example, the tracking system 40 may generate tracked object pose (e.g., position and orientation) data periodically. In one embodiment, the object pose data is generated approximately 30 times a second or 30 Hz. In other embodiments, object pose data is generated more frequently such as, for example, at approximately 500 Hz or greater. The object posed data is transferred from the tracking system 40 to the computer 31 (e.g., via an interface 100b) and may be conditioned in any conventional manner such as, for example, using a noise filter as is well known. Additionally, in embodiments where the tracking system 40 operates at a lower frequency than the haptic control processes, the object pose data may be conditioned using an interpolation filter as is well known. The interpolation filter smoothes the object pose data by populating gaps between discrete data samples to enable the object pose data to be used in the higher frequency haptic control processes. The computer 31 may also include a coordinate transform process for mapping (or transforming) coordinates in one space to those in another to achieve spatial alignment or correspondence. For example, the surgical system 10 may use the coordinate transform process to map positions of tracked objects (e.g., surgical tools, patient anatomy, etc.) into a coordinate system used by a process running on the computer 31 and/or the computer 21. As is well known, the coordinate transform process may include any suitable transformation technique, such as, for example, rigid-body transformation, non-rigid transformation, affine transformation, and the like.

One advantage of including multiple computers (e.g., the computer 21 and the computer 31) in the computing system 20 is that each computer can be independently configured. Thus, the computer 21 can be customized for surgical planning and navigation, and the computer 31 can be customized for controlling performance, stability, and/or safety of the haptic device 30. For example, the computer 31 may include a real time operating system (RTOS) to maintain dependable updates to the haptic control system and a stable operating platform for the haptic device 30. In contrast, the computer 21 may include a non-RTOS because the computing system 20 may not require the same degree of stability as the haptic device 30. Thus, the computer 21 may instead be customized to meet specific requirements of surgical navigation, such as, for example, graphics processing. Another advantage of multiple computers having separate computing architectures is that software developers with limited knowledge of haptic systems can create CAS utilities for the computer 21 that can be used in conjunction with a variety of haptic devices. Similarly, software developers with limited knowledge of CAS can create haptic utilities focused on enhancing the performance, stability, and/or safety of a particular haptic device. As an alternative to separate computers, the computing functions of the haptic device 30 and the computing system 20 may be incorporated, for example, into a single computer (e.g., the computer 21 or the computer 31), into a computing system of an imaging device (e.g., a CT device, an MRI device, a fluoroscopic device, etc.), and/or into a hospital computing system (e.g., a network system, an equipment cart in a room where the surgical procedure will be performed, etc.).

As shown in FIG. 1, the computing system 20 is coupled to the haptic device 30 via an interface 100a. The interface 100a includes a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 21 and/or the computer 31 and enables the computing system 20 to communicate with and control operation of the haptic device 30. In one embodiment, the software interface includes a utility that allows the computing system 20 to issue commands to the haptic device 30. For example, the computer 21 may send a command to the computer 31 requesting the haptic device 30 to enter a specific mode (e.g., approach mode, haptic mode, free mode, input mode, hold mode). In response, the computer 31 may be programmed to check various parameters to verify that entry into the requested mode is safe and otherwise acceptable and to either enter the haptic device 30 into the requested mode or return an appropriate error message.

The haptic device 30 is a surgical device configured to be manipulated by a user to move a surgical tool 50 to perform a procedure on a patient. During the procedure, the computing system 20 implements control parameters for controlling the haptic device 30 based, for example, on a relationship between an anatomy of the patient and a position, an orientation, a velocity, and/or an acceleration of a portion of the haptic device 30 (e.g., the surgical tool 50). In one embodiment, the haptic device 30 is controlled to provide a limit on user manipulation of the device (e.g., by limiting the user's ability to physically manipulate the haptic device 30). In another embodiment, the haptic device 30 is controlled to provide haptic guidance (i.e., tactile and/or force feedback) to the user. "Haptic" refers to a sense of touch, and the field of haptics involves research relating to human interactive devices that provide tactile and/or force feedback to an operator. Tactile feedback generally includes tactile sensations such as, for example, vibration, whereas force feedback refers to feedback in the form of force (e.g., resistance to movement) and/or torque (also known as "wrench"). Wrench includes, for example, feedback in the form of force, torque, or a combination of force and torque.

Guidance from the haptic device 30 coupled with computer aided surgery (CAS) enables a surgeon to actively and accurately control surgical actions (e.g., bone cutting) and delivery of localized therapies (e.g., in the brain). For example, the computing system 20 may be programmed to determine the control parameters based on data representative of a patient's anatomy (e.g., preoperative CT image data, ultrasound data); a virtual (or haptic) object associated with (or registered to) the anatomy; a parameter relative to the anatomy (e.g., a depth defined with respect to a portion of the anatomy); and/or the anatomy. The computing system 20 can control the haptic device 30 to generate a force, a torque, and/or vibration based on the position of the tool 50 relative to the virtual object, the parameter, and/or the anatomy. For example, the tool 50 may be constrained against penetrating a virtual boundary associated with a representation of the anatomy and/or constrained against exceeding a parameter defined with respect to the representation of the anatomy. Thus, in operation, as a surgeon manipulates the haptic device 30 to move the tool 50, virtual pathways may be used to guide the tool 50 to specific targets, virtual boundaries may be used to define cutting shapes or to prevent the tool 50 from contacting critical tissue, and predefined parameters may be used to limit travel of the tool 50 (e.g., to a predefined depth). The computing system 20 may also be programmed to adjust the control parameters in response to movement of the physical anatomy during the procedure (e.g., by monitoring detected movement of the physical anatomy and then adjusting the virtual object in response to the detected movement). In this manner, the surgical system 10 can supplement or replace direct visualization of the surgical site, enhance the surgeon's natural tactile sense and physical dexterity, and facilitate the targeting, repairing, and replacing of various structures in the body through conventionally sized portals (e.g., 12 inches or greater in length) to portals having a diameter as small as approximately 1 mm.

In orthopedic applications, for example, the haptic device 30 can be applied to the problems of inaccuracy, unpredictability, and non-repeatability in bone preparation by assisting the surgeon with proper sculpting of bone to thereby enable precise, repeatable bone resections while maintaining intimate involvement of the surgeon in the bone preparation process. Moreover, because the haptic device 30 haptically guides the surgeon in the bone cutting operation, the skill level of the surgeon is less critical. As a result, surgeons with varying degrees of skill and experience are able perform accurate, repeatable bone resections. In one embodiment, for example, a surgical tool is coupled to the haptic device 30. The surgeon can operate the tool to sculpt bone by grasping and moving the tool and/or by grasping and manipulating the haptic device 30 to move the tool. As the surgeon performs the cutting operation, the surgical system 10 tracks the location of the tool (with the tracking system 40) and, in most cases, allows the surgeon to freely move the tool in the workspace. When the tool is in proximity to a virtual boundary in registration with the patient, however, the surgical system 10 controls the haptic device 30 to provide haptic guidance that tends to constrain the surgeon from penetrating the virtual boundary with the tool. For example, the virtual boundary may be defined by a haptic object, and the haptic guidance may comprise an output wrench (i.e., force and/or torque) that is mapped to the haptic object and experienced by the surgeon as resistance to further tool movement in the direction of the virtual boundary. Thus, the surgeon may feel as if the tool has encountered a physical object, such as a wall. In this manner, the virtual boundary functions as a virtual cutting guide. Thus, the haptic device 30 communicates information to the surgeon regarding the location of the tool relative to the virtual boundary and provides physical guidance in the actual cutting process. The haptic device 30 may also be configured to limit the user's ability to manipulate the surgical tool as described, for example, in U.S. patent application Ser. No. 10/470,314 (Pub. No. US 2004/0128026), which is hereby incorporated by reference herein in its entirety.

The haptic device 30 may include a mechanical or electromechanical device adapted to transmit tactile feedback (e.g., vibration) and/or force feedback (e.g., wrench) to the user. The haptic device 30 may be robotic, non-robotic, or a combination of robotic and non-robotic systems. For example, the haptic device 30 may include a haptic device as described in U.S. patent application Ser. No. 10/384,072, filed Mar. 6, 2003, published Feb. 5, 2004; U.S. patent application Ser. No. 10/384,077, filed Mar. 6, 2003, published Feb. 19, 2004; U.S. patent application Ser. No. 10/384,078, filed Mar. 6, 2003, published Feb. 19, 2004; U.S. patent application Ser. No. 10/384,194, filed Mar. 6, 2003, published Feb. 19, 2004; U.S. patent application Ser. No. 10/621,119, filed Jul. 16, 2003, published Jun. 3, 2004; and/or U.S. Provisional Patent Application Ser. No. 60/655,642, filed Feb. 22, 2005. Each of the above-referenced published applications is hereby incorporated by reference herein in its entirety.

Figure 2A:
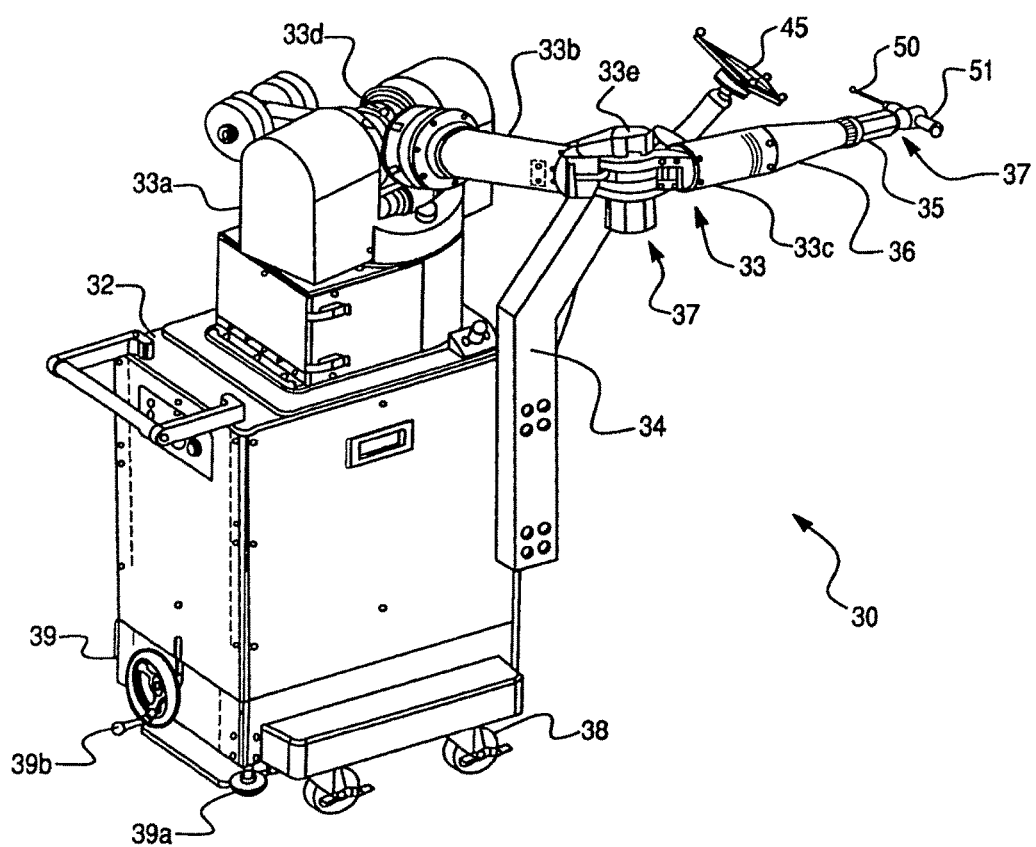
FIG. 2A is a perspective view of an embodiment of a haptic device according to the present invention.

In one embodiment, the haptic device 30 comprises a robot. In this embodiment, as shown in FIG. 2A, the haptic device 30 includes a base 32, an arm 33, an end effector 35, and a user interface 37. The haptic device 30 may also include a platform 39.

The base 32 provides a foundation for the haptic device 30. As shown in FIG. 2, the base 32 supports the arm 33 and may also house and/or support other components of the haptic device 30, such as, for example, controllers, amplifiers, actuators, motors, transmission components, clutches, brakes, power supplies, sensors, computer hardware, and/or any other well-known robotic component. The base 32 may be made of any suitable metallic and/or synthetic material, such as, for example, aluminum or plastic, and preferably includes removable panels to provide access to components housed within the base 32.

Figure 2B:
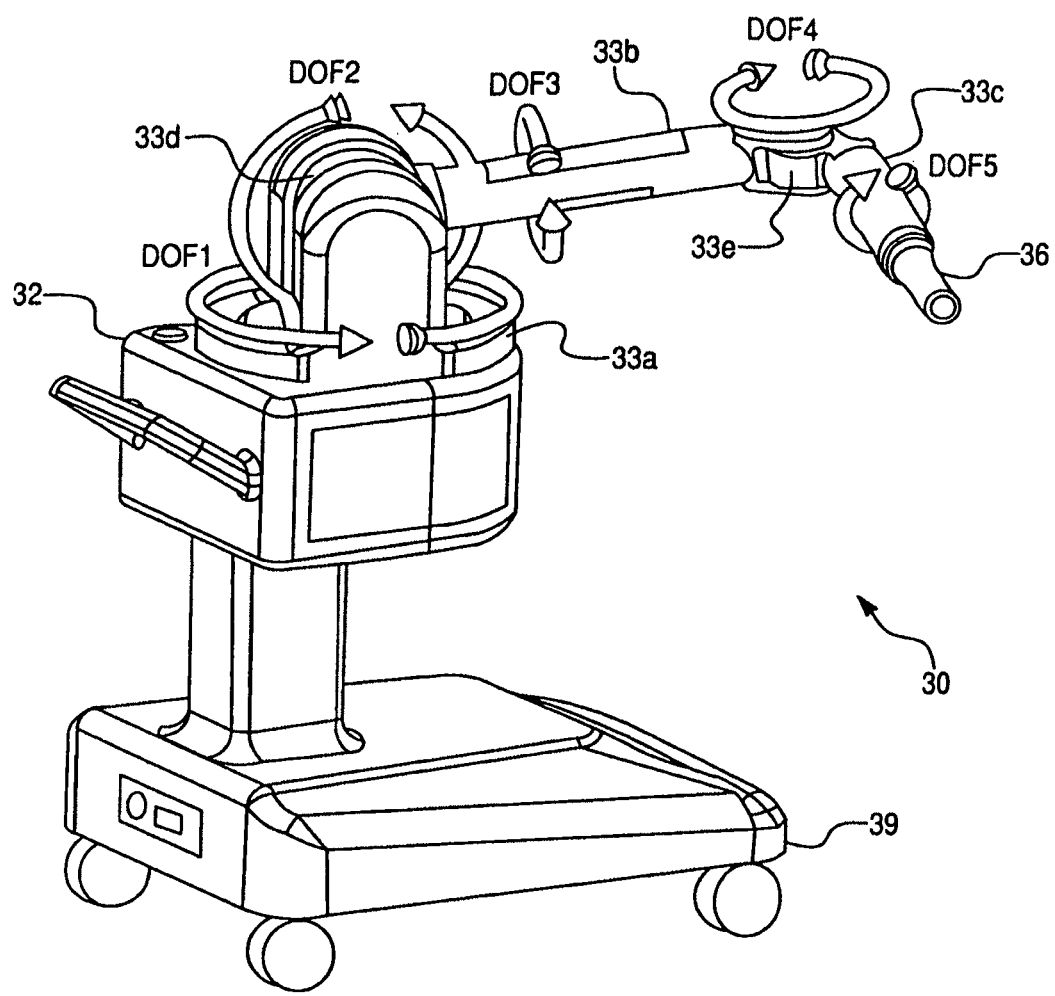
FIG. 2B is a perspective view of an embodiment of a haptic device according to the present invention.

The arm 33 is disposed on the base 32 and is adapted to enable the haptic device 30 to be manipulated by the user. The arm 33 may be any suitable mechanical or electromechanical structure but is preferably an articulated arm having four or more degrees of freedom (or axes of movement), such as, for example, a robotic arm known as the "Whole-Arm Manipulator" or WAM™ currently manufactured by Barrett Technology, Inc. In one embodiment, the arm 33 includes a first segment 33a, a second segment 33b, and a third segment 33c as shown in FIG. 2A. The first segment 33a and the second segment 33b are connected at a first joint 33d (e.g., a shoulder joint), and the second segment 33b and the third segment 33c are connected at a second joint 33e (e.g., an elbow joint). As shown in FIG. 2B, the arm 33 may have, for example, a first degree of freedom $DOF_1$, a second degree of freedom $DOF_2$, a third degree of freedom $DOF_3$, and a fourth degree of freedom $DOF_4$. Thus, the segments 33a, 33b, and 33c and the joints 33e and 33d form an articulating mechanical linkage that can be manipulated into various positions or poses. The arm 33 is sized to be appropriate for use in a variety of procedures, such as orthopedic, neurological, and/or trauma procedures, and to be sufficiently compact to enable mobility of the haptic device 30 and efficient positioning of the haptic device 30 in an operating room. For example, the arm 33 may be sized slightly larger than a human arm. In one embodiment, the arm 33 has a reach of approximately 1 m, and a diameter of the segments 33b and 33c is approximately 89 mm. The arm 33 may also be adapted to house and/or route components of the haptic device 30, such as, for example, instrumentation, power lines, motors, transmission components, controllers, actuators, amplifiers, brakes, clutches, power supplies, sensors, and/or computer hardware. For example, the segments 33a, 33b, and 33c may include internal channels and/or hollow portions within which components of the haptic device 30 may be disposed. The segments 33a, 33b, and 33c may be made of any suitable metallic and/or synthetic material, such as, for example, aluminum or plastic, and preferably include removable panels and/or access ports to enable access to components housed within the arm 33.

Dexterity of the arm 33 may be enhanced, for example, by adding additional degrees of freedom. For example, the arm 33 may include a wrist 36. As shown in FIG. 2A, the wrist 36 may be disposed on the arm 33 (e.g., at a distal end of the third segment 33c) and includes one or more degrees of freedom to augment the degrees of freedom $DOF_1$, $DOF_2$, $DOF_3$, and $DOF_4$ of the arm 33. For example, as shown in FIG. 2B, the wrist 36 may include a degree of freedom $DOF_5$. In one embodiment, the wrist 36 includes two degrees of freedom, and the degree of freedom $DOF_3$ of the arm 33 is eliminated. The wrist 36 may also be a one degree of freedom or a three degree of freedom WAM™ wrist manufactured by Barrett Technology, Inc.

The arm 33 incorporates a feedback mechanism to enable the haptic device 30 to communicate information to the user while the user manipulates the haptic device 30. In operation, the computing system 20 controls the feedback mechanism to generate and convey tactile and/or force feedback to the user to communicate, for example, information about a location of a portion of the haptic device (e.g., the tool 50) relative to a virtual object, a parameter relative to the anatomy, and/or the anatomy. The feedback mechanism is preferably configured to produce force, torque, and/or vibration. The feedback mechanism may incorporate a drive system (not shown) comprising one or more actuators (e.g., motors) and a mechanical transmission. The actuators are preferably adapted to supply force feedback opposing the user's manipulation of the haptic device 30. The actuators may include, for example, a samarium-cobalt brushless motor driven by sinusoidally-commutated current amplifier/controllers, a neodymium-iron brushless motor driven by space-vector-commutated current amplifier/controllers, and/or any other suitable motor and commutation scheme suitable for use in a robotic system. The transmission may be, for example, a tension-element drive system (e.g., a cable, steel tape, or polymeric tendon transmission), a direct drive system, and/or any other low static friction and low backlash transmission system suitable for use in a robotic system. In an exemplary embodiment, the drive system includes a high-speed cable transmission and zero backlash, low friction, cabled differentials. In one embodiment, the cable transmission may be a cable transmission used in the WAM™ robotic arm manufactured by Barrett Technology, Inc. and/or a cable transmission as described in U.S. Pat. No. 4,903,536, which is hereby incorporated by reference herein in its entirety. One advantage of a cable transmission is that the cable transmission permits most of the bulk of the arm 33 to be disposed a sufficient distance from the surgical site so that the user is not hindered or impeded by the structure or components of the arm 33 during a surgical procedure. The drive system is preferably configured for low friction, low inertia, high stiffness, large bandwidth, near-zero backlash, force fidelity, and/or backdrivability and may also be also be adapted to help maintain the arm 33 in a state where the user perceives the arm 33 as weightless. For example, in one embodiment, the arm 33 may have a configuration that is substantially balanced. Any imbalance in the arm (e.g., due gravitational effects) can be counteracted, for example, by controlling the drive system to generate forces and/or torques to correct the imbalanced condition. The motors of the drive system may also be configured to produce oscillations or vibrations so that the haptic device 30 can provide tactile feedback to the user. In addition to the drive system, the feedback mechanism may also include a vibratory device, such as an oscillator, separate from the motors for producing vibration.

The arm 33 may include position sensors (not shown) for determining a position and orientation (i.e., pose) of the arm 33. The position sensors may include any known sensor for determining or tracking a position of an object, such as, for example, encoders, resolvers, potentiometers, linear variable differential transformers (LVDTs), tilt sensors, heading (compass) sensors, gravity direction sensors (e.g., accelerometers), optical sensors (e.g., infrared, fiber optic, or laser sensors), magnetic sensors (e.g., magnetoresistive or magnetostrictive sensors), and/or acoustic sensors (e.g., ultrasound sensors). The position sensors may be disposed at any suitable location on or within the haptic device 30. For example, the position sensors may include encoders mounted on the joints 33d and 33e and/or resolvers mounted on a shaft of each motor. The pose of the arm 33 may also be tracked using any tracking system suitable for use in a surgical environment, such as, for example, an optical, magnetic, radio, or acoustic tracking system, including the tracking system 40 described below.

In addition to the position sensors, the arm 33 may include redundant sensors (not shown). The redundant sensors are similar to the position sensors and may be used to detect discrepancies and/or instability during operation of the haptic device 30. For example, differences in output of the redundant sensors and output of the position sensors may indicate a problem with the drive system and/or the position sensors. Redundant sensors can also improve accuracy in determining the pose of the arm 33 by providing data that enables a control system of the haptic device 30 to reduce or eliminate the effect of deflection in components of the drive system and/or the arm 33. The redundant sensors are particularly advantageous when the arm 33 includes a cable transmission.

Figure 2C:
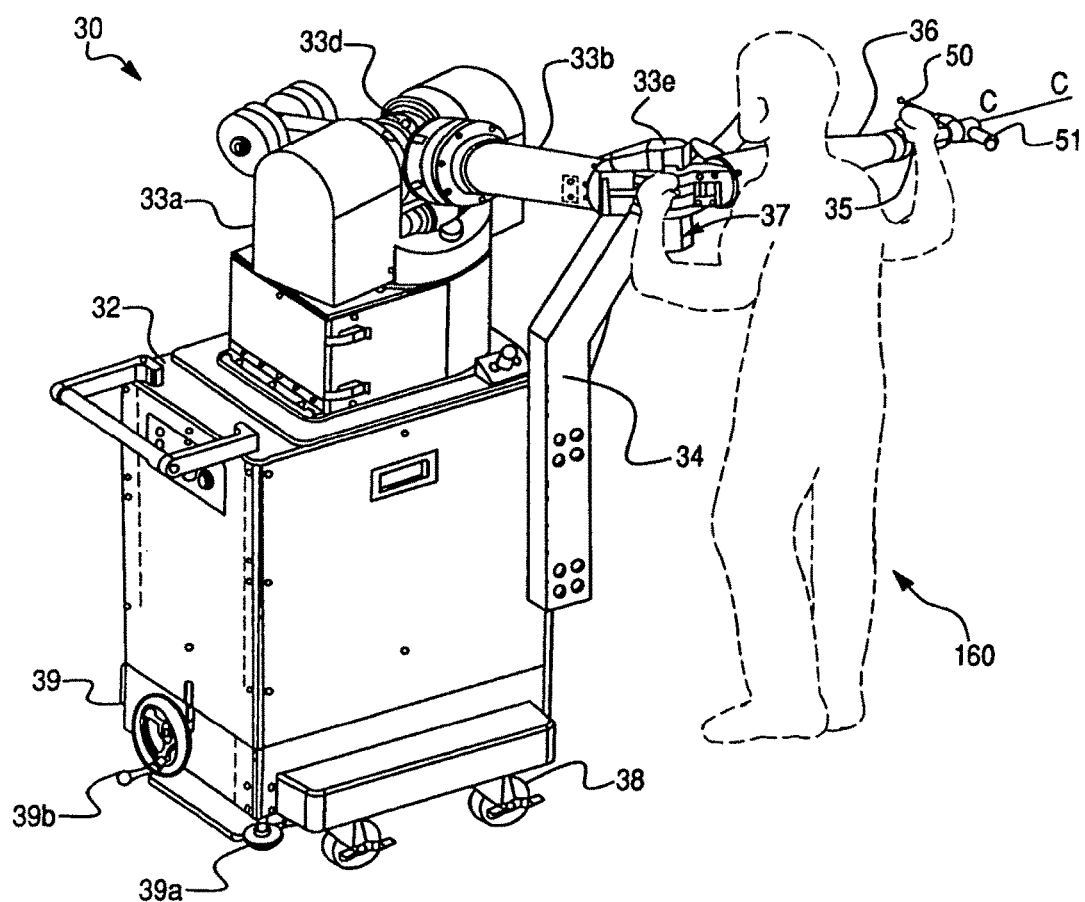
FIG. 2C is a perspective view of the haptic device of FIG. 2A showing an embodiment of a manner of operating the haptic device according to the present invention.
Figure 3:
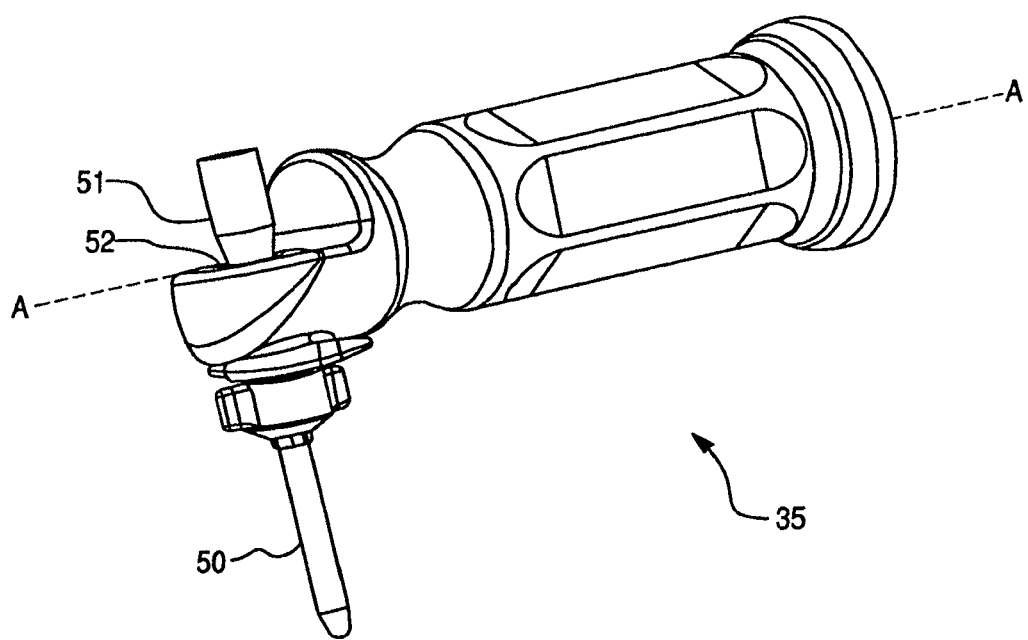
FIG. 3 is a perspective view of an embodiment of an end effector of the haptic device of FIG. 2A.

The end effector 35 comprises a working end of the haptic device 30 and is configured to enable the user to perform various activities related to a surgical procedure. For example, in one embodiment, the end effector 35 functions as an adapter or coupling between the arm 33 and the tool 50. By interchanging one tool 50 for another, the user can utilize the haptic device 30 for different activities, such as registration, bone preparation, measurement/verification, and/or implant installation. In one embodiment, as shown in FIG. 2A, the end effector 35 includes a proximal portion adapted to be connected to the arm 33 and a distal portion that includes a device or tool 50. The tool 50 may be, for example, a surgical tool (such as a burr, drill, probe, saw, etc.), medical device, microscope, laser range finder, camera, light, endoscope, ultrasound probe, irrigation device, suction device, radiotherapy device, and/or any other component useful for surgery, surgical planning, and/or surgical navigation. The end effector 35 is preferably configured to removably engage the tool 50 so that the user can install the appropriate tool 50 for a particular procedure and interchange tools as necessary. For example, the tool 50 may be secured to the end effector 35 with conventional hardware (e.g., screws, pins, clamps, etc.), a keyed connection, detents, threaded connectors, an interference fit, and the like. Alternatively, the tool 50 may be an integral part of the end effector 35 so that the entire end effector 35 is replaced when the user desires to interchange tools. The tool 50 is preferably moveable with respect to the arm 33 to enable the user to control a precise position of the tool 50. For example, the tool 50 may be rotatable about an axis C-C (shown in FIG. 2C). In one embodiment, as shown in FIG. 3, the tool 50 includes a tool holder 51 received in an aperture 52 in the distal portion of the end effector 35. The tool holder 51 may be secured in the aperture in any known manner, such as, for example, with keyed or threaded connection. The tool holder 51 is configured to releasably engage the tool 50 (e.g., a tip of a spherical burr) and may include a power line (not shown) for supplying electrical (or pneumatic) power to the tool 50. In one embodiment, the tool holder 51 includes a motor for driving the tool 50 (e.g., a burr, saw, or other power tool). The tool 50 may be a single tool or may include multiple tools. For example, the tool 50 may comprise a spherical burr for bone cutting as well as suction and irrigation lines for cleaning the surgical site during a cutting operation. In one embodiment, the tool 50 and the tool holder 51 comprise an electric, air cooled surgical tool currently manufactured by ANSPACH® and having product numbers EMAX2 (motor), EMAX2-FP (foot pedal), SC2000 (console), L-2SB (2 mm fluted ball), L-4B (4 mm fluted ball), L-6B (6 mm fluted ball), and L-1R (12) (1.2 mm×12.8 mm fluted router). The end effector 35 is mechanically and electrically connected to the distal end of the arm 33 in any conventional manner and may include one or more lines for supplying power, compressed air, suction, irrigation, and the like to the tool 50.

The end effector 35 may also be configured to enable the user to input information into the surgical system 10. For example, in one embodiment, the end effector 35 is adapted to function as an input device, such as a joystick. In this embodiment, the end effector 35 includes one or more degrees of freedom to enable joystick functionality. As shown in FIG. 3, the end effector 35 may have a single degree of freedom that permits the end effector 35 to rotate about an axis A-A. Thus, the user can rotate (or twist) the end effector 35 about the axis A-A to provide input to the surgical system 10. When the user rotates the end effector 35, a corresponding encoder signal indicating an amount and direction of rotation may be relayed to the computer 21 and/or the computer 31. For example, rotation in a first direction about the axis A-A by a specified number of degrees could indicate "forward" (e.g., proceed to another step in the procedure or to another application, advance a screen on the display device 23 to a subsequent screen, etc.), and rotation in a second direction about the axis A-A by a specified number of degrees could indicate "back" (e.g., return to a previous step in the procedure or to another application, go back to a previous screen on the display device 23, etc.). The end effector 35 (and/or other part of the arm 33) may also include additional degrees of freedom enabling additional input. In addition to joystick functionality, the end effector 35 (and/or any other portion of the haptic device 30) may include one or more buttons, dials, and/or switches to enable input. In this manner, efficiency and ease of use of the surgical system 10 is improved by providing a convenient input mechanism for the user.

The user interface 37 of the haptic device 30 enables physical interaction between the user and the haptic device 30. For example, the interface 37 may be configured so that the user can physically contact the interface 37 and manipulate the tool 50 while simultaneously receiving haptic guidance from the haptic device 30. The interface 37 may be a separate component affixed to the haptic device 30 (such as a handle or hand grip) or may simply be part of the existing structure of the haptic device 30. For example, the interface 37 may be associated with the arm 33, the end effector 35, and/or the tool 50. Because the interface 37 is affixed to or is an integral part of the haptic device 30, any tactile or force feedback output by the haptic device 30 is transmitted directly to the user when the user is in contact with the interface 37. In one embodiment, as shown in FIG. 2A, the user interface 37 comprises a first part (e.g., the elbow joint 33e of the arm 33) configured to enable the user to change a configuration of the arm 33 and a second part (e.g., the tool 50 and/or a distal end of the arm 33 such as the end effector 35) configured to enable the user to move the tool 50 relative to the arm 33. In operation, as shown in FIG. 2C, a user 160 places one hand on the first part (e.g., the elbow joint 33e) and grasps the second part (e.g., the tool 50) with the other hand. The user 160 then exerts force as needed to manipulate the arm 33 and move the tool 50. In this manner, the user manipulates the interface 37 to simultaneously change a configuration of the arm 33 and move the tool 50 relative to the arm 33. Contacting the haptic device 30 in dual locations (e.g., the tool 50 and the elbow joint 33e) advantageously allows both gross and fine control of the haptic device 30. For example, the user 160 is able to simultaneously control both a gross configuration of the arm 33 (e.g., via the elbow joint 33e) and a fine (or precise) location of a tip of the tool 50 (e.g., by moving the tool 50 relative to the arm 33), which is important in performing activities requiring a high degree of accuracy and dexterity, such as, for example, maneuvering the tool 50 to the surgical site and sculpting bone.

The user interface 37 is preferably sized so that the user can easily grip the interface 37. For example, a diameter of the interface 37 may correspond to a diameter that is easily grasped by a hand and/or finger(s) of a user. The diameter of the interface 37 may be, for example, in a range of approximately 5 mm to approximately 75 mm. In one embodiment, the user interface 37 is integral with the end effector 35. In this embodiment, the end effector 35 includes one or more portions having a diameter suitable for gripping by the user. For example, a diameter of the proximal portion of the end effector 35 may be about 43 mm; a diameter of the distal portion of the end effector 35 may be about 36 mm; a diameter of the tool holder 51 may be about 19 mm; and a diameter of the tool 50 may be about 6 mm. In one embodiment, the distal portion of the end effector 35 includes a grip for the user's index finger. The interface 37 may optionally include a taper to accommodate users with different hand sizes. The interface 37 may also be shaped or contoured to mate with the contours of a user's hand and/or finger(s) and may include other ergonomic features, for example, to increase user comfort and prevent slippage (e.g., when the user's glove is wet/bloody).

One advantage of the haptic device 30 is that the user interface 37 advantageously enables the haptic device 30 to hold the tool 50 cooperatively with the user. In contrast, haptic devices used in surgical teleoperation systems have a "slave" device that exclusively holds the tool and a "master" device through which the surgeon controls the tool. The master device is typically remote from the surgical site either to permit the surgeon to perform the surgery over a distance or to provide a more ergonomic working position/environment for the surgeon. Thus, with a haptic teleoperation system, the surgeon has the disadvantage of having to rely entirely on the teleoperation system to view the surgical site and perform the surgery. In contrast, with the surgical system 10, as user moves the tool 50 with guidance from the haptic device 30, the user remains in close physical and visual proximity to the surgical site.

Another advantage of the haptic device 30 is that the haptic device 30 is not intended to move autonomously on its own. In contrast, autonomous surgical robotic systems used for orthopedic joint replacement perform bone cutting autonomously with a high speed burr. Although the surgeon monitors progress of the robot and may interrupt if necessary, the surgeon is not in full control of the procedure. With the haptic device 30, however, the surgeon (as opposed to the robot) manipulates the tool 50. Thus, the surgeon maintains control of the cutting operation and receives only guidance or assistance from the haptic device 30. As a result, the surgeon is not required to cede control to the robot of the haptic device 30, which increases the surgeon's comfort level during the procedure.

As described above in connection with the computing system 20, the haptic device 30 may include the computer 31. The computer 31 may be housed in any convenient location on the surgical system 10, such as, for example, on or in a stand or equipment cabinet (e.g., the platform 39 as shown in FIG. 1) on which the haptic device 30 is disposed. The computer 31 may be used in addition to or as an alternative to the computer 21 of the computing system 20. The haptic device 30 (including the computer 31) may also include any other computer, electronic, or electro-mechanical component suitable for use in a robotic and/or haptic device, such as, for example, a controller for receiving information from the encoders and redundant sensors on the arm 33, amplifiers for providing power to the motors, clutches, brakes, a power supply for failsafe brakes, and/or a mode switch for placing the haptic device 30 in a desired operational mode (e.g., approach mode, haptic mode, free mode, input mode, hold mode).

The haptic device 30 is preferably sized so that the haptic device 30 can fit in an operating room without impeding other equipment or movement of the user about the operating room. For example, in one embodiment, a height of the haptic device 30 (with the arm 33 in a stored or retracted position) is approximately 1.4 m, and a footprint of the haptic device 30 is in a range of between about 0.25 m$^2$ to about 0.6 m$^2$. In another embodiment, the footprint is in a range of between about 0.09 m$^2$ and 0.13 m$^2$. Similarly, the haptic device 30 preferably has a weight that enables the haptic device 30 to be moved from one location to another with relative ease. For example, in one embodiment, the weight of the haptic device 30 is in a range of approximately 100 pounds to approximately 500 lbs. In another embodiment, the weight of the haptic device 30 is in a range of approximately 50 pounds to approximately 200 lbs. The haptic device 30 preferably has a low weight and small size both for ease of mobility and to permit the haptic device 30 to be optimally positioned for the surgical procedure. For example, the haptic device 30 (or any portion thereof) may be configured to rest on a floor of an operating room, to be mounted on the operating table (or other piece of equipment in the operating room), or to be affixed to a bone of the patient.

As shown in FIG. 1, the haptic device 30 (or a portion thereof, such as the robot) may be mounted on a platform 39. The platform 39 may be any known platform, cart, or equipment stand, may include equipment racks and/or cabinets (e.g., to house the computer 31), and is preferably configured to facilitate mobility of the haptic device 30. For example, the platform 39 may include rolling members 38 (e.g., wheels or casters) to enable the platform 39 to be moved. The platform 39 may also include a mechanism for securing the platform 39 in position. For example, the platform 39 may be equipped with wheel locks or brakes for the rolling members 38, a foot pedal locking device, jack stands, and/or any other known mechanism for securing a platform or cart in position. In one embodiment, as shown in FIG. 2A, the platform 39 includes rigid feet 39a that can be actuated between a retracted position (shown in FIG. 2A) and an extended position (not shown) with a mechanism 39b. To move the platform 39 from one location to another, the rigid feet 39a are retracted so that the platform 39 can travel on the rolling members 38. To secure the platform 39 in position, the rigid feet 39a are extended so that the platform 39 rests on the rigid feet 39a. Alternatively, the rigid feet 39a could be fixed on the platform 39, and the rolling members 38 could be extendable/retractable. Thus, the platform 39 enables the haptic device 30 to be moved from one location to another, positioned as necessary for each surgical case, and secured in a desired position during storage and surgery. Alternatively, the haptic device 30 (in whole or in part) may be installed in a room where a surgical procedure will be performed (e.g., mounted on a floor, wall, or workstation), integrated with the computing system 20, integrated with an imaging device (e.g., a CT device, a fluoroscopic device, an ultrasound device, etc.), and/or integrated with a medical system (e.g., a medical equipment cart in a room where a surgical procedure will be performed).

As shown in FIG. 1, the haptic device 30 and the computing system 20 are preferably configured as separate units. Alternatively, the haptic device 30 (in whole or in part) and the computing system 20 (in whole or in part) may be integrated into a single unit. The haptic device 30 and the computing system 20 (or portions thereof) may also be integrated with other pieces of equipment, such as, for example, an imaging device (e.g., a CT device, an MRI device, a fluoroscopic device, an ultrasound device, etc.) and/or a hospital system (e.g., an equipment cart in a room where the surgical procedure will be performed). In one embodiment, the computer 21 and the computer 31 are disposed on the platform 39 of the haptic device 30, and the display device 23 and the input device 25 of the computing system 20 are disposed on a light weight stand to facilitate the user's ability to view information from and input information to the surgical system 10.

The tracking (or localizing) system 40 of the surgical system 10 is configured to determine a pose (i.e., position and orientation) of one or more objects during a surgical procedure to detect movement of the object(s). For example, the tracking system 40 may include a detection device that obtains a pose of an object with respect to a coordinate frame of reference of the detection device. As the object moves in the coordinate frame of reference, the detection device tracks the pose of the object to detect (or enable the surgical system 10 to determine) movement of the object. As a result, the computing system 20 can adjust the control parameters (e.g., by adjusting a virtual object) in response to movement of the tracked object. Tracked objects may include, for example, tools/instruments, patient anatomy, implants/prosthetic devices, and components of the surgical system 10. Using pose data from the tracking system 40, the surgical system 10 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 21 and/or the computer 31. For example, utilizing pose data from the tracking system 40, the surgical system 10 is able to associate the physical anatomy and the tool 50 (and/or the haptic device 30) with a representation of the anatomy (such as an image displayed on the display device 23). Based on tracked object and registration data, the surgical system 10 may determine, for example, (a) a spatial relationship between the image of the anatomy and the relevant anatomy and (b) a spatial relationship between the relevant anatomy and the tool 50 so that the computing system 20 can superimpose (and continually update) a virtual representation of the tool 50 on the image, where the relationship between the virtual representation and the image is substantially identical to the relationship between the tool 50 and the actual anatomy. Additionally, by tracking not only the tool 50 but also the relevant anatomy, the surgical system 10 can compensate for movement of the relevant anatomy during the surgical procedure (e.g., by adjusting a virtual object in response to the detected movement).

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MRI images to an intraoperative scene).

The tracking system 40 may be any tracking system that enables the surgical system 10 to continually determine (or track) a pose of the relevant anatomy of the patient and a pose of the tool 50 (and/or the haptic device 30). For example, the tracking system 40 may comprise a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, the a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers. The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

In one embodiment, as shown in FIG. 1, the tracking system 40 includes a non-mechanical tracking system. In this embodiment, the non-mechanical tracking system is an optical tracking system that comprises a detection device 41 and at least one trackable element (or tracker) configured to be disposed on (or incorporated into) a tracked object and detected by the detection device 41. As shown in FIG. 1, the detection device 41 may include, for example, a stereo camera pair sensitive to infrared radiation and positionable in an operating room where the surgical procedure will be performed. The tracker is configured to be affixed to the tracked object in a secure and stable manner and includes an array of markers (e.g., an array S1 in FIG. 4) having a known geometric relationship to the tracked object. The markers may be active (e.g., light emitting diodes or LEDs) or passive (e.g., reflective spheres, a checkerboard pattern, etc.) and preferably have a unique geometry (e.g., a unique geometric arrangement of the markers) or, in the case of active, wired markers, a unique firing pattern. In operation, the detection device 41 detects positions of the markers, and the unique geometry (or firing pattern) and known geometric relationship to the tracked object enable the surgical system 10 to calculate a pose of the tracked object based on the positions of the markers.

Because the non-mechanical tracking system relies on an ability of the detection device 41 to optically "see" the markers, the detection device 41 and the tracker should be positioned so that a clear line of sight between the detection device 41 and the markers is maintained during the surgical procedure. As a safeguard, the surgical system 10 is preferably configured to alert a user if the detection device 41 is unable to detect the tracker during the procedure (e.g., when the line of sight between the detection device 41 and one or more of the markers is blocked and/or when reflectivity of the markers is occluded). For example, the surgical system 10 may include an audible (and/or visual) alarm programmed to sound (and/or flash) when a person steps between the markers and the detection device 41, when an object is interposed between the markers and the detection device 41, when a lens of the camera is occluded (e.g., by dust), and/or when reflectivity of the markers is occluded (e.g., by blood, tissue, dust, bone debris, etc.). The surgical system 10 may also include programming to trigger other safety features, such as, for example, an occlusion detection algorithm (discussed below in connection with step S11 of FIG. 13) with a power shutoff feature that disables the tool 50 when the detection device 41 loses sight of the markers.

The non-mechanical tracking system may include a trackable element (or tracker) for each object the user desires to track. For example, in one embodiment, the non-mechanical tracking system includes an anatomy tracker 43 (to track patient anatomy), a haptic device tracker 45 (to track a global or gross position of the haptic device 30), an end effector tracker 47 (to track a distal end of the haptic device 30), and an instrument tracker 49 (to track an instrument/tool held manually by the user).

Figure 4:
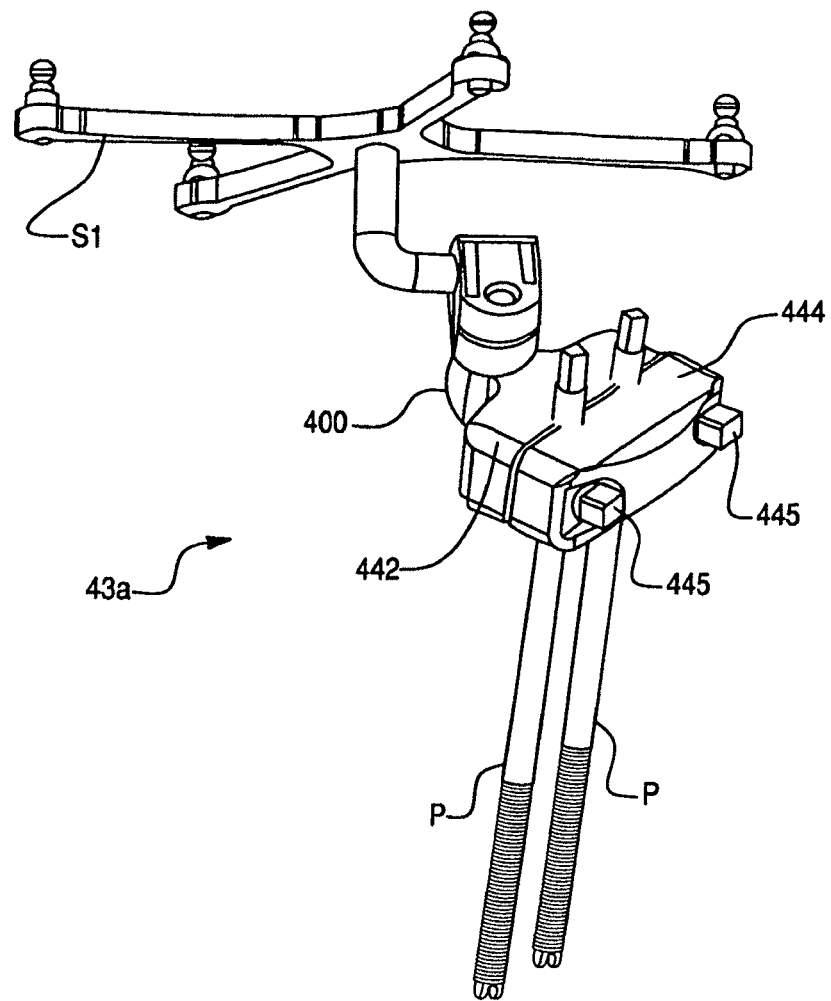
FIG. 4 is a perspective view of an embodiment of an anatomy tracker according to the present invention.

As shown in FIG. 1, the anatomy tracker 43 is disposed on a relevant portion of a patient's anatomy (such as a bone) and is adapted to enable the relevant anatomy to be tracked by the detection device 41. The anatomy tracker 43 includes a fixation device for attachment to the anatomy. The fixation device may be, for example, a bone pin, surgical staple, screw, clamp, wearable device, intramedullary rod, or the like. In one embodiment, the anatomy tracker 43 is configured for use during knee replacement surgery to track a femur F and a tibia T of a patient. In this embodiment, as shown in FIG. 1, the anatomy tracker 43 includes a first tracker 43a adapted to be disposed on the femur F and a second tracker 43b adapted to be disposed on the tibia T. As shown in FIG. 4, the first tracker 43a includes a fixation device comprising bone pins P and a unique array S1 of markers (e.g., reflective spheres). The array S1 is affixed to a connection mechanism 400 that is adapted to be removably secured to both of the bone pins P. For example, as shown in FIG. 4, the connection mechanism 400 may include a first portion 442, a second portion 444, and screws 445. To install the first tracker 43a on the femur F, the user screws the bone pins P into the femur F, slides the connection mechanism 400 over the bone pins P, and tightens the screws 445 to draw the first and second portions 442 and 444 together to thereby securely fix the connection mechanism 400 to the bone pins P. Once secured, the connection mechanism 400 imparts additional stability to the bone pins P. The second tracker 43b is identical to the first tracker 43a except the second tracker 43b is installed on the tibia T and has its own unique array of markers. When installed on the patient, the first and second trackers 43a and 43b enable the detection device 41 to track motion of the femur F and the tibia T during knee replacement surgery. As a result, the surgical system 10 is able to compensate for bone motion in real-time during surgery.

As shown in FIG. 2A, the haptic device tracker 45 is disposed on the haptic device 30 and is adapted to enable the surgical system 10 to monitor a global or gross position of the haptic device 30 in physical space. In particular, the haptic device tracker 45 enables the surgical system 10 to determine whether the haptic device 30 has moved relative to other objects in the surgical environment, such as the patient. Such information is important because the tool 50 is attached to the haptic device 30. For example, if the user intentionally repositions or inadvertently bumps the haptic device 30 while cutting the femur F with the tool 50, the tracking system 40 will detect movement of the haptic device tracker 45. In response, the surgical system 10 can make appropriate adjustments to programs running on the computer 21 and/or the computer 31 to compensate for global or gross movement of the haptic device 30 (and the attached tool 50) relative to the femur F. As a result, integrity of the femur preparation process is maintained.

Figure 5:
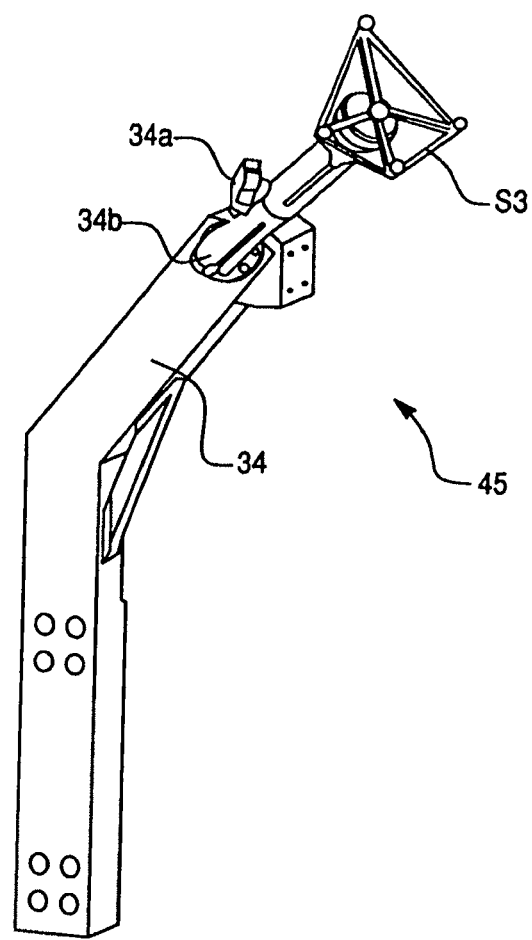
FIG. 5 is a perspective view of an embodiment of a haptic device tracker according to the present invention.

As shown in FIGS. 2A and 5, the haptic device tracker 45 includes a unique array S3 of markers (e.g., reflective spheres) and is adapted to be mounted on the base 32 of the haptic device 30. The haptic device tracker 45 is preferably mounted so that the haptic device tracker 45 can be secured in a fixed position relative to the base 32. The fixed position is calibrated to the haptic device 30 (as discussed below in connection with step S9 of FIG. 13) so that the surgical system 10 knows where the haptic device tracker 45 is located with respect to the base 32 of the haptic device 30. Once calibrated, the fixed position is maintained during the surgical procedure. In one embodiment, as shown in FIGS. 2A and 5, the haptic device tracker 45 includes an arm 34 having a proximal end connected to the base 32 (e.g., via screws, rivets, welding, clamps, magnets, etc.) and a distal end that carries the array S3 of markers. The arm 34 may include one or more support members (e.g., brackets, struts, links, etc.) having a rigid structure so that the haptic device tracker 45 is fixed in a permanent position with respect to the haptic device 30. Preferably, however, the arm 34 is adapted for adjustability so that the array S3 is moveable between a first position and a second position relative to the haptic device 30. Thus, the array S3 may be positioned independently of the base 32 of the haptic device 30 before being secured in a fixed position. One advantage of adjustability is that a position of the array S3 may be customized for each surgical case (e.g., based on patient size, operating table height, etc.). Another advantage of adjustability is that the array S3 may be positioned so as not to impede the user during a surgical procedure. Adjustability may be imparted to the arm 34 in any known manner (e.g., an articulating arm, a flexible neck, etc.). For example, in one embodiment, as shown in FIG. 5, the arm 34 includes a ball joint 34b on which the haptic device tracker 45 is disposed. The ball joint 34b includes a locking mechanism actuated by a handle 34a. In operation, the user may unscrew the handle 34a to release the ball joint 34b, manipulate the ball joint 34b until the haptic device tracker 45 is in a desired position, and tighten the handle 34a until the ball joint 34b is fixedly secured. In this manner, the haptic device tracker 45 may be fixed in the desired position. As an alternative to securing the haptic device tracker 45 in a fixed position and calibrating the fixed position to the haptic device 30, the arm 34 may include position sensors (e.g., encoders). The position sensors may be similar to the position sensors of the arm 33 and may operate in conjunction with appropriate software (e.g., software running on the computer 21 or the computer 31) to provide measurements of a pose of the arm 34 relative to the base 32. When position sensors are incorporated into the arm 34, the calibration process of step S11 below may be eliminated because the surgical system 10 can determine the location of the haptic device tracker 45 with respect to the base 32 based on the pose of the arm 34 provided by the position sensors.

Figure 6A:
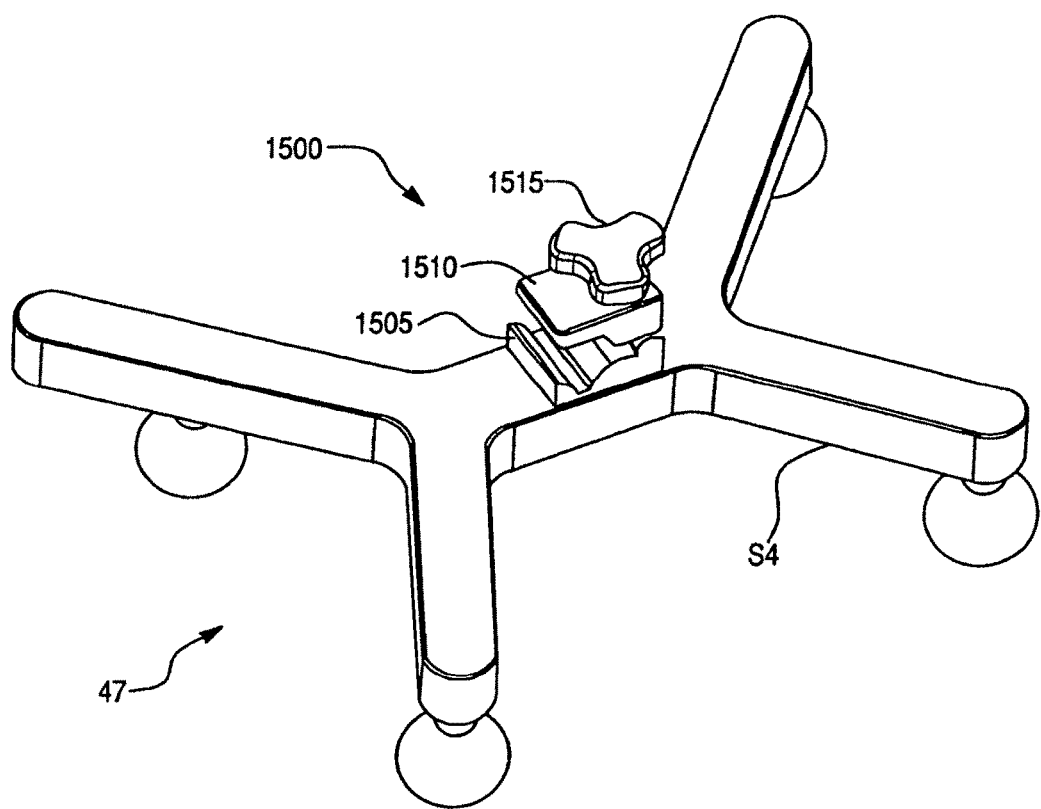
FIG. 6A is a perspective view of an embodiment of an end effector tracker according to the present invention.
Figure 6B:
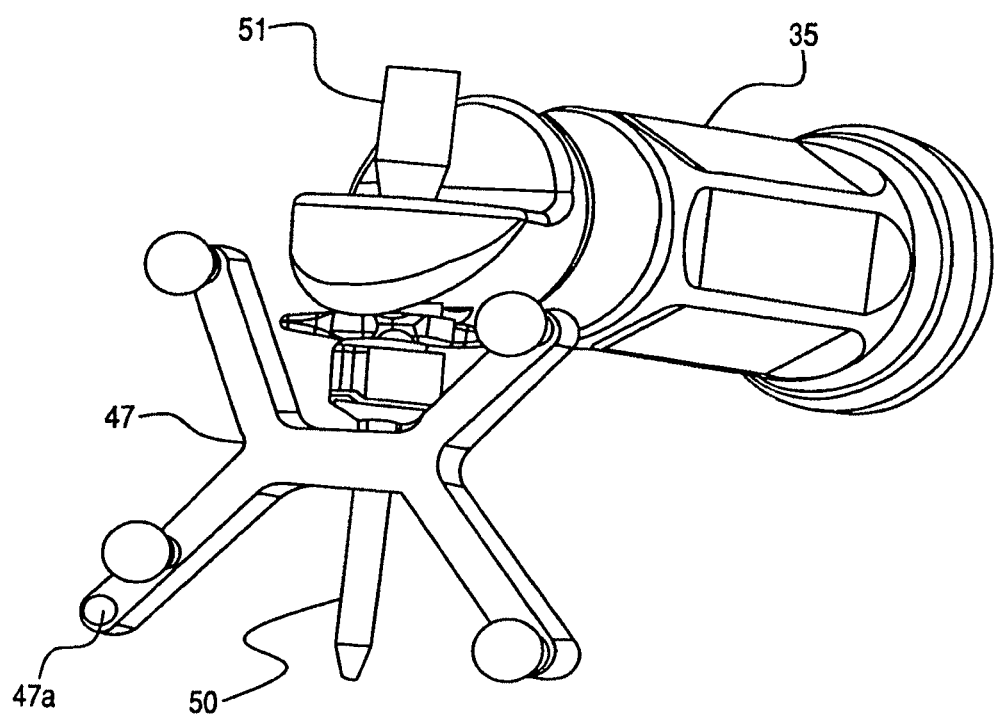
FIG. 6B is a perspective view of the end effector of FIG. 5A attached to a haptic device.

The end effector tracker 47 is adapted to enable the surgical system 10 to determine a pose of a distal end (e.g., a working end) of the haptic device 30. The end effector tracker 37 is preferably configured to be disposed on a distal end of the arm 33 or on the tool 50. For example, as shown in FIG. 6B, the end effector tracker 47 may be disposed on the end effector 35. As shown in FIG. 6A, the end effector tracker 47 may include a unique array S4 of markers (e.g., reflective spheres) and may be adapted to be affixed to the end effector 35 in any known manner, such as, for example, with a clamping device, threaded connection, magnet, or the like. As shown in FIG. 6A, in one embodiment, the end effector tracker 47 is affixed to the end effector 35 with a clamp 1500. The clamp 1500 may be formed integrally with the array S4 or affixed to the array S4 in any conventional manner, such as with mechanical hardware, adhesive, welding, and the like. The clamp 1500 includes a first portion 1505, a second portion 1510, and a thumbscrew 1515. The first and second portions 1505 and 1510 are shaped to receive a portion of the end effector, such as a cylindrical portion of the tool 50 or the tool holder 51. For example, as shown in FIG. 6A, the first portion 1505 may have a planar surface and the second portion 1510 may have a V-shaped groove so that the first and second portions 1505 and 1510 can securely receive the tool 50 or the tool holder 51 when tightened together. To install the end effector tracker 47 on the end effector 35, the first and second portions 1505 and 1515 of the clamp 1500 are disposed around the tool 50 or the tool holder 51 and tightened together using the thumbscrew 1515. The end effector tracker 47 may also include a feature to aid in properly orienting the end effector tracker 47 when installing the end effector tracker 47 on the haptic device 30. For example, the end effector tracker 47 may include a divot 47a as shown in FIG. 6B.

In one embodiment, the end effector tracker 47 is used only during calibration of the haptic device 30 (as discussed below in connection with step S9 of FIG. 13) and is removed prior to performance of the surgical procedure. In this embodiment, the end effector tracker 47 is disposed on the end effector 35 (as shown in FIG. 6B) and the haptic device tracker 45 is mounted to the base 32 of the haptic device 30 (e.g., via the adjustable arm 34 as shown in FIG. 2A) so that a position of the haptic device tracker 45 with respect to the haptic device 30 is adjustable. Because the position of the haptic device tracker 45 is adjustable (as opposed to permanently fixed), the surgical system 10 does not know the location of the haptic device tracker 45 with respect to the haptic device 30. To determine the geometric relationship between the haptic device 30 and the haptic device tracker 45, the calibration process utilizes the end effector tracker 47. Although the end effector tracker 47 may remain on the haptic device 30 for the entire surgical procedure (or any portion thereof), it is advantageous to remove the end effector tracker 47 when the calibration process is complete. For example, the user may desire to remove the end effector tracker 47 to prevent the tracker 47 from interfering with the user's grip on the haptic device 30, the patient's anatomy, medical instruments and equipment, and/or other personnel in the operating room. Another advantage of removing the end effector tracker 47 is that movement of the end effector tracker 47 during the surgical procedure may result in degraded performance of the surgical system 10 due to delays or limited bandwidth as the tracking system 40 measures the movement end effector tracker 47.

In an alternative embodiment, the end effector tracker 47 may be eliminated. In this embodiment, the haptic device tracker 45 is fixed in a permanent position on the haptic device 30. Because the haptic device tracker 45 is fixed in a permanent position on the haptic device 30, the relationship between the haptic device tracker 45 and the coordinate frame of the haptic device 30 is known. Accordingly, the surgical system 10 does not need the end effector tracker 47 for calibration to establish a relationship between the haptic device tracker 45 and the coordinate frame of the haptic device 30. In this embodiment, the haptic device tracker 45 may be rigidly mounted on the haptic device 30 in any position that permits the tracking system 40 to see the array S3 of the haptic device tracker 45, that is close enough to the surgical site so as not to degrade accuracy, and that will not hinder the user or interfere with other personnel or objects in the surgical environment.

In another alternative embodiment, the haptic device 30 is firmly locked in position. For example, the haptic device 30 may be bolted to a floor of the operating room or otherwise fixed in place. As a result, the global or gross position of the haptic device 30 does not change substantially so the surgical system 10 does not need to track the global or gross position of the haptic device 30. Thus, the haptic device tracker 45 may be eliminated. In this embodiment, the end effector tracker 47 may be used to determine an initial position of the haptic device 30 after the haptic device 30 is locked in place.

In another alternative embodiment, the tracking system 40 is attached to the haptic device 30 in a permanently fixed position. For example, the tracking system 40 (including the detection device 41) may be mounted directly on the haptic device 30 or connected to the haptic device 30 via a rigid mounting arm or bracket so that the tracking system is fixed in position with respect to the haptic device 30. In this embodiment, the haptic device tracker 45 and the end effector tracker 47 may be eliminated because a position of the tracking system 40 relative to the haptic device 30 is fixed and may be established during a calibration procedure performed, for example, during manufacture or set up of the haptic device 30.

In another alternative embodiment, the tracking system 40 is attached to the haptic device 30 in an adjustable manner. For example, the tracking system 40 (including the detection device 41) may be connected to the haptic device 30 with an arm, such as the adjustable arm 34 (described above in connection with the haptic device tracker 45) so that the tracking system 40 is moveable from a first position to a second position relative to the haptic device 30. After the arm and the tracking system 40 are locked in place, a calibration can be performed to determine a position of the tracking system 40 relative to the haptic device 30. The calibration may be performed, for example, using the end effector tracker 47.

Figure 7:
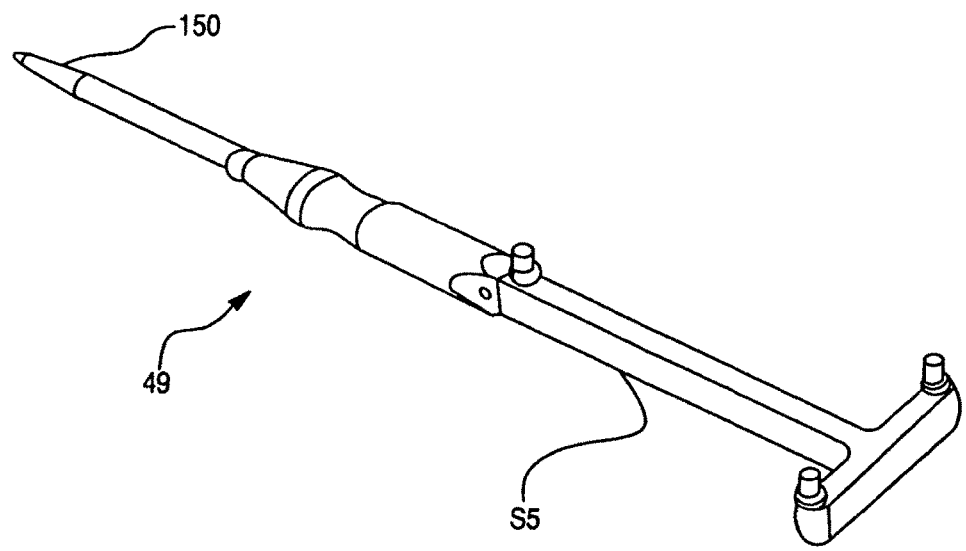
FIG. 7 is a perspective view of an embodiment of an instrument tracker according to the present invention.

The instrument tracker 49 is adapted to be coupled to an instrument 150 that is held manually in the hand of the user (as opposed, for example, to the tool 50 that is attached to the end effector 35). The instrument 150 may be, for example, a probe, such as a registration probe (e.g., a straight or hooked probe). As shown in FIG. 7, the instrument tracker 49 may comprise a unique array S5 of markers (e.g., reflective spheres) formed integrally with the instrument 150 or affixed to the instrument 150 in any known manner, such as with mechanical hardware, adhesive, welding, a threaded connection, a clamping device, a clip, or the like. When the instrument tracker 49 is removably connected to the instrument 150, such as with a clip or a clamping device, the instrument tracker 49 should be calibrated to the instrument 150 to determine a relationship between the instrument tracker 49 and a geometry of the instrument 150. Calibration may be accomplished in any suitable manner, such as with a tool calibrator having a divot or a V-groove (e.g., as described in U.S. Patent Application Pub. No. US 2003/0209096, which is hereby incorporated by reference herein in its entirety). One advantage of using a clip or clamping device (such as the clamp 1500 shown in FIG. 6A) to connect the tracker 49 to the instrument 150 is that the clip or clamping device may be adjustable to fit various sizes of instruments. Thus, a single clip or clamping device may be used with multiple instruments. Knowing a geometric relationship between the array S5 and the instrument 150, the surgical system 10 is able to calculate a position of a tip of the instrument 150 in physical space. Thus, the instrument 150 can be used to register an object by touching a tip of the instrument 150 to a relevant portion of the object. For example, the instrument 150 may be used to register a bone of the patient by touching landmarks on the bone or points on a surface of the bone. The instrument 150 may also be used to verify proper alignment of an implant installed in the patient by touching the tip of the instrument 150 to predefined verification features (e.g., divots) located on the implant.

Figure 29:
FIG. 29 is a view of an embodiment of a surgical navigation screen showing a registration step according to the present invention.
Figure 30:
FIG. 30 is a view of an embodiment of a surgical navigation screen showing a registration step according to the present invention.
Figure 31:
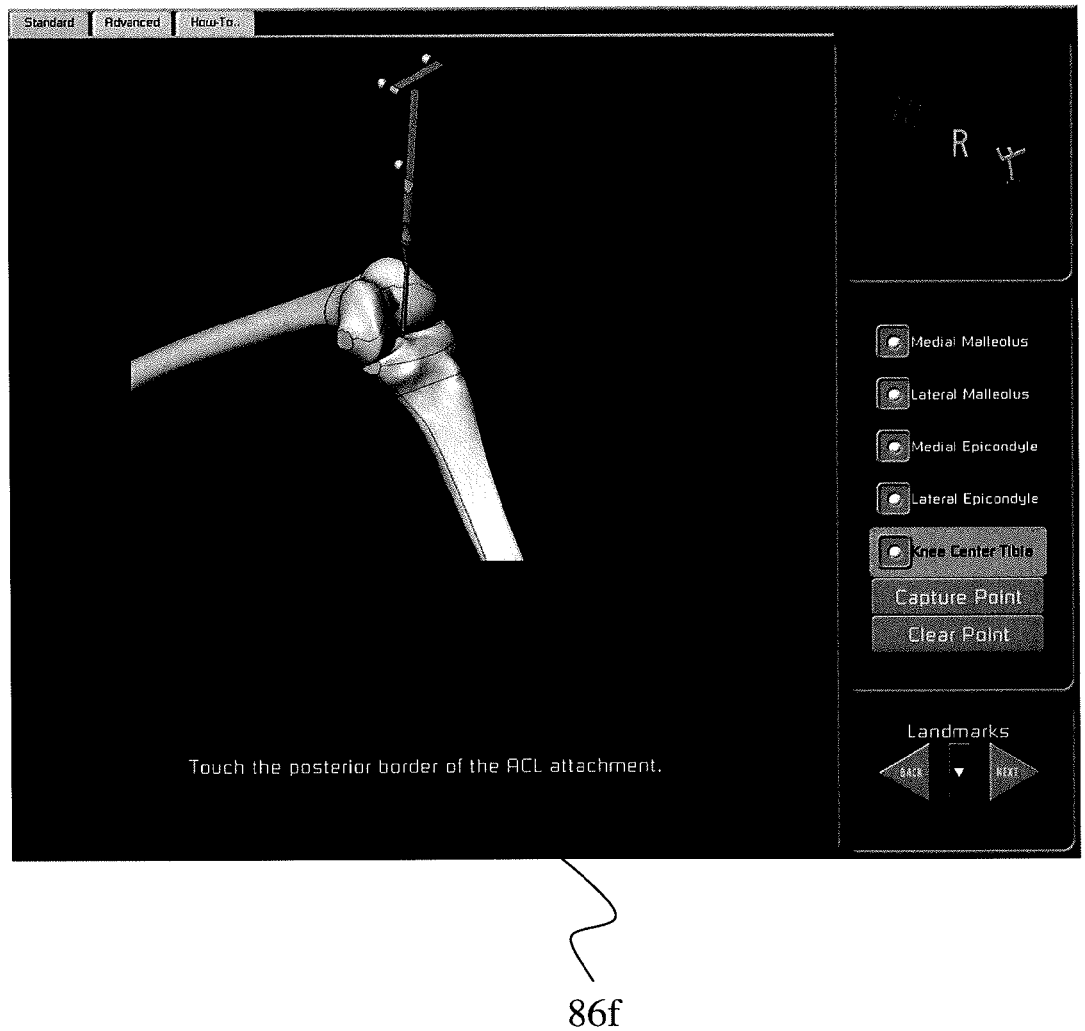
FIG. 31 is a view of an embodiment of a surgical navigation screen showing a registration step according to the present invention.

The instrument tracker 49 may also be configured to verify calibration of the instrument 150. For example, another tracker (e.g., the tracker 43, 45, or 47) may include a divot into which the user can insert the tip of the instrument 150. In one embodiment, as shown in FIG. 6B, the end effector tracker 47 includes a divot 47a into which the user can insert the tip of the instrument 150. The detection device 41 can then acquire pose data for the instrument tracker 49 and the end effector tracker 47, and the surgical system 10 can compare an actual geometric relationship between the trackers 47 and 49 to an expected geometric relationship. Deviation between the actual and expected geometric relationships indicates that a physical parameter (e.g., straightness, tip position, etc.) of the instrument 150 is out of calibration. As shown in FIG. 29, during the verification process, the surgical system 10 may display a screen showing a graphical representation of the instrument 150, the instrument tracker 49, and the end effector tracker 47 on the display device 23.

Figure 8:
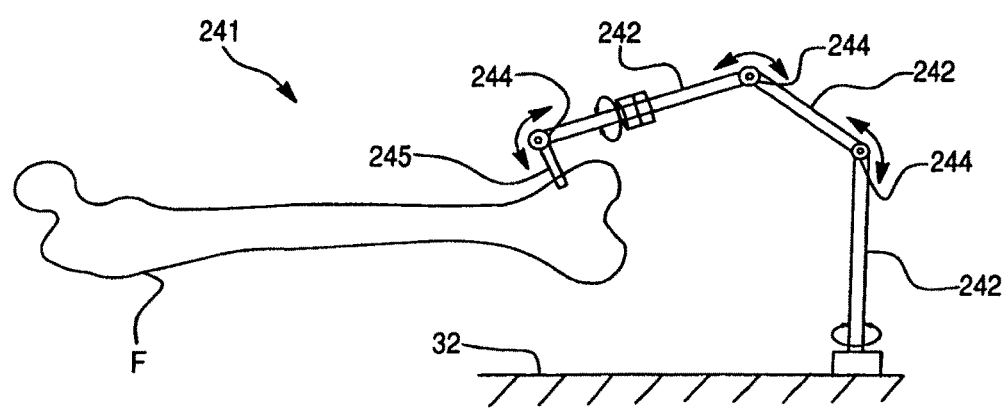
FIG. 8 is a view of an embodiment of a mechanical tracking system according to the present invention.

The tracking system 40 may additionally or alternatively include a mechanical tracking system. In contrast to the non-mechanical tracking system (which includes a detection device 41 that is remote from the trackers 43, 45, 47, and 49), a mechanical tracking system may be configured to include a detection device (e.g., an articulating arm having joint encoders) that is mechanically linked (i.e., physically connected) to the tracked object. The tracking system 40 may include any known mechanical tracking system, such as, for example, a mechanical tracking system as described in U.S. Pat. Nos. 6,033,415 and/or 6,322,567, each of which is hereby incorporated by reference herein in its entirety. In one embodiment, the tracking system 40 includes a mechanical tracking system having a jointed mechanical arm 241 (e.g., an articulated arm having six or more degrees of freedom) adapted to track a bone of the patient. As shown in FIG. 8, the arm 241 has a proximal end affixed to the base 32 of the haptic device 30 and a freely moveable distal end fixed to the femur F of the patient. Alternatively, the proximal end may be affixed to any other suitable location (such as, for example, to a rail of an operating table, a leg holder, etc.) but is preferably connected (e.g., directly or via a bracket) to the base 32 of the haptic device 30 so that the arm 241 moves globally with the haptic device 30. The distal end of the arm 241 includes an fixation device 245 adapted for rigid fixation to the femur F, such as, for example, a bone pin, bone screw, clamp, wearable device, surgical staple, or the like. The arm 241 is configured to have multiple degrees of freedom. For example, in one embodiment, as shown in FIG. 8, the arm 241 includes a plurality of links 242 connected at joints 244. Each joint 244 incorporates one or more position sensors (not shown) to track a pose of the arm 241. The position sensors may include any suitable sensor, such as, for example, the position sensors described above in connection with the arm 33 of the haptic device 30. In operation, as the femur F moves, the distal end of the arm travels with the femur F. The position sensors (and appropriate software) produce measurements of a pose of the distal end of the arm relative to the proximal end of the arm fixed to the haptic device 30. In this manner, motion of the femur F relative to the haptic device 30 is captured. The mechanical tracking system 240 may also include a second arm that is identical to the arm 241 but is rigidly affixed to the tibia T to enable the tracking system 240 to track motion of the tibia T. In this manner, the mechanical tracking system 240 may be used to track the femur F and the tibia T so that the surgical system 10 can detect bone motion in real time during surgery. Using bone motion data in conjunction with appropriate software, the surgical system 10 can compensate for the bone motion in real time during surgery.

One advantage of the mechanical tracking system over a non-mechanical tracking system is that the detection device (i.e., the arm 241) is physically connected to the tracked object and therefore does not require a line of site to "see" markers on the tracked object. Thus, the user and other personnel may freely move about the operating room during a surgical procedure without worrying about blocking an invisible line of sight between a set of markers and an optical camera. Another advantage of the mechanical tracking system is that the arm 241 may be physically connected to the haptic device 30 (e.g., to the base 32). Such a configuration eliminates the need to track a global or gross position of the haptic device 30 relative to the patient (e.g., using the haptic device tracker 45 as described above). There is no need to track the global or gross position of the haptic device 30 because the arm 241 moves with the haptic device 30. As a result, the haptic device 30 may be repositioned during a procedure without having to be recalibrated to a bone motion tracking system. Additionally, mechanical tracking systems may be more accurate than non-mechanical tracking systems and may enable faster update rates to the computer 21 and/or the computer 31. Faster update rates are possible because a mechanical tracking system is hardwired to the computer 21 and/or the computer 31. Thus, the update rate is limited only by the speed of the computer 21 and/or the computer 31.

Figure 14A:
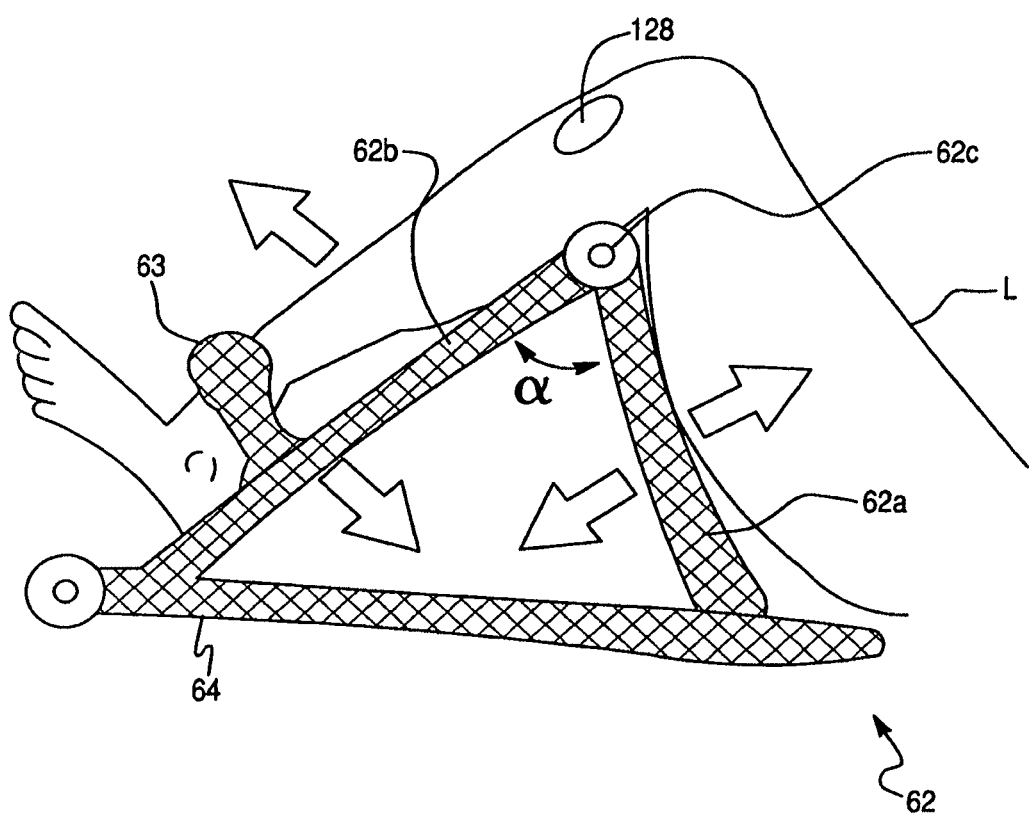
FIG. 14A shows an embodiment of a leg holder according to the present invention.

In an alternative embodiment, the arm 241 of the mechanical tracking system may be attached to an operating table, a leg holder 62 (e.g., as shown in FIG. 14A), or other structure in the surgical environment. In this embodiment, a calibration is performed to determine a pose of the arm 241 relative to the haptic device 30. For example, in one embodiment, the calibration is performed by placing the distal end (e.g., the end effector 35) of haptic device 30 in a known geometric relationship with the distal end of the arm 241. In another embodiment, the distal end of the arm 241 is placed in a known geometric relationship with the base 32 of the haptic device 30. In yet another embodiment, the distal end (e.g., the end effector 35) of the haptic device 30 is brought into a known geometric relationship with a base of the arm 241.

When the tracking system 40 includes the mechanical tracking system, the arm 241 may be used to register the patient's anatomy. For example, the user may use the arm 241 to register the tibia T while the second arm (i.e., the arm that is identical to the arm 241 but that is affixed to the tibia T) tracks motion of the tibia T. Registration may be accomplished, for example, by pointing a tip of the distal end of the arm 241 to anatomical landmarks on the tibia T and/or by touching points on (or "painting") a surface of the tibia T with the tip of the distal end of the arm 241. As the user touches landmarks on the tibia T and/or paints a surface of the tibia T, the surgical system 10 acquires data from the position sensors in the arm 241 and determines a pose of the tip of the arm 241. Simultaneously, the second arm provides data regarding motion of the tibia T so that the surgical system 10 can account for bone motion during registration. Based on the bone motion data and knowledge of the position of the tip of the arm 241, the surgical system 10 is able to register the tibia T to the diagnostic images and/or the anatomical model of the patient's anatomy in the computing system 20. In a similar manner, the second arm may be used to register the femur F while the arm 241 (which is affixed to the femur F) tracks motion of the femur F. The patient's anatomy may also be registered, for example, using a non-mechanical tracking system in combination with a tracked probe (e.g., the instrument 150 with the instrument tracker 49) and/or using the haptic device 30 (e.g., as described below in connection with step S8 of FIG. 13).

As shown in FIG. 1, the tracking system 40 may be coupled to the haptic device 30 via an interface 100b. The interface 100b includes a physical interface and a software interface. The physical interface may be any known interface such as, for example, a wired interface (e.g., serial, USB, Ethernet, CAN bus, and/or other cable communication interface) and/or a wireless interface (e.g., wireless Ethernet, wireless serial, infrared, and/or other wireless communication system). The software interface may be resident on the computer 21 and/or the computer 31 and enables the haptic device 30 and the computing system 20 to communicate with and control operation of the tracking system 40.

The surgical system 10 is adapted to be connected to a power source. The power source may be any known power source, such as, for example, an electrical outlet, a battery, a fuel cell, and/or a generator and may be connected to the surgical system 10 using conventional hardware (e.g., cords, cables, surge protectors, switches, battery backup/UPS, isolation transformer, etc.). The surgical system 10 preferably includes a user-activated device for manually controlling a supply of power to the tool 50. For example, the surgical system 10 may include a foot pedal (or other switching device) that can be positioned on the floor of the operating room in proximity to the user. Depressing the foot pedal causes the power source to supply power to the tool 50 (or to a compressed air supply in the case of a pneumatic tool 50). Conversely, releasing the foot pedal disrupts the flow of power to the tool 50. The surgical system 10 may also be adapted to automatically disrupt the flow of power to the tool 50 to promote safety. For example, the surgical system 10 may include programs or processes (e.g., running on the computer 21 and/or the computer 31) configured to shut off the tool 50 if a dangerous condition is detected, such as, for example, when the anatomy tracker 43 and/or the haptic device tracker 45 become occluded during a critical operation such as bone cutting.

In operation, the computing system 20, the haptic device 30, and the tracking system 40 cooperate to enable the surgical system 10 to provide haptic guidance to the user during a surgical procedure. The surgical system 10 provides haptic guidance by simulating the human tactile system using a force feedback haptic interface (i.e., the haptic device 30) to enable the user to interact with a virtual environment. The haptic device 30 generates computer controlled forces to convey to the user a sense of natural feel of the virtual environment and virtual (or haptic) objects within the virtual environment. The computer controlled forces are displayed (i.e., reflected or conveyed) to the user to make him sense the tactile feel of the virtual objects. For example, as the user manipulates the tool 50, the surgical system 10 determines the position and orientation of the tool 50. Collisions between a virtual representation of the tool 50 and virtual objects in the virtual environment are detected.

If a collision occurs, the surgical system 10 calculates haptic reaction forces based on a penetration depth of the virtual tool into the virtual object. The calculated reaction forces are mapped over the virtual object surface and appropriate force vectors are fed back to the user through the haptic device 30. As used herein, the term "virtual object" (or "haptic object") can be used to refer to different objects. For example, the virtual object may be a representation of a physical object, such as an implant or surgical tool. Alternatively, the virtual object may represent material to be removed from the anatomy, material to be retained on the anatomy, and/or anatomy (or other objects) with which contact with the tool 50 is to be avoided. The virtual object may also represent a pathway, a guide wire, a boundary, a border, or other limit or demarcation.

Figure 40:
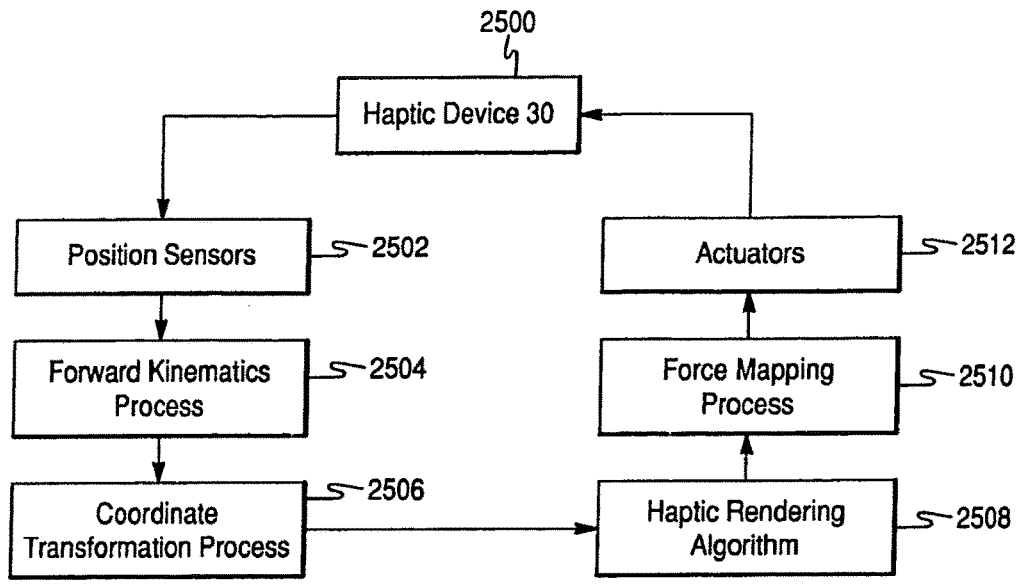
FIG. 40 is a block diagram of an embodiment of a haptic rendering process according to the present invention.

To enable the user to interact with the virtual environment, the surgical system 10 employs a haptic rendering process. One embodiment of such a process is represented graphically in FIG. 40. In operation, position sensors (block 2502) of the haptic device 30 (block 2500) provide data to a forward kinematics process (block 2504). Output of the forward kinematics process is input to a coordinate transformation process (block 2506). A haptic rendering algorithm (block 2508) receives data from the coordinate transformation process and provides input to a force mapping process (block 2510). Based on the results of the force mapping process, actuators (block 2512) of the haptic device 30 are actuated to convey an appropriate haptic wrench (i.e., force and/or torque) to the user. The position sensors of block 2502 and the actuators of block 2512 are described above in connection with the arm 33 of the haptic device 30. The forward kinematics process of block 2504 and the coordinate transform process of block 2506 are discussed below in connection with step S708 of FIG. 43. The haptic rendering algorithm of block 2508 and the force mapping process of block 2510 are discussed below in connection with FIG. 50.

The haptic rendering process may include any suitable haptic rendering process, such as, for example, a haptic rendering process as described in U.S. Pat. No. 6,111,577; C. B. Zilles & J. K. Salisbury, *A constraint-based god-object method for haptic display*, Proceedings of the IEEE/RSJ International Conference on Intelligent Robots and Systems, Vol. 3, pp. 146-51, 1995; T. V. Thompson II, D. E. Johnson & E. Cohen, *Direct haptic rendering of sculptured models*, Proceedings of the Symposium on Interactive 3D Graphics, pp. 167-76, 1997; K. Salisbury & C. Tar, *Haptic rendering of surfaces defined by implicit functions*, Proceedings of the ASME Dynamic Systems and Control Division, DSC-Vol. 61, pp. 61-67, 1997; and/or J. E. Colgate, M. C. Stanley & J. M. Brown, *Issues in the haptic display of tool use*, Proceedings of the IEEE/RSJ International Conference on Intelligent Robots and Systems, Vol. 3, pp. 140-45, 1995, each of which is hereby incorporated by reference herein in its entirety.

The virtual environment created by the haptic rendering process includes virtual (or haptic) objects that interact with a virtual representation of the tool 50. Interaction between the virtual objects and the virtual representation of the tool 50 may be point-based or ray-based. In a preferred embodiment, the surgical system 10 employs point-based haptic interaction where only a virtual point, or haptic interaction point (HIP), interacts with virtual objects in the virtual environment. The HIP corresponds to a physical point on the haptic device 30, such as, for example, a tip of the tool 50.

The HIP is coupled to the physical point on the physical haptic device 30 by a virtual spring/damper model. The virtual object with which the HIP interacts may be, for example, a haptic object 705 (shown in FIG. 42) having a surface 707 and a haptic force normal vector $F_n$. A penetration depth $d_i$ is a distance between the HIP and the nearest point on the surface 707. The penetration depth $d_i$ represents the depth of penetration of the HIP into the haptic object 705.

Figure 41:
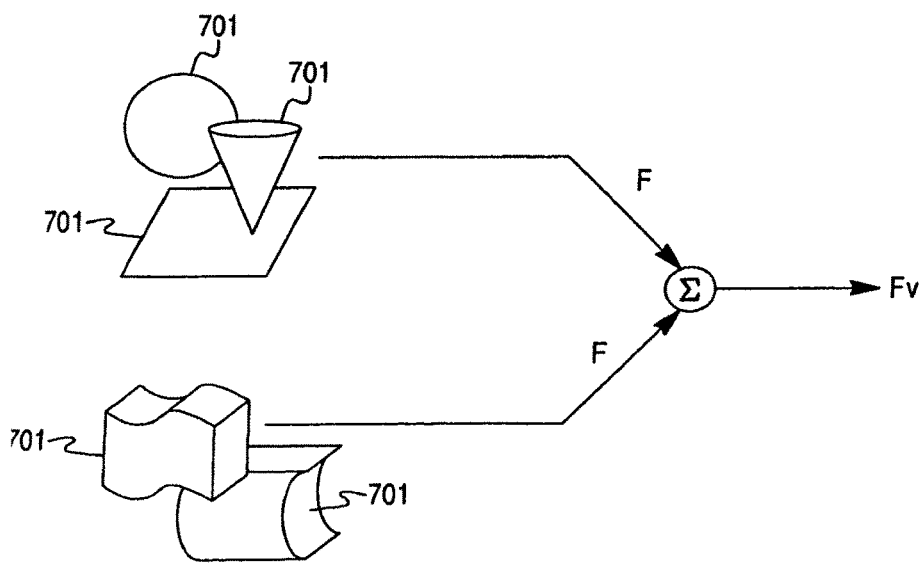
FIG. 41 is a representation of multiple haptic objects that are superimposed.

The virtual (or haptic) objects can be modeled, for example, using 3D geometric primitive objects, 3D polygonal objects, mathematical equations, computer models, surface models, and/or voxel arrays. Haptic objects may be static, quasi-static, dynamic, continuous, discontinuous, time varying, and/or existing only at certain times. In one embodiment, the haptic object is modeled using one or more functions of tool position, orientation, velocity, and/or acceleration. Thus, in the case of a surgical bone cutting operation, the haptic rendering process may produce a mapping of output wrench versus tool position. The mapping may be configured so that the output wrench fed back to the user is sufficient to resist further penetration of the virtual tool (or HIP) into the haptic object. In this manner, a virtual cutting boundary is established. The virtual boundary is associated with (e.g., registered to) the physical anatomy of the patient, an image of the anatomy, and/or other coordinate frame of interest. A haptic object rendered by the haptic rendering process may function as a pathway (e.g., a guide wire), may be repulsive (e.g., configured to repel the tool 50 from entering an interior of a haptic object), may function as a container (e.g., to maintain the tool 50 within the interior of the haptic object), and/or may have portions that repel and portions that contain. As shown in FIG. 41, multiple haptic objects 701 may be superimposed so that force vectors F from each of the haptic objects 701 are combined to yield a resultant haptic force vector $F_v$. In one embodiment, the output from each haptic object 701 comprises a Cartesian force vector with respect to an inertial coordinate frame and having linear properties. The maximum number of haptic objects may be determined based on computational costs.

A haptic object may be customized to include any desired shape, such as, for example, anatomically contoured implant shapes, protective boundaries for sensitive structures (e.g., intra-articular anatomy), image-derived tumor boundaries, and virtual fixtures for in vivo assembly of implant components. In one embodiment, the haptic object may be uniquely contoured to match a disease state of the patient. For example, the haptic object may define a virtual cutting boundary that encompasses only diseased bone. Thus, the haptic object can be used to guide the user in removing the diseased bone while sparing healthy surrounding bone. In this manner, the surgical system 10 enables the user to sculpt bone in a customized manner, including complex geometries and curves that are not possible with conventional cutting jigs and saw guides. As a result, the surgical system 10 facilitates bone sparing surgical procedures and implant designs that are smaller in size and adapted for a patient's unique disease state.

Figure 9:
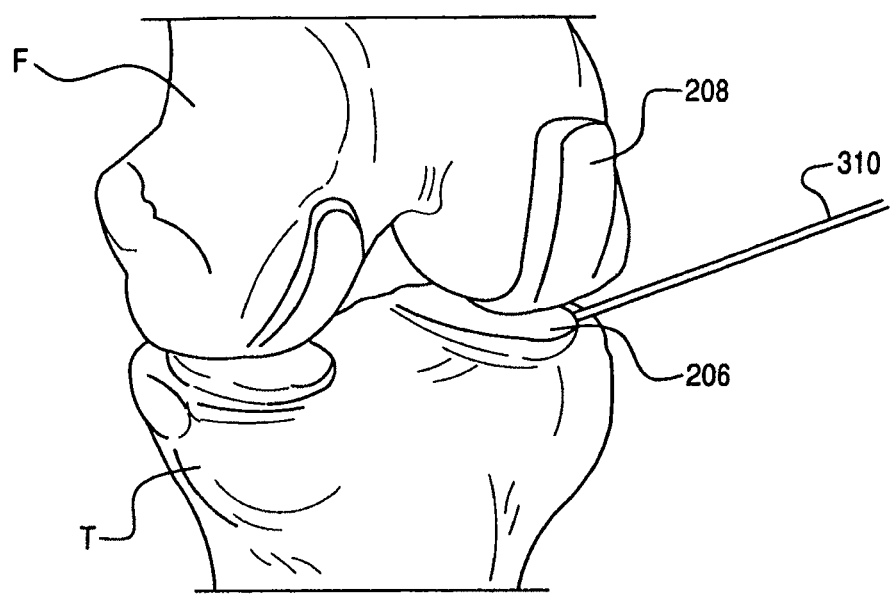
FIG. 9 is a perspective view of a femur and a tibia showing an embodiment of a graphical representation of a haptic object according to the present invention.
Figure 10A:
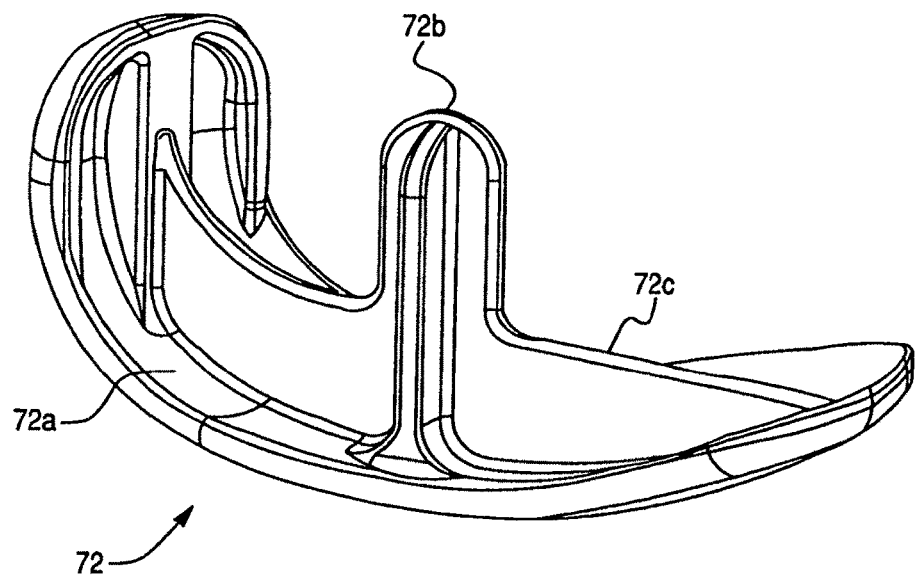
FIG. 10A is a perspective view of an embodiment of a femoral component according to the present invention.
Figure 10B:
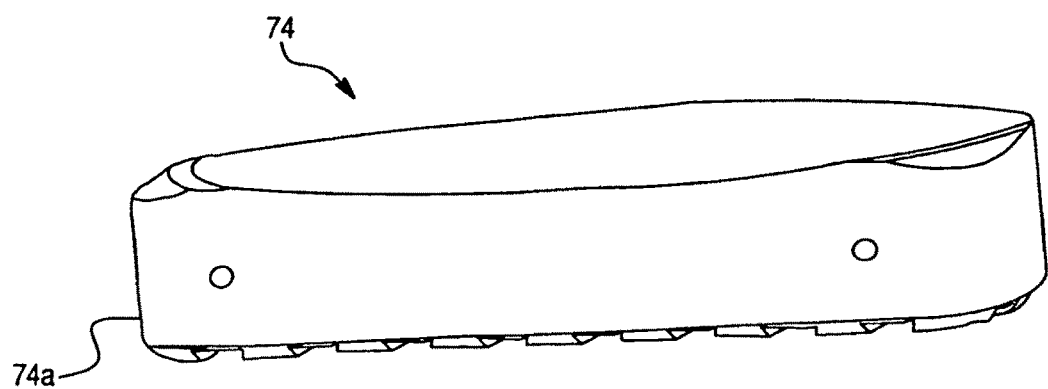
FIG. 10B is a perspective view of an embodiment of a tibial component according to the present invention.

A haptic object may have an associated spatial or geometric representation that can be graphically represented on the display device 23. The graphical representation may be selected so as to convey useful information to the user. For example, as shown in FIG. 1, a haptic object 300 configured assist the user in guiding the tool 50 to the surgical site may be represented graphically as a funnel shaped volume. As a virtual tool corresponding to the physical tool 50 moves through and interacts with the haptic object 300, haptic forces are reflected to the user so that the tool 50 is directed to the surgical site. Alternatively, as shown in FIG. 9, a haptic object 310 may be represented graphically as a guide wire. As the virtual tool moves along and interacts with the haptic object 310, haptic forces are reflected to the user so that the tool 50 is guided directly to the surgical site. In one embodiment, a haptic object defining a virtual cutting boundary for an implant may be depicted on the display device 23 as a graphical image having a shape that substantially corresponds to a shape of the implant. Thus, a haptic object 208 defining a virtual cutting boundary for a femoral component 72 (shown in FIG. 10A) may have a corresponding graphical representation as shown in FIG. 9. Similarly, a haptic object 206 defining a virtual cutting boundary for a tibial component 74 (shown in FIG. 10B) may have a corresponding graphical representation as shown in FIG. 9.

Figure 42:
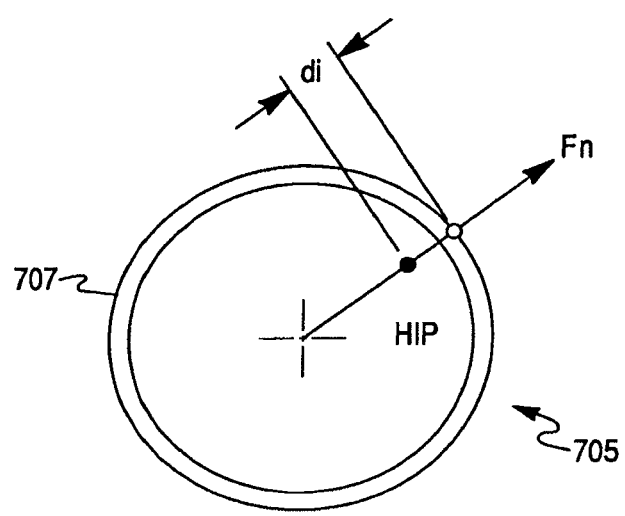
FIG. 42 is a representation of an embodiment of a 3D geometric haptic object according to the present invention.

Haptic objects having simple volumes are preferably modeled with a combination of 3D implicit surface objects such as planes, spheres, cones, cylinders, etc. For example, the haptic object 705 shown in FIG. 42 is a sphere. Surfaces of the haptic object 705 are continuously smooth, and solutions to the penetration depth $d_i$ and the haptic force normal vector $F_n$ can be obtained at a non-expensive, fixed computational cost from compact mathematical surface functions based on the haptic interaction point (HIP). For more complex objects, polygon based haptic rendering techniques may be used.

Figure 43:
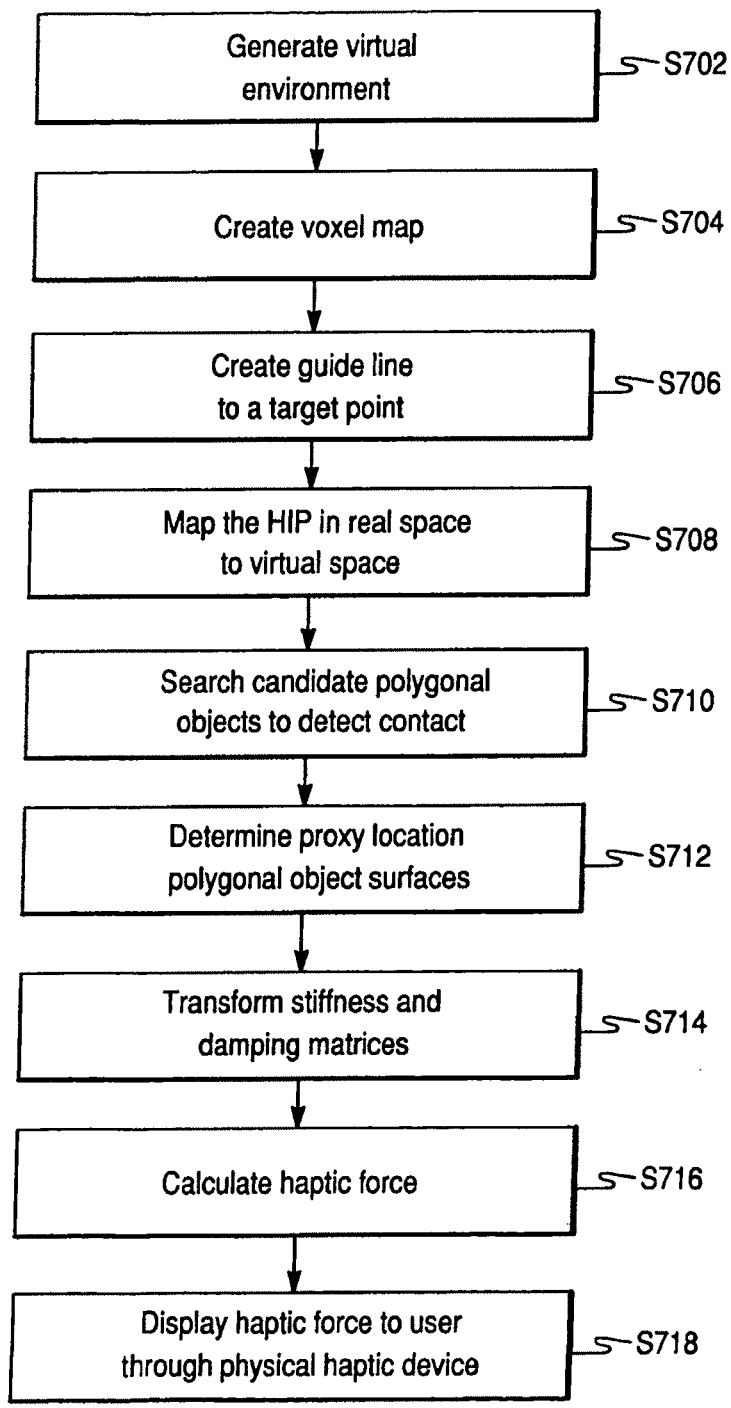
FIG. 43 is a block diagram of an embodiment of a polygon based haptic rendering process according to the present invention.
Figure 44:
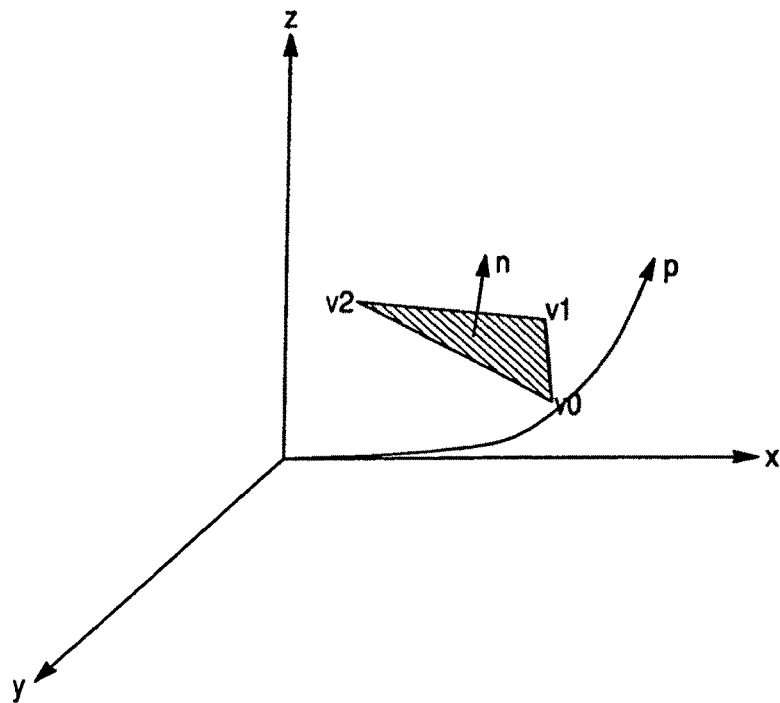
FIG. 44 is a representation of an embodiment of a polygon surface object according to the present invention.

FIG. 43 illustrates an embodiment of a polygon based haptic rendering process according to the present invention. In step S702, a virtual environment with which the user can interact is generated using, for example, computer-aided design (CAD) software. The virtual environment may be created, for example, using an explicit surface model. In one embodiment, the virtual environment includes a 3D virtual (or haptic) object comprising multiple polygonal surface objects. As shown in FIG. 44, each surface object is preferably triangular and represented by three nodes (or vertices) v0, v1, and v2 and a normal vector n. The virtual object can be re-shaped to compensate for a physical diameter of the tool 50, for example, by offsetting the walls of the virtual object by a radius of the tool 50. To improve computational performance, which is important in real-time applications, the polygonal surface objects can be re-meshed, for example, to eliminate polygons smaller than a desired spatial resolution. When the virtual object is a closed cavity, creation of the virtual object using a CAD system may be simplified by generating the virtual object with two surfaces: an outer object surface and an inner cavity surface. Using only the inner cavity surface, however, may advantageously reduce the required volume for rendering and the number of polygonal objects (e.g., triangles, polygons, etc.). In one embodiment, the rendering process can support uni-directional entrance behavior to a closed virtual object, where the HIP is permitted to pass through the virtual object only if it is moving from outside to inside.

Figure 45:
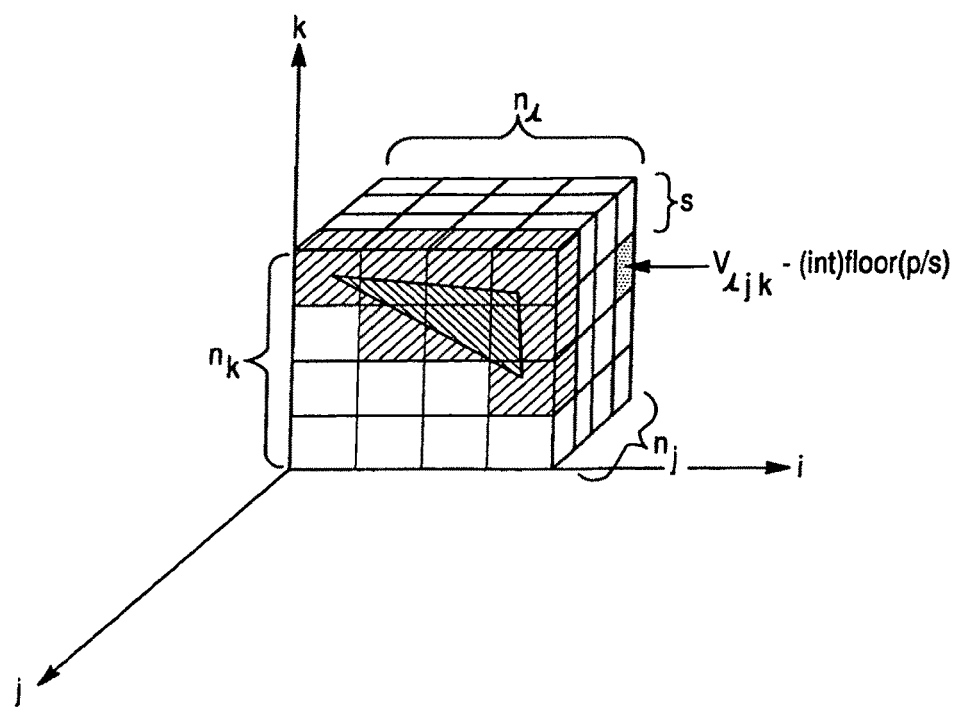
FIG. 45 is a representation of an embodiment of a voxel map according to the present invention.
Figure 46A:
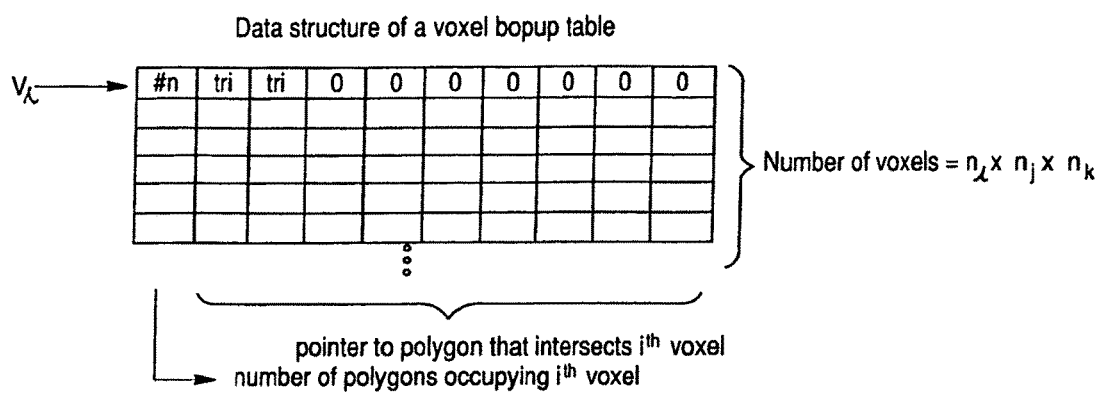
FIG. 46A is a representation of an embodiment of a voxel lookup table according to the present invention.
Figure 46B:
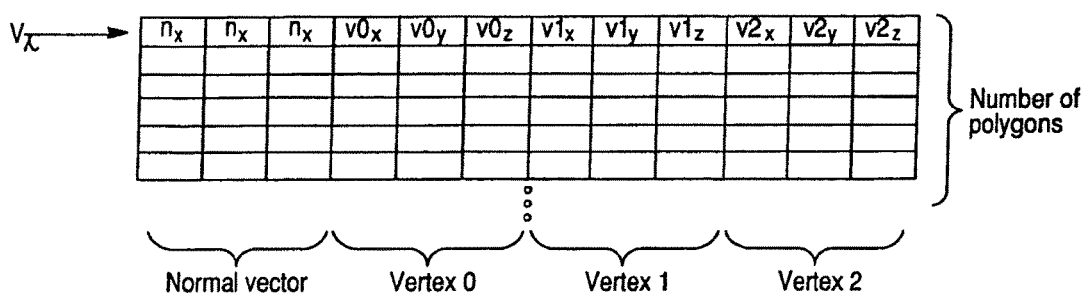
FIG. 46B is a representation of an embodiment of a polygon lookup table according to the present invention.

In step S704 of FIG. 43, the haptic rendering process creates a voxel map of the polygonal surface objects in the virtual environment. To create the voxel map, the virtual objects in the virtual environment are spatially partitioned into smaller cells (voxels) to reduce the number of polygonal surface objects and avoid unnecessary collision detection checks. As shown in FIG. 45, the virtual objects are segmented into an $n_i \times n_j \times n_k$ grid. The grid may be regularly spaced or may vary in resolution. Each voxel has a pointer to the polygons that occupy or intersect the voxel. Given a set of polygons, a voxel lookup table is constructed by the following steps: retrieve the polygon data (i.e., the xyz components for the vertices v0, v1, and v2) for a polygon of interest; create a bounding box around the polygon; add a unique identity number for the polygon to the voxels that are within the bounding box; and increase the total number of polygons occupying the voxel. These steps are repeated until the last polygon is processed. As shown in FIG. 44 (poly reference frame) and FIG. 45 (voxel reference frame), a point p in the poly frame is converted into the voxel frame using the formula $v_{ijk}$=(int)floor(p/s), where s is voxel size. Examples of voxel and polygon lookup tables are presented in FIGS. 46A and 46B, respectively.

Figure 47:
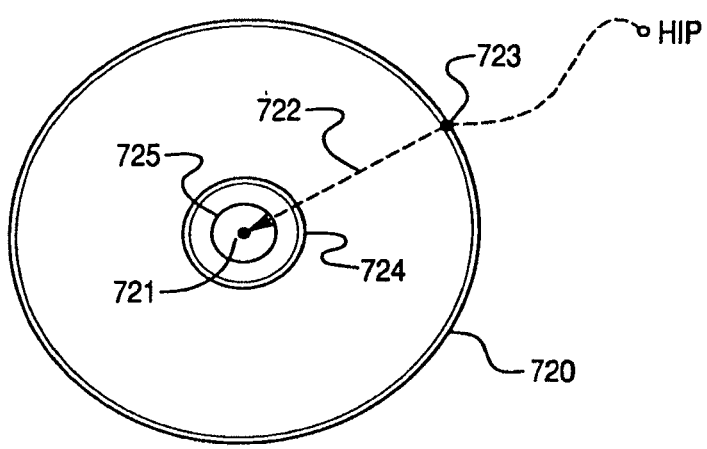
FIG. 47 illustrates an implementation of an embodiment of a virtual guide line according to the present invention.

In step S706 of FIG. 43, the haptic rendering process creates a guide line to a target point or a target region. The guide line functions as a pathway or guide wire that guides the HIP to a particular location. A guide line is useful, for example, to guide the user's movement of the physical tool 50 so that the tool 50 avoids critical anatomy. A guide line is also useful with a closed haptic volume that the user is unable to traverse. Implementation of a guide line is explained with reference to FIG. 47, which illustrates a virtual sphere 720. The sphere 720 includes an active zone defined by a center and a radius of the sphere 720. When the HIP is outside the active zone, the user can freely move the haptic device 30. When the HIP enters the active zone, the haptic device 30 is placed in an approach mode in which a guiding line segment 722 is created. The guiding line segment 722 extends, for example, from an entering point 723 on a surface of the sphere 720 to a target point 721 (e.g., a target point pair {pe, pt}). Normally, the center of the sphere 720 will be coincident with the target point (or will be within a target region). When the guiding line segment 722 is activated, the HIP can move freely along the guiding line segment 723. Motion of the HIP that deviates from the guiding line segment 722 (e.g., motion perpendicular to the guiding line segment 722), results in a resisting force that is fed back to the user. As the HIP approaches the target point, a distance from a current location of the HIP to the target point is monitored. When the distance is smaller than a confine radius, the behavior of the HIP is restricted, for example, by implementing a uni-directionally constrained virtual confining sphere 724. A radius of the confining sphere 724 is reduced as the HIP moves closer to the target point. When the distance from the HIP to the target point is smaller than a switch radius (represented in FIG. 47 by a switch sphere 725), haptic rendering of the virtual object begins.

Figure 48:
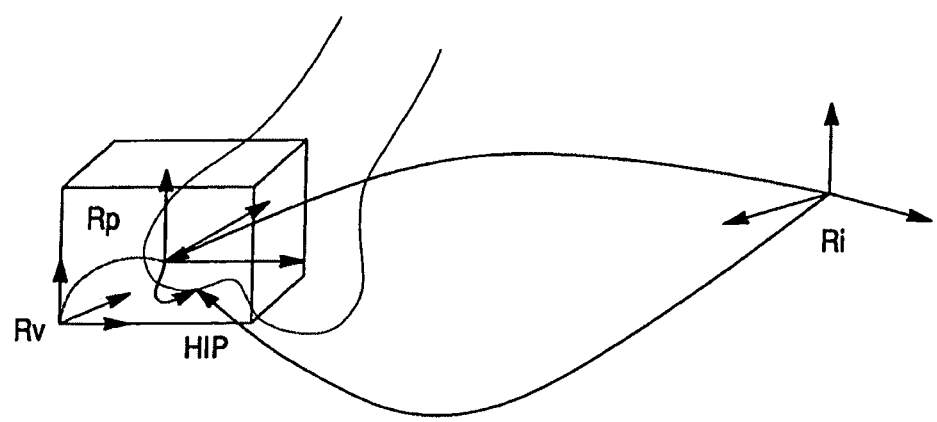
FIG. 48 is a graphical illustration of a coordinate transformation.

In step S708 of FIG. 43, the haptic rendering process maps the physical HIP (e.g., the tip of the tool 50) to virtual space. For example, the forward kinematics process (block 2504) of FIG. 40 computes a Cartesian position of the physical HIP with respect to an inertial reference frame Ri. The coordinate transformation process (block 2506) of FIG. 40 performs coordinate transformations between the inertial reference frame Ri, a poly frame Rp (a reference frame attached to a polygonal virtual object), and a voxel frame Rv (a reference frame attached to a voxel array) as illustrated in FIG. 48. Once the haptic rendering process has determined the position of the HIP with respect to the poly frame Rp, the haptic rendering process proceeds to step S710 and searches candidate polygonal objects by looking at occupied voxels and neighboring voxels. In step S712, the haptic rendering process checks for a collision (e.g., the HIP has passed through a polygonal object since the last rendering cycle) and determines a virtual proxy point location (e.g., a constrained location of the HIP along a surface of the virtual object) based on desired virtual proxy behaviors (as described below in connection with FIG. 49). In step S714, desired stiffness and damping matrices that are predefined in tool coordinates are transformed into inertial reference frame coordinates. In step S716, a haptic force to be fed back to the user through the haptic device 30 is computed based on a desired hardness of a virtual surface defined by the virtual spring and damping force that couples the HIP to the haptic device 30. In step S718, the computed haptic force is displayed or reflected to the user through the haptic device 30.

Figure 49A:
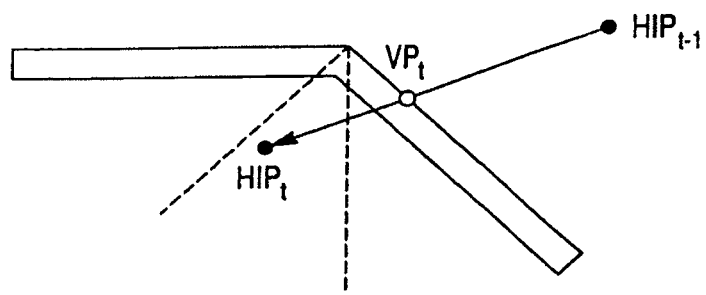
FIG. 49A is an illustration of a virtual proxy point location.
Figure 49B:
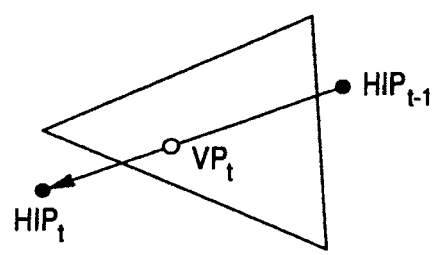
FIG. 49B is an illustration of a virtual proxy point location.

As shown in FIGS. 49A and 49B, a location of an initial virtual proxy point may be determined based on a location HIP(t) of the HIP at a current time t and a location HIP(t−1) of the HIP at a previous time t−1. For example, when the HIP is outside a virtual object, the haptic rendering process checks for an initial contact between the HIP and a surface of the virtual object by detecting an intersection between the polygonal surface objects that comprise the virtual object and a line segment L extending between the locations HIP(t) and HIP(t−1). A location VP(t) of the initial virtual proxy point is computed as the intersecting point of the line segment L and the polygonal surface objects.

Figure 50:
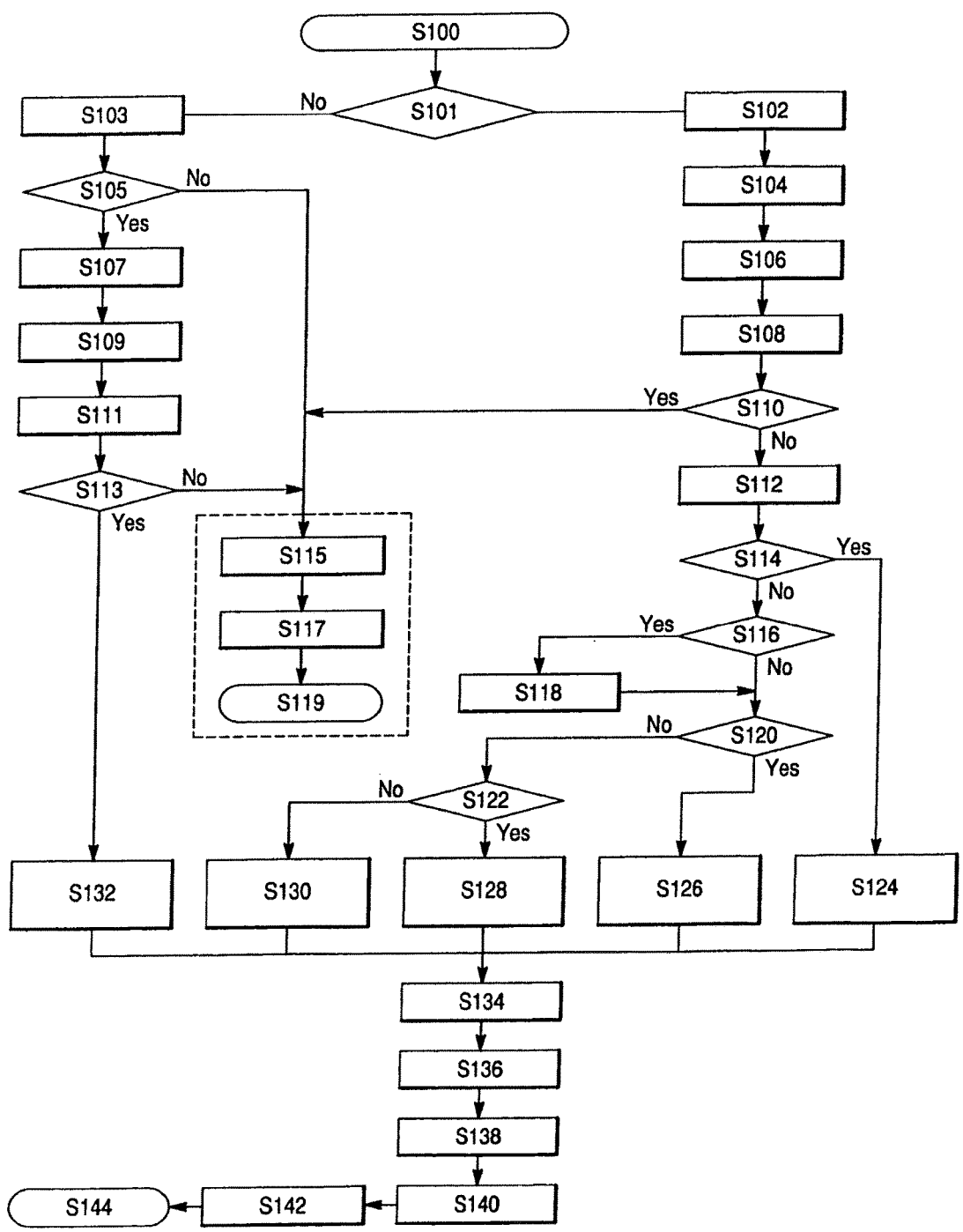
FIG. 50 is a flowchart of an embodiment of a haptic rendering algorithm according to the present invention.

FIG. 50 shows a flowchart detailing an embodiment of a haptic rendering algorithm (block 2508 of FIG. 40) based on polygonal surface objects according to the present invention. In step S100, the position of HIP(t) is updated and transformed to the poly reference frame. In step S101, the algorithm determines whether collisionDetectedFlag(t−1) has a value of 1. If not, in step S103, the algorithm maps the HIP(t) into voxel coordinates. In step S105, the algorithm determines whether the HIP(t) is inside a voxel bounding box. If not, no collision is detected, and the algorithm proceeds to step S115 where the haptic force is set to zero, step S117 where collisionDetectedFlag(t) is set to zero, and step S119 where the time advances to t=t+1. If step S105 determines that the HIP(t) is inside a voxel bounding box, the algorithm proceeds to step S107 and searches candidate polygons along a line segment of HIP(t) from a voxel lookup table. In step S109, the algorithm retrieves polygonal information from a polygon lookup table. In step S111, the algorithm tests an intersection of the line segment of HIP(t) with the polygons and, in step S113, determines whether an initial collision is detected. If no collision is detected, the algorithm proceeds to steps S115, S117, and S119 as described above. If a collision is detected, the algorithm proceeds to step S132 (described below).

In contrast, in step S101, if collisionDetectedFlag(t−1) has a value of 1, the algorithm follows the right branch of the flowchart. In step S102, the algorithm maps HIP(t) into voxel coordinates. In step S104, the algorithm searches neighboring polygons at the HIP(t) from a voxel lookup table. In step S106, the algorithm retrieves polygonal information from a polygon lookup table. In step S108, each neighboring polygon is tested to determine whether it is intersected by the line segment from HIP(t−1) to HIP(t). In step S110, the algorithm uses this information to determine whether the HIP(t) has exited the polygons. If so, the HIP is no longer penetrating the haptic object, and the algorithm proceeds to steps S115, S117, and S119 as described above. If step S110 determines that the HIP has not exited the polygons, the algorithm proceeds to step S112 where the algorithm projects the HIP(t) on each neighboring polygon along the corresponding surface normal vectors of the polygons. If the projected HIP(t) is within a polygon, the algorithm sets the polygon as an On-Polygon and stores the intersecting point. Otherwise, the algorithm finds a point on a boundary of the polygon that is closest to the projected HIP(t) (all within the plane of the polygon) and stores the point. This process is repeated for each neighboring polygon. The algorithm then has decision points based on whether an Active Polygon from the previous time cycle, AP(t−1), was set to be an On-Polygon in step 22 and whether only a single polygon was set to be an On-Polygon in the current cycle. Each case is handled as described below.

Figure 51A:
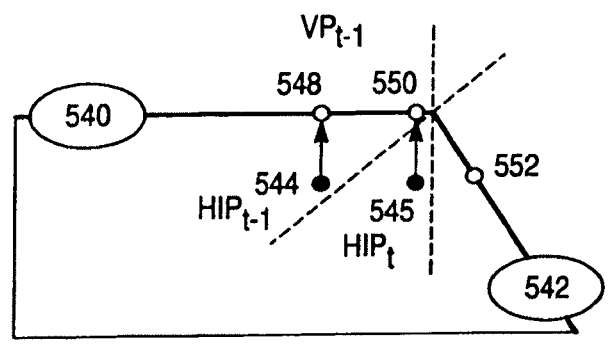
FIG. 51A is an pictorial representation of an active polygon priority behavior.

In step S114, the algorithm determines whether a previous active polygon (on which the virtual proxy point was in contact) is still an On-Polygon. If so, in step S124 (ActivePolygonPriority), this polygonal surface has priority to be the active polygon, even if other polygons are identified as On-Polygons. AP(t) is therefore maintained, and VP(t) is set at the closest point on the active polygonal surface. For example, FIG. 51A shows a convex portion of a virtual object defined by two adjoining surfaces 540 and 542. When the HIP at t−1 was at a location 544, the surface 540 is On-Polygon and 542 is not On-Polygon. The virtual proxy point location at t−1 lies at a location 548. If the HIP moves to a location 546, both of the surfaces 540 and 542 are On-Polygons and locations 550 and 552 are candidates for proxy point location. In this situation, the surface 540 will be selected as an active polygon and the proxy point location will be updated at the location 550. Granting the previous active polygon priority in this way prevents the choice of the location 552 for the proxy point, which would result in an unnatural jump in the proxy point position and the resulting haptic interaction forces experienced by the user.

If step S114 determines that the previous active polygon is not an On-Polygon, the algorithm proceeds to step S116 to determine whether a single On-Polygon is detected. If a single On-Polygon is not detected in step S116, the algorithm checks again in step S120. If a single On-Polygon is detected in step S116, the algorithm proceeds to step S118 and augments the On-Polygons for a concave corner before checking again for a single On-Polygon in step S120. If a single On-Polygon is detected in step S120, the algorithm proceeds to step S126 (described below). If a single On-Polygon is not detected in step S120, the algorithm proceeds to step S122 and determines whether multiple On-Polygons are detected. If so, the algorithm proceeds to step S128 (described below). Otherwise, the algorithm proceeds to step S130 (described below).

Figure 51B:
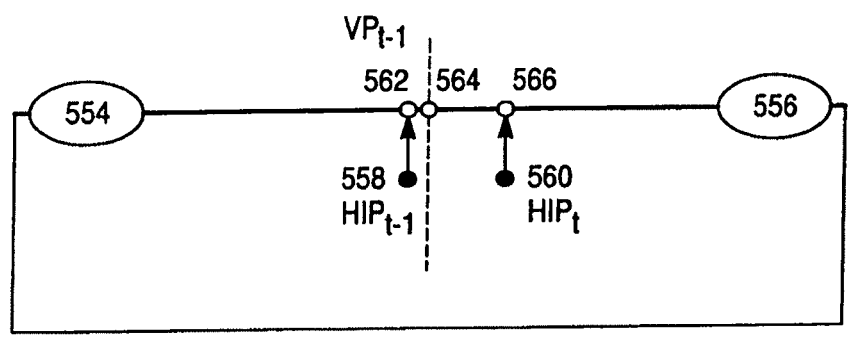
FIG. 51B is a pictorial representation of an On-Polygon priority behavior.

In step S126 (OnPolygonPriority), AP(t) is updated with a new On-Polygon and VP(t) is set at the closest point on the active polygonal surface. For example, as shown in FIG. 51B, a virtual object has two adjoining surfaces 554 and 556. At a time t−1, the HIP is at a location 558 and the proxy point is at a location 562. When the HIP crosses over a surface border line 564 as the HIP moves from the location 558 to a location 560, a surface 556 becomes On-Polygon and a location 566 becomes the new proxy point location. Thus, if a new single On-Polygon is detected, then the new single On-Polygon becomes the active polygon.

Figure 51C:
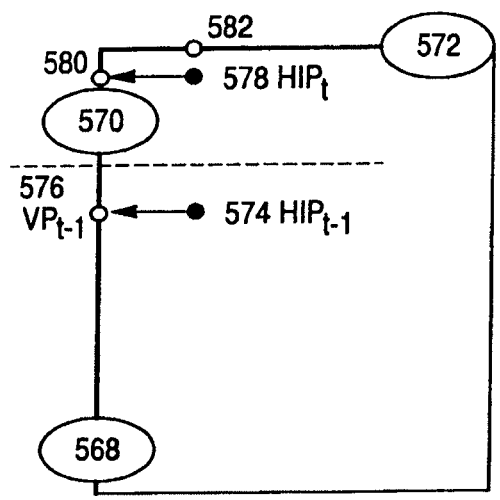
FIG. 51C is a pictorial representation of a continuous surface priority behavior.

In step S128 (ContinuousSurfacePriority), AP(t) is selected based on force vector deviation criteria and VP(t) is set at the closest point on the active polygonal surface. The algorithm detects the multiple new On-Polygons as illustrated in FIG. 51C, which shows a convex portion of a virtual object defined by three surfaces, 568, 570, and 572. As the HIP moves from a location 574 to a location 578, the algorithm detects two new On-Polygon surfaces, 570 and 572. Thus, locations 580 and 582 are candidates for a new virtual proxy point location. In this situation, the algorithm computes possible candidates of force vector, excluding a damping component, and compares a force vector deviation from a previous force vector deviation. The algorithm determines the active polygon so as to minimize the following objective function:

$$J_{continuousSurface} = \min_i \|f_{si,t} \cdot f_{t-1}\|$$

where $f_{si,t}$ represents a spring force vector defined by a current location of the HIP and a possible location of the virtual proxy point on the ith polygon and $f_{t-1}$ represents a haptic force displayed at previous time. In one embodiment, the surface 570 will be the new active polygon and a location 580 will be the new proxy point position.

Figure 51D:
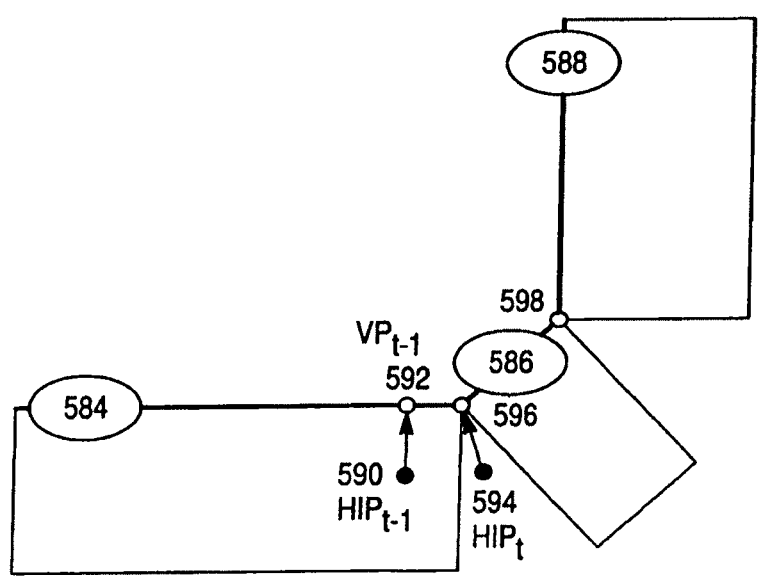
FIG. 51D is a pictorial representation of a minimum force priority behavior.

In step S130 (MinimumForcePriority), AP(t) is based on minimum force criteria and VP(t) is set at the closest point on the active polygonal surface. As shown in FIG. 51D, the HIP lies at position where no On-Polygon can be detected. FIG. 51D, illustrates a concave portion of a virtual object defined by three surfaces, 584, 586, and 588. When the HIP moves from a location 590 to a location 594, no surface is On-Polygon. A location 596 is the closest point to the surfaces 586 and 584, a location 598 is the closest point to the surface 588. In this situation, the algorithm computes distances between the current HIP and possible proxy point locations and determines a virtual proxy location to minimize the following objective function:

$$J_{minimumSpringForce} = \min_i \|x_{hip} - x_{i,vp}\|$$

where $x_{i,vp}$ represents a position of the possible virtual proxy point on the ith polygon and $x_{hip}$ represents a position of the current haptic interface point. In this situation, the algorithm sets either the surface 584 or the surface 586 as the On-Polygon depending on their processing sequence and the location 596 will be the proxy point location.

Figure 52A:
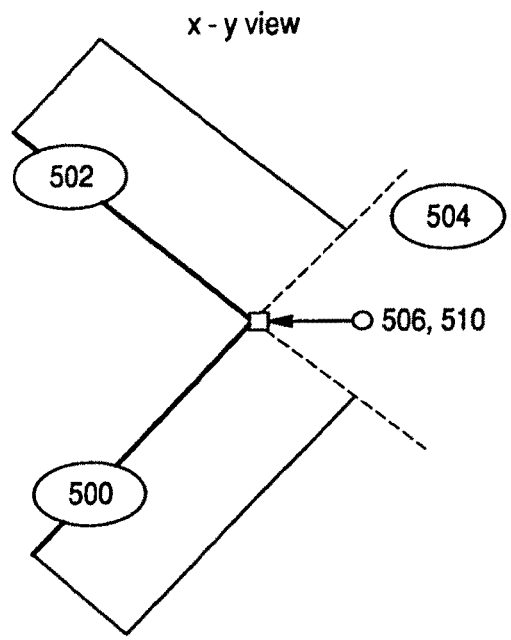
FIG. 52A is a pictorial representation of an x-y view of an augmenting concave corner behavior.
Figure 52B:
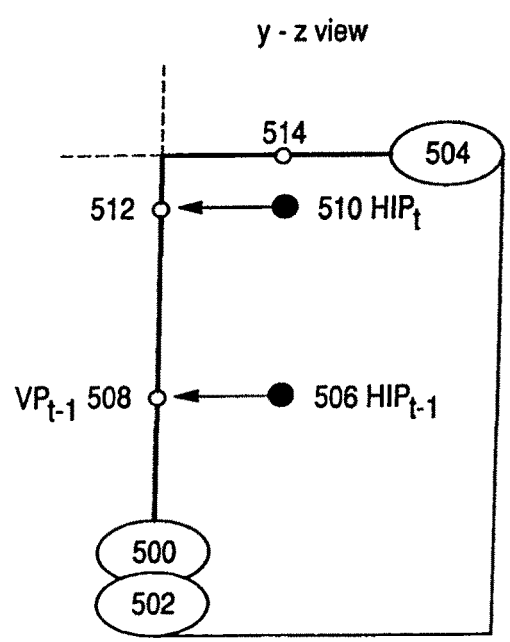
FIG. 52B is a pictorial representation of a y-z view of an augmenting concave corner behavior.

In step S132 (ContactPolygonPriority), AP(t) is updated with an intersected polygon and VP(t) is set at the closest point on the active polygonal surface. The algorithm augments the On-Polygon objects when a haptic interface point lies in a concave corner where the algorithm detects one On-Polygonal object and multiple concave surfaces. In this situation, the application sets the concave polygonal surface to On-Polygon so that continuous haptic rendering can happen at the concave corner. FIGS. 52A and 52B show a portion of a concave corner represented by three surfaces, 500, 502, and 504. As the haptic interface point moves from a location 506 (with a proxy point location 508) to a location 510, the surface 504 becomes the only On-Polygonal object. In order to avoid the situation in which the algorithm sets the surface 504 as an active polygonal surface due to On-Polygon priority behavior and selects a location 514 as the proxy point location, the algorithm augments the two concave surfaces 500 and 502 into On-Polygon objects. As a result, a location 512 will be a proxy point location according to continuous surface priority behavior.

In step S134, stiffness and damping matrices defined in tool coordinates as constant parameters are transformed into an inertial coordinate frame. When the physical haptic device 30 has different transmission devices, such as a cable driven transmission and a direct-driven transmission, isotropic spatial stiffness and damping gains can cause instability because the physical system has different dynamic properties in different directions. For this reason, the spatial stiffness and damping matrices can be defined with respect to the tool coordinates and need to be transformed into the inertial coordinate frame. The algorithm computes an adjoint transformation matrix based on current rotational and translational matrices and transforms the spatial stiffness and damping matrices. Let $^T K_s$ and $^I K_s$ denote the stiffness matrices measured in tool frame and inertial frame, respectively. Let $Ad_g$ denote the adjoint transformation matrix given as $$Ad_g = \begin{bmatrix} R & \hat{p}R \\ 0 & R \end{bmatrix}$$

Given a vector $p=(px, py, pz)^T$, $\hat{p}$ denotes a skew-symmetric matrix used for representing a cross product as a matrix-vector product:

$$\hat{p} = \begin{pmatrix} 0 & -p_x & p_y \\ p_x & 0 & -p_z \\ -p_y & p_z & 0 \end{pmatrix}$$

where R is the rotational matrix and p is the translational vector.

The algorithm computes the stiffness matrix in the inertial frame:

$$^I K_S = Ad_g^T {}^T K_S Ad_g$$

In step S136, the algorithm computes a spring haptic force vector based on the location of the haptic interface point and the virtual proxy point location according to Hooke's law:

$$F_{spring}(t) = {}^I K_S (x_{vp} - x_{hip})$$

where $x_{vp}$ represents a position of a current virtual proxy point, and $x_{hip}$ represents a position of a current haptic interface point.

In step S138, the algorithm computes a damping haptic force vector based on the relative motion between the haptic interface point and the virtual proxy point:

$$F_{damping}(t) = {}^I K_D (\dot{x}_{vp} - \dot{x}_{hip})$$

where $\dot{x}_{vp}$ represents motion of the virtual proxy point, $\dot{x}_{hip}$ represents motion of the haptic interface point, and $^I K_D$ represents the spatial damping matrix in an inertial frame.

In step S140, the sum of the damping force and spring force is sent to the physical haptic device 30 as a desired force output (step S718 of FIG. 43). Prior to controlling the actuators (block 2512 of FIG. 40) of the haptic device 30 to output force feedback, the force mapping process (block 2510 of FIG. 40) converts the desired force, $F_{desired}$, to joint torque, τ:

$$\tau = J^T F_{desired}$$

where $J^T$ is a Jacobian transpose. The computing system 20 then controls the actuators of the haptic device 30 to output the joint torque, τ.

In step S142, collisionDetectedFlag(t)=1. In step S144, the time advances to t=t+1. In cases where there may be a transmission with compliance, backlash, hysteresis, or non-linearities between the haptic device drive (e.g., motors) and position outputs (e.g., joints), it is beneficial to include position sensors on both the drive end and load end of the transmission. The load end sensors are used to compute all joint and endpoint positions because they will most accurately reflect the actual values. The drive end sensors are used to compute velocities in any damping computations, such as for $F_{damping}$ above, which helps avoid exciting the transmission dynamics.

According to one embodiment, the desired force feedback (or output wrench) of the haptic device 30 is determined based on a proximity of a portion of the haptic device 30 (e.g., the tool 50) to a virtual (or haptic) boundary associated with the representation of the anatomy. Thus, if the tool 50 is disposed a sufficient distance from the haptic boundary, a controller commands no haptic forces, and the user is free to move the tool 50 as if exploring empty space. However, as the tool 50 approaches or contacts the haptic boundary, the controller commands torques to the motors so as to exert the appropriate wrench on the user's hand via the interface 37. Preferably, a magnitude of the force feedback increases as the tool 50 approaches the virtual boundary and does not present a discontinuous step that may induce oscillation or unwanted vibration. For example, as the tool 50 approaches the haptic boundary, the haptic device 30 may exert a force in a direction opposite a direction of movement of the user interface 37 such that the user perceives a repulsive or counteracting force that slows and/or stops movement of the tool 50. In one embodiment, a rate of increase of the force as the tool 50 continues moving toward the haptic boundary may be, for example, in a range of 5 N/mm to 50 N/mm. In another embodiment, the rate of increase of the force may be approximately 20 N/mm. In this manner, the user is constrained to not penetrate the haptic boundary too deeply. When the tool 50 contacts the haptic boundary, the force may be such that the user feels as if the tool 50 has collided with a physical object, such as a wall. The magnitude of the force may prevent the user from penetrating the haptic boundary (e.g., a magnitude of approximately 100 N or greater) but is preferably set so that the user may breach the haptic boundary if desired (e.g., a magnitude in a range of approximately 20 N to approximately 60 N). Thus, the computing system 20 may be programmed to permit the user to overcome the force feedback and move the haptic device 30 to a desired location. In this manner, the haptic device 30 constrains the user against inadvertently violating the haptic boundary, but the user has the option to overpower the haptic device 30 and thus retains full control over the surgical procedure.

Figure 11A:
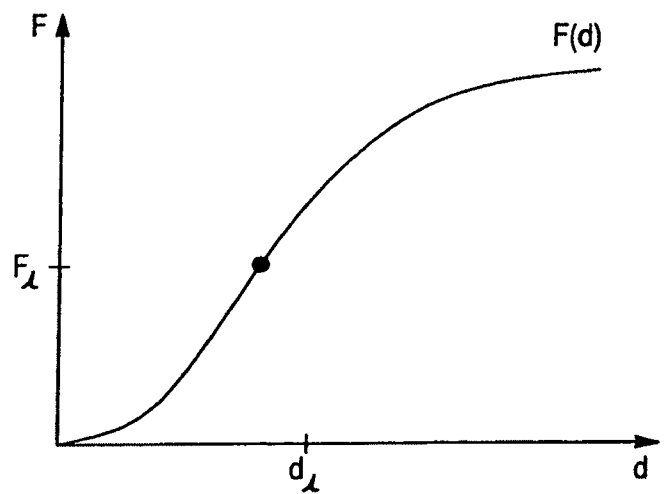
FIG. 11A is a graph of a force feedback curve according to an embodiment of the present invention.
Figure 11B:
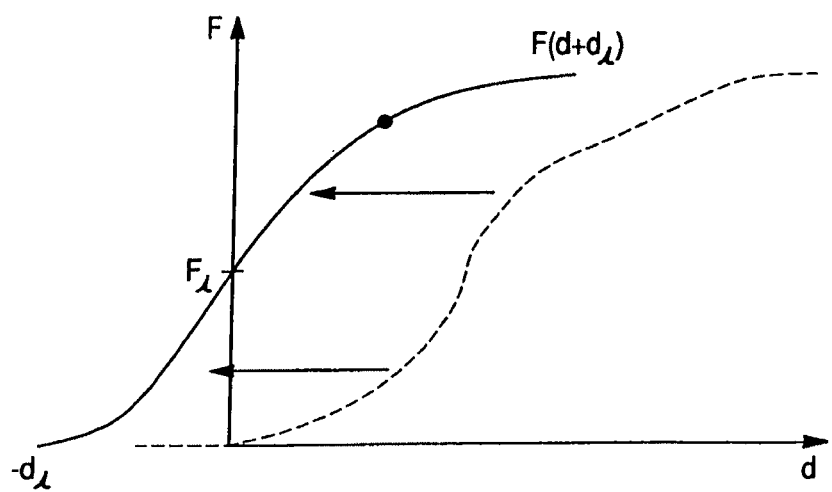
FIG. 11B is a graph of the force feedback curve of FIG. 11A shifted to the left.
Figure 11C:
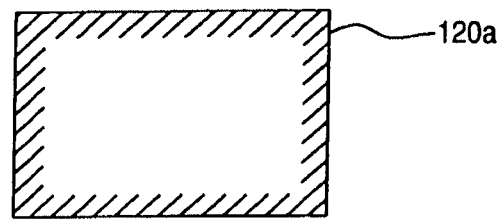
FIG. 11C is a graphical representation of an embodiment of a repulsive haptic object according to the present invention.
Figure 11D:
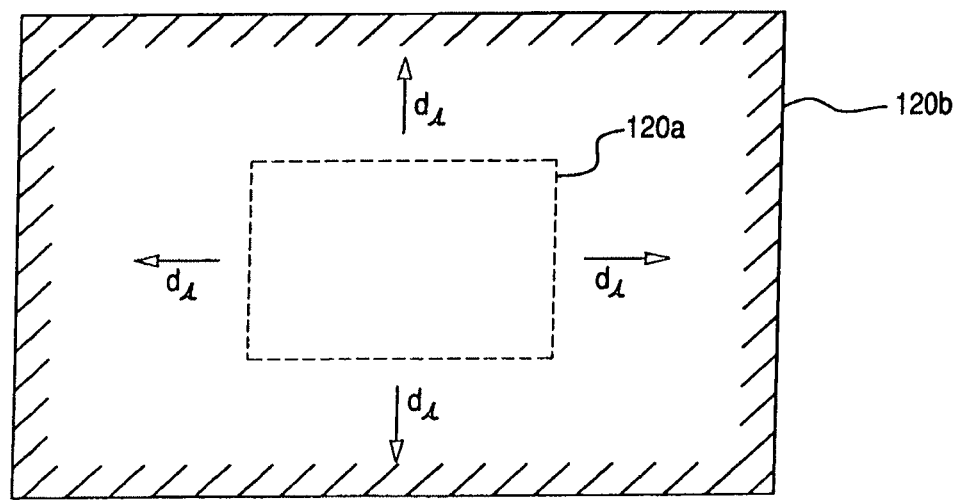
FIG. 11D is a graphical representation of an embodiment of a repulsive haptic object according to the present invention.
Figure 11E:
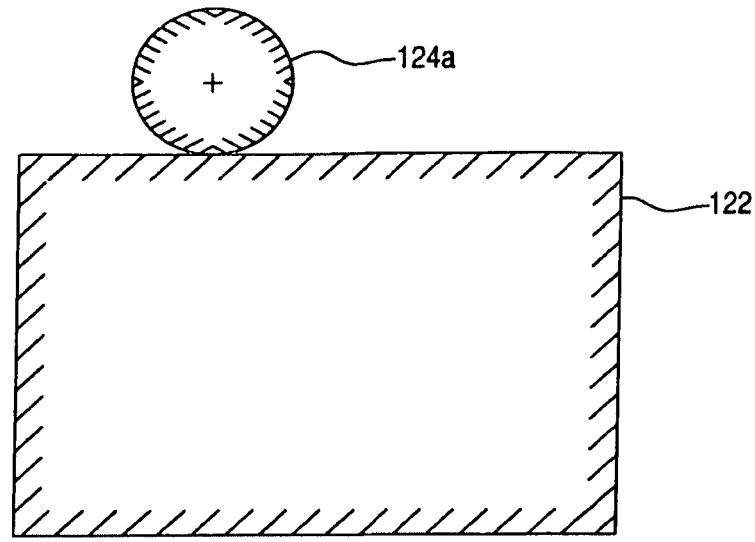
FIG. 11E is a graphical representation of an embodiment of virtual tool according to the present invention.
Figure 11F:
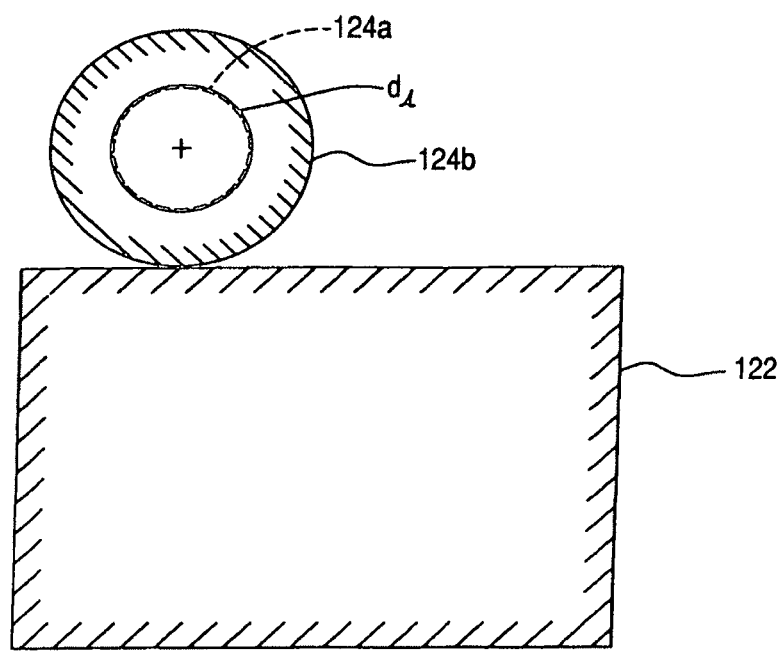
FIG. 11F is a graphical representation of an embodiment of virtual tool according to the present invention.

In one embodiment, the surgical system 10 includes a haptic tuning feature for customizing a force feedback function of the haptic object for a particular user. Such a feature is advantageous because each user has a unique surgical technique. Thus, different users may use differing amounts of force when maneuvering the tool 50. For example, users who maneuver the tool 50 with a light touch may sense haptic feedback earlier than users with a heavier touch. Rather than requiring the user with the heavier touch to alter his surgical technique to sufficiently sense the haptic feedback, the haptic tuning feature enables the force feedback function to be adjusted to accommodate each particular user. By adjusting (or tuning) the force feedback function, the user can manipulate the tool 50 with his preferred degree of force and still sufficiently perceive the haptic feedback exerted by the haptic device 30. As a result, the user's ability to maintain the tool within the haptic boundary is improved. For example, as shown in FIG. 11A, a force feedback curve includes a function F(d) that relates force F to distance d. The function F(d), for example, may result from or be a product of the haptic object, a coupling stiffness, or a stiffness function. In one embodiment, $F_i$ is a typical haptic interaction force for a user (or a group of users), and $d_i$ is a penetration depth or distance (e.g., penetration of the tool 50 into the haptic object) where $F_i=F(d_i)$ is true. As shown in FIG. 11B, shifting or offsetting the function F(d) to the left by, for example, $d_i$, results in a force feedback function $F(d+d_i)$ that causes the force F to be applied earlier (i.e., beginning at a penetration distance of $-d_i$ rather than at a penetration distance of zero) in a tool's approach to a haptic boundary. Similarly, shifting or offsetting the function F(d) to the right causes the force F to be applied later in the tool's approach to the haptic boundary. Thus, for a user with a surgical technique that is forceful, it is advantageous to offset the function F(d) to the left to prevent the user from inadvertently pushing too far into the haptic boundary. Thus, haptic tuning may be accomplished by offsetting a force feedback curve for controlling the haptic device 30 by a desired value. Haptic tuning can also be accomplished by altering a size of a haptic object. For example, a size of a repulsive haptic object 120a (shown in FIG. 11C) can be increased resulting in a haptic object 120b (shown in FIG. 11D). Similarly, a size of a representation of a surgical tool coupled to the haptic device 30 may be altered. For example, a size of a radius of a tip of a virtual tool 124a (shown in FIG. 11E) that interacts with a haptic object 122 can be increased resulting in a virtual tool 124b (shown in FIG. 11F). For a haptic object that acts as a container, tuning can be accomplished, for example, by reducing a size of the haptic object.

Figure 11G:
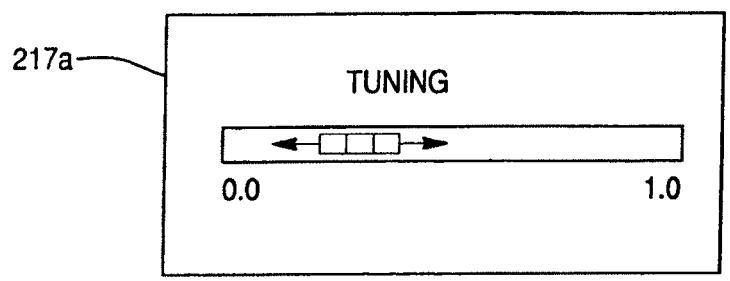
FIG. 11G shows an embodiment of a graphical selection interface according to the present invention.
Figure 11H:
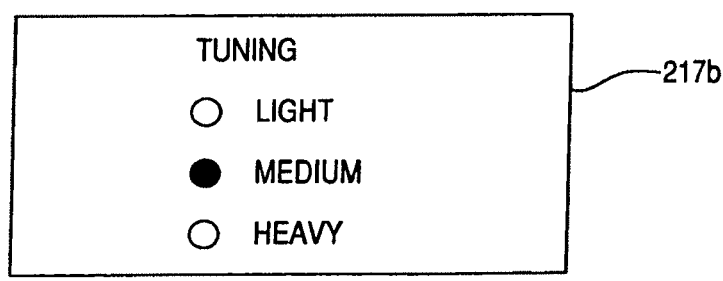
FIG. 11H shows an embodiment of a graphical selection interface according to the present invention.

To enable each user to tune the force feedback function, the computing system 20 preferably includes programming to enable a graphical selection interface that can be displayed on the display device 23. For example, as shown in FIGS. 11G and 11H, respectively, the graphical selection interface may be a graphical interface 217a that enables the user to set a tuning value, for example, between 0.0 and 1.0 and/or a graphical interface 217b that enables the user to select, for example, tuning for a "Light," "Medium," or "Heavy" touch. The computing system 20 may also be programmed to store a desired value of a tuning setting and to associate the desired value with a particular user (e.g., using a user ID tied to a user preference data file) so that the user does not have to select the tuning setting prior to each use of the surgical system 10.

The haptic device 30 is preferably configured to operate in various operating modes. For example, the haptic device 30 may be programmed to operate in an input mode, a hold mode, a safety mode, a free mode, an approach mode, a haptic (or burring) mode, and/or any other suitable mode. The operating mode may be selected manually by the user (e.g., using a selection button represented graphically on the display device 23 or a mode switch located on the haptic device 30 and/or the computing system 20) and/or automatically by a controller or software process. In the input mode, the haptic device 30 is enabled for use as an input device to input information to the surgical system 10. When the haptic device 30 is in the input mode, the user may operate the haptic device 30 as a joystick or other input device, for example, as described above in connection with the end effector 35 and/or in U.S. patent application Ser. No. 10/384, 078 (Pub. No. US 2004/0034282), which is hereby incorporated by reference herein in its entirety. Other methods of inputting information to the surgical system 10 include, for example, moving the wrist 36, moving a joint of the arm 33, and/or moving the arm 33 (or a portion thereof). For example, moving the arm 33 toward an object (e.g., a tracked object) may comprise a first input. Similarly, moving the arm 33 toward the object and twisting the wrist 36 may comprise a second input. Thus, the surgical system 10 may identify or distinguish user input based on, for example, a pose of the haptic device 30 with respect to a tracked object, movement of a portion of the haptic device 30 (e.g., the wrist 36), or a combination of pose and movement. In the hold mode, the arm 33 of the haptic device 30 may be locked in a particular pose. For example, the arm 33 may be locked using brakes, control servoing techniques, and/or any other appropriate hardware and/or software for stabilizing the arm 33. The user may desire to place the haptic device 30 in the hold mode, for example, during an activity such as bone cutting to rest, confer with a colleague, allow cleaning and irrigation of the surgical site, and the like. In the safety mode, the tool 50 coupled to the haptic device 30 may be disabled, for example, by shutting off power to the tool 50. In one embodiment, the safety mode and the hold mode may be executed simultaneously so that the tool 50 is disabled when the arm 33 of the haptic device 30 is locked in position.

In the free mode, the end effector 35 of the haptic device 30 is freely moveable within the workspace of the haptic device 30. Power to the tool 50 is preferably deactivated, and the haptic device 30 may be adapted to feel weightless to the user. A weightless feeling may be achieved, for example, by computing gravitational loads acting on the segments 33a, 33b, and 33c of the arm 33 and controlling motors of the haptic device 30 to counteract the gravitational loads. As a result, the user does not have to support the weight of the arm. The haptic device 30 may be in the free mode, for example, until the user is ready to direct the tool 50 to a surgical site on the patient's anatomy.

In the approach mode, the haptic device 30 is configured to guide the tool 50 to a target object, such as, for example, a surgical site, feature of interest on the patient's anatomy, and/or haptic object registered to the patient, while avoiding critical structures and anatomy. For example, in one embodiment, the approach mode enables interactive haptic positioning of the tool 50 as described in U.S. patent application Ser. No. 10/384,194 (Pub. No. US 2004/0034283), which is hereby incorporated by reference herein in its entirety. In another embodiment, the haptic rendering application may include a haptic object defining an approach volume (or boundary) that constrains the tool 50 to move toward the target object while avoiding sensitive features such as blood vessels, tendons, nerves, soft tissues, bone, existing implants, and the like. For example, as shown in FIG. 1, the approach volume may include the haptic object 300, which is substantially cone-shaped, funneling from a large diameter to a small diameter in a direction toward the target object (e.g., a proximal end of the tibia T or a distal end of the femur F). In operation, the user may freely move the tool 50 within the boundaries of the approach volume. As the user moves the tool 50 through the approach volume, however, the tapering funnel shape constrains tool movement so that the tool 50 does not penetrate the boundaries of the approach volume. In this manner, the tool 50 is guided directly to the surgical site. In another embodiment, shown in FIG. 9, the haptic rendering application creates a virtual object that represents a pathway from a first position to a second position. For example, the virtual object may include the haptic object 310, which is a virtual guide wire (e.g., a line) defining a pathway from a first position (e.g., a position of the tool 50 in physical space) to a second position that includes a target region of the anatomy (e.g., a target object such as the haptic object 206). In the approach mode, the virtual object is activated so that movement of a portion of the haptic device 30 (e.g., the tool 50) is constrained along the pathway defined by the haptic object 310. The surgical system 10 deactivates the virtual object when the tool 50 reaches the second position and activates the target object (e.g., the haptic object 206). The tool 50 may be automatically placed in the haptic (or burring) mode when the haptic object 206 is activated. In a preferred embodiment, the virtual object may be deactivated to enable the tool 50 to deviate from the pathway. Thus, the user can override the haptic guidance associated with the haptic object 310 to deviate from the guide wire path and maneuver the tool 50 around untracked objects (e.g., retractors, lamps, etc.) the cannot be accounted for when the virtual guide wire is created. Thus, the approach mode enables the user to quickly deliver the tool 50 to a target object while avoiding critical structures and anatomy. In the approach mode, power to the tool 50 is preferably deactivated so that the tool is not accidentally energized, for example, when the user is inserting the tool through an incision or navigating soft tissue in a joint. The approach mode generally precedes the haptic mode.

In the haptic (or burring) mode, the haptic device 30 is configured to provide haptic guidance to the user during a surgical activity such as bone preparation. In one embodiment, as shown in FIG. 9, the haptic rendering application may include the haptic object 206 defining a cutting volume on the tibia T. The haptic object 206 may have a shape that substantially corresponds to a shape of a surface 74*a* of the tibial component 74 (shown in FIG. 10B). Alternatively, the haptic object 206 may have a shape that is slightly larger than the shape of the surface 74*a* of the tibial component 74. One advantage of making the haptic object 206 larger than the implant is that the cutting volume defined by the haptic object 206 is then large enough to accommodate both the implant and a cement mantle that is disposed between the implant and the bone to secure the implant to the bone. A haptic object having a size that deviates from the size of the implant also enables implementation of the haptic tuning feature described above in connection with FIGS. 11A to 11F. The haptic device 30 may enter the haptic mode automatically, for example, when the tip of the tool 50 approaches a predefined point related to a feature of interest. In the haptic mode, the haptic object 206 may also be dynamically modified (e.g., by enabling and disabling portions of a haptic surface) to improve performance of the haptic device 30 when sculpting complex shapes or shapes with high curvature as described, for example, in U.S. patent application Ser. No. 10/384,194 (Pub. No. US 2004/0034283), which is hereby incorporated by reference herein in its entirety. In the haptic mode, power to the tool 50 is activated, and the tip of the tool 50 is constrained to stay within the cutting volume to enable a precise bone resection.

The haptic device 30 may utilize any suitable haptic control scheme, such as, for example, admittance control, impedance control, or hybrid control. In an admittance control mode, the haptic device 30 accepts force input and yields position (or motion) output. For example, the haptic device 30 measures or senses a wrench at a particular location on the haptic device 30 (e.g., the user interface 37) and acts to modify a position of the haptic device 30. In an impedance control mode, the haptic device 30 accepts position (or motion) input and yields wrench output. For example, the haptic device 30 measures, senses, and/or calculates a position (i.e., position, orientation, velocity, and/or acceleration) of the tool 50 and applies an appropriate corresponding wrench. In a hybrid control mode, the haptic device 30 utilizes both admittance and impedance control. For example, a workspace of the haptic device 30 may be divided into a first subspace in which admittance control is used and a second subspace in which impedance control is used. In a preferred embodiment, the haptic device 30 operates in the impedance control mode.

Figure 12:
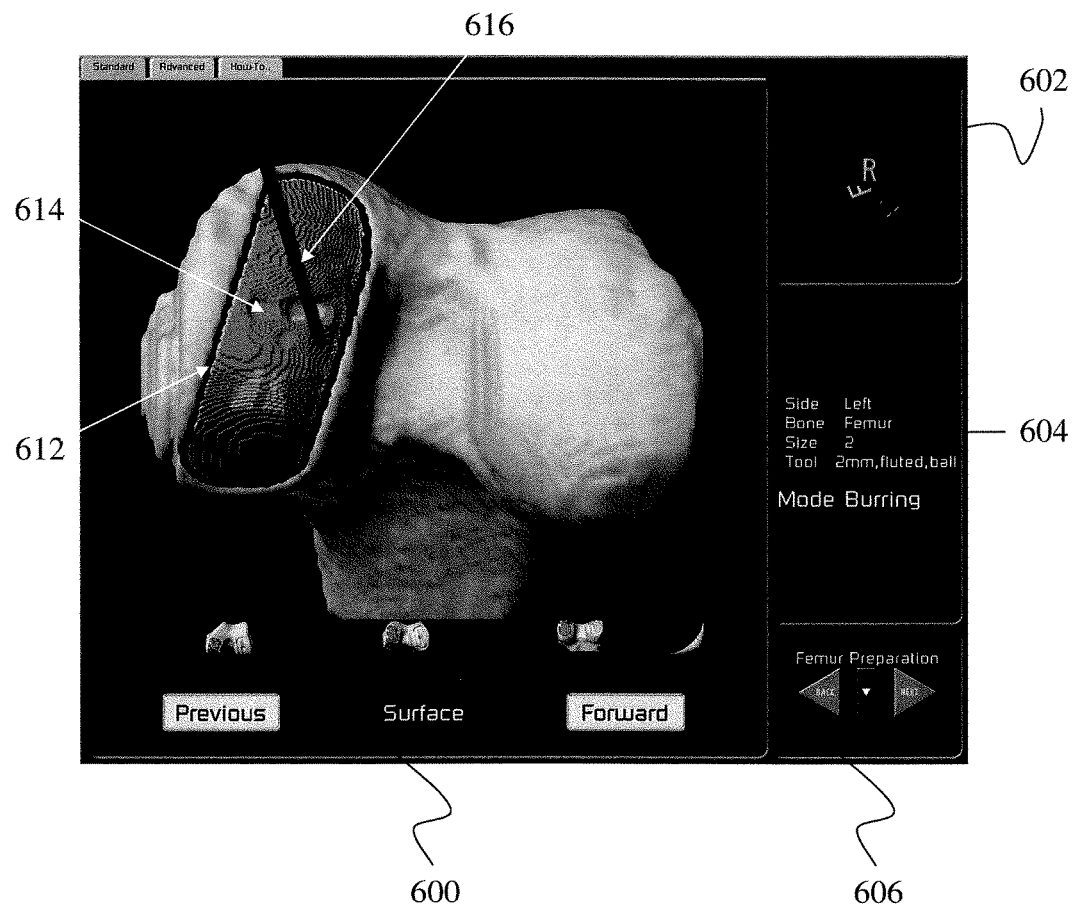
FIG. 12 shows an embodiment of a display of a CAS system according to the present invention.

During a surgical procedure, the computing system 20 guides the user through the procedure. For example, the computing system 20 may be programmed to generate a display configured to guide the user manipulating the haptic device 30 through the procedure. The display may comprise screens shown on the display device 23 that include, for example, predefined pages and/or images corresponding to specific steps of the procedure. The display may also prompt the user to perform one or more tasks. For example, the display may instruct a user to select anatomical landmarks on a representation of the anatomy (discussed below in connection with steps S3 and S4 of FIG. 13). In one embodiment, as shown in FIG. 12, the screen may include a navigation pane 600 for displaying images related to a current step of the procedure; a tracked object pane 602 for showing tracked objects in relation to one another; an information pane 604 for displaying information related to the current step of the procedure, such as, for example, measurement data, error data, status information, selection buttons, and the like; and a pane 606 for advancing to subsequent steps in the procedure and/or returning to previous steps.

Displays or screens associated with the surgical procedure may be configured to communicate visual information to the user regarding the procedure. For example, as shown in FIG. 12, the navigation pane 600 may create and display a representation of the anatomy (such as an image or representation of a bone) and a representation 616 of the surgical tool 50. For a bone preparation process, the surgical system 10 may facilitate the step of preparing the bone to receive an implant by creating a representation 612 of a portion of material to be removed from the bone, superimposing the representation 612 of the portion of material to be removed on the representation of the bone, and updating the representation 612 of the portion of material to be removed with a representation 614 of a portion of material actually removed by the tool 50 as the user manipulates the haptic device 30. To further aid the user, the surgical system 10 can update the representation of the bone and the representation 616 of the tool 50 as the bone and the tool 50 move. In one embodiment, the representation 612 of the portion of material to be removed corresponds to a portion of a virtual object associated with (or registered to) the bone. Thus, the virtual object represents the portion of material to be removed from the anatomy. For example, the virtual object may have a shape substantially corresponding to a shape of a surface of an implant to be fitted to the anatomy (e.g., in a cementless implant application). For cemented implant applications, the virtual object may have a shape that is larger than a shape of the implant to allow room for a cement mantle between the implant and the bone. The above-described bone preparation steps may be performed, for example, on a first bone (e.g., the tibia T) and then repeated for a second bone (e.g., the femur F).

In one embodiment, the portion of bone to be removed may be indicated for example, using a color that is different from a color of surrounding bone. For example, the portion of bone to be removed may be colored green while the surrounding bone is colored white. As the user removes bone with the tool 50, the computing system 20 updates the image in the navigation pane 600 so that when the tool 50 reaches a desired cutting depth, the color changes from green to white. Similarly, if the tool 50 cuts beyond the desired cutting depth, the color changes from white to red. Thus, the surgical system 10 creates a representation of a portion of material to be removed in a first color and, when a desired amount of material has been removed, creates a representation of the material removed by the haptic device 30 in a second color. If the material removed by the haptic device exceeds the desired amount of material, the surgical system 10 creates a representation of the material removed in a third color. In a preferred embodiment, a haptic object includes an array of volume elements (i.e., voxels) having a first portion corresponding to a portion of bone to be removed, a second portion corresponding to surrounding bone, and a third portion corresponding to a cutting depth that is outside a predefined cutting volume. The voxels in the first portion may be a first color (e.g., green), the voxels in the second portion may be a second color (e.g., white), and the voxels in the third portion may be a third color (e.g., red). As the tool 50 overlaps a voxel, the voxel is cleared thereby exposing an adjacent underlying voxel. Thus, if the user cuts too deeply with the tool 50, green and/or white voxels may be cleared to expose underlying red voxels. In another embodiment, the surgical system 10 may provide a visual indication of a distance between the tip of the tool 50 and a surface of a haptic object in registration with the patient as described, for example, in U.S. patent application Ser. No. 10/621,119 (Pub. No. 2004/0106916), which is hereby incorporated by reference herein in its entirety. The navigation pane 600 may also include, for example, a representation of a current position of the tool 50, a desired trajectory of the tool 50, a representation of an implant, and/the like.

In addition to communicating with the user visually, the computing system 20 may be programmed to emit audible signals (e.g., via the acoustic device). For example, in one embodiment, the computing system 20 may emit sounds (e.g., beeps) indicating that a cutting depth of the tool 50 is too shallow, approximately correct, or too deep. In another embodiment, the surgical system 10 may provide an audible indication of a distance between the tip of the tool 50 and a surface of a haptic object in registration with the patient as described, for example, in U.S. patent application Ser. No. 10/621,119 (Pub. No. US 2004/0106916), which is hereby incorporated by reference herein in its entirety. The computing system 20 may also be programmed to control the haptic device 30 to provide tactile feedback to the user, such as, for example, a vibration indicating that the tool 50 has reached or exceeded the desired cutting depth. The software of the computing system 20 may also include programs or processes that automatically prompt a user to perform certain tasks, such as, for example, segmenting an image of a diagnostic image data set, selecting points on the patient's anatomy to define a mechanical axis, touching (or "painting") points on a surface of the bone with a registration probe, entering data (e.g., implant size, burr size, etc.), and the like.

Figure 13:
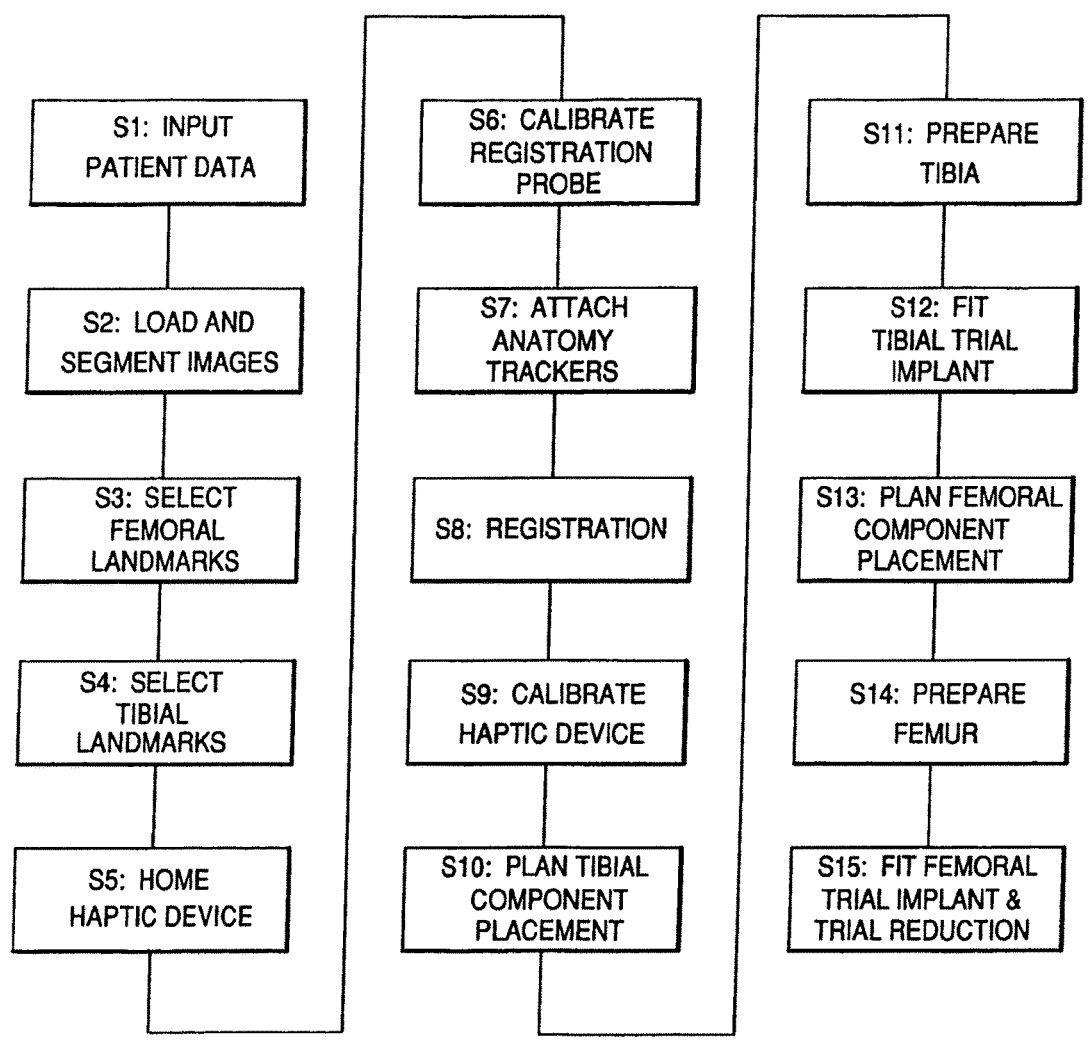
FIG. 13 is a block diagram of an embodiment of a process for a unicondylar knee replacement according to the present invention.

FIG. 13 illustrates an embodiment of a process for using the surgical system 10 for surgical planning and navigation of a unicondylar knee replacement. The process of FIG. 13 is intended as an exemplary illustration only. In other embodiments, the order of the steps of the process may be rearranged in any manner suitable for a particular surgical application. Additionally, other embodiments may include all, some, or only portions of the steps illustrated in FIG. 13 and may combine any of the steps of FIG. 13 with existing and/or later developed surgical approaches. The unicondylar knee replacement procedure detailed in the process of FIG. 13 is for a medial side of the knee. The same process may be used, however, for a lateral side of the knee. Moreover, the illustrated unicondylar procedure is exemplary only. The surgical system 10 may also be used to perform a total knee replacement procedure or other joint replacement procedure involving installation of an implant. The implant may include any implant or prosthetic device, such as, for example, a total knee implant; a unicondylar knee implant; a modular knee implant; implants for other joints including hip, shoulder, elbow, wrist, ankle, and spine; and/or any other orthopedic and/or musculoskeletal implant, including implants of conventional materials and more exotic implants, such as orthobiologics, drug delivery implants, and cell delivery implants. In one embodiment, the implant is a modular knee implant as described in U.S. patent application Ser. No. 11/312,741, filed Dec. 30, 2005, which is hereby incorporated by reference herein in its entirety.

In the embodiment of FIG. 13, steps S1 to S4 are performed preoperatively, and steps S5 to S14 are performed intraoperatively. In step S1, patient information or data may be input to the surgical system 10. In step S2, a preoperative diagnostic image (e.g., a CT data file) is loaded into the surgical system 10 and segmented. In step S3, femoral landmarks are selected. In step S4, tibial landmarks are selected. In step S5, a homing process is performed on the haptic device 30 to initialize position sensors in the arm 33 of the haptic device 30. In step S6, calibration of a registration probe is verified. In step S7, the anatomy trackers 43a and 43b are attached to the patient. In step S8, patient anatomy is registered. In step S9, the haptic device 30 is calibrated. In step S10, an initial placement of a tibial implant (e.g., a tibial component 74 as shown in FIG. 16B) is planned. A depth of the initial placement may be guided by points that are selected on a surface of the tibial plateau cartilage and transferred to a planning screen on the display device 23 using the registration computed in step S8. In step S11, the tibia T is prepared or sculpted. In step S12, a tibial trial implant is fitted to the prepared surface of the tibia T. In step S13, an initial placement of a femoral implant (e.g., a femoral component 72 as shown in FIG. 16A) is planned, for example, using points related to a position of the tibial trial implant at various flexions of the leg. In step S14, the femur F is prepared or sculpted. In step S15, a femoral trail implant is fitted to the prepared surface of the femur F. A trial reduction process is performed in which the user assesses the fit of the femoral and tibial trial implants and makes any desired adjustments (e.g., repeating implant planning and/or bone sculpting) prior to installing the femoral component 72 and the tibial component 74.

In step S1, patient information may be input to the surgical system 10. For example, the surgical system 10 may display a screen on the display device 23 requesting information about the patient. Patient information may include any relevant patient data, such as, for example, name, birth date, identification number, sex, height, and weight. Patient information may also include information related to the procedure to be performed, such as, for example, specifying the appropriate leg (e.g., left or right), specifying the portion of the joint to be replaced (medial, lateral, total), and selecting preoperative diagnostic image data files (e.g., CT data files) of the patient's anatomy. Patient information may be input to the surgical system 10 in any known manner. For example, the user may directly enter the patient information or the patient information may be downloaded into the surgical system 10 from a hospital network or electronic storage medium. Preferably, patient information is recorded when the patient's anatomy is imaged, is saved in an image data file (e.g., a CT data file), and is loaded into the surgical system 10 along with the image data file in step S2 below. The computing system 20 may also request information related to the user (e.g., name, identification number, PIN number, etc.), the surgical facility, and/or any other information useful for identification, security, or record keeping purposes. As with the patient data, user information may also be included in the image data file. As a safeguard, the computing system 20 may include a verification feature that prompts the surgeon (or other licensed medical professional) to verify patient information that has been input to the surgical system 10.

Figure 15:
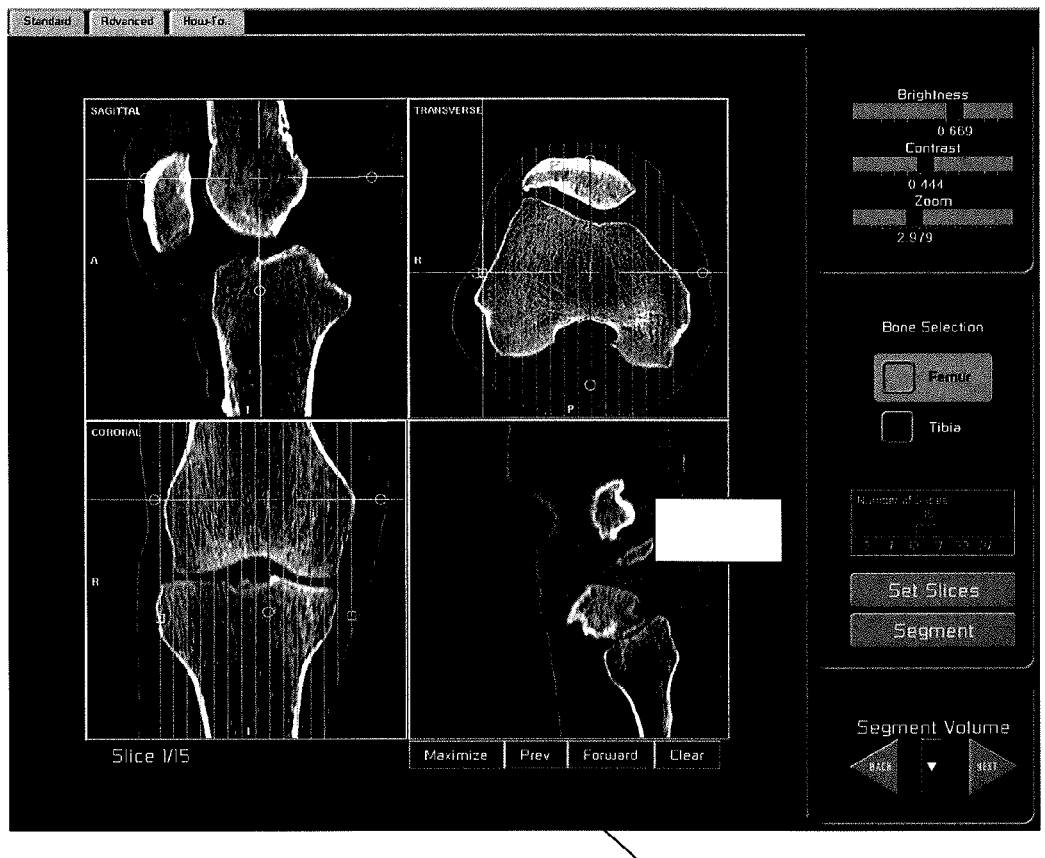
FIG. 15 is a view of an embodiment of a surgical navigation screen showing a segmentation step according to the present invention.
Figure 16:
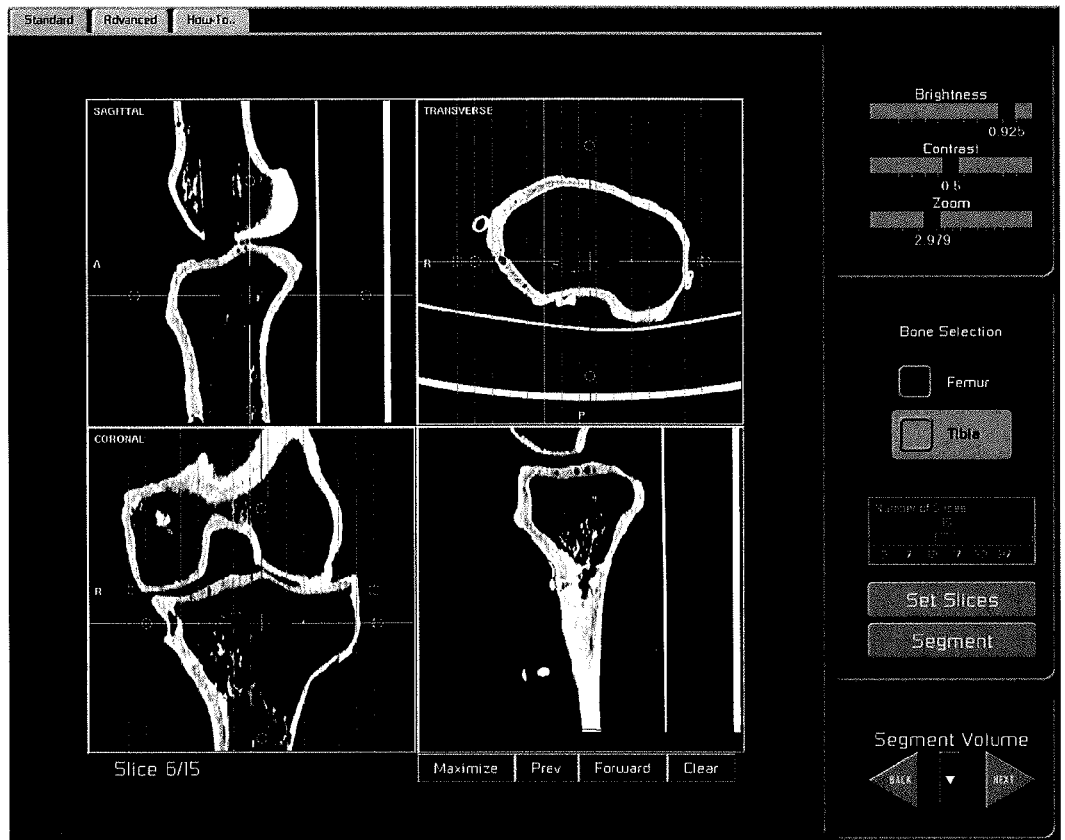
FIG. 16 is a view of an embodiment of a surgical navigation screen showing a segmentation step according to the present invention.

In step S2, a representation of the anatomy is created by loading image data files containing preoperative diagnostic images (e.g., an upper leg image, a knee image, and a lower leg image) into the surgical system 10. The diagnostic images constitute a representation of the anatomy. Additional representations of the anatomy may be generated by segmenting the images. For example, the surgical system 10 may display a screen 81a (shown in FIG. 15) to guide the user through the segmentation process for the femur F and a screen 81b (shown in FIG. 16) to guide the user through the segmentation process for the tibia T. As shown in FIGS. 15 and 16, the preoperative diagnostic images are divided into segments or slices that span the anatomy of interest. The segmentation data is used by the surgical system 10 to create a representation of the anatomy of the patient, including, for example, a representation of a first bone and a representation of a second bone. The first and second bones may be the femur F and the tibia T (or vice versa). In one embodiment, three-dimensional computer models representative of the anatomy are created based on object boundaries (e.g., at bone or cartilage surfaces) generated by the segmentation. The greater the number of segments or slices, the higher the accuracy of the model. In one embodiment, the number of slices taken across a portion of the anatomy of interest is 30 slices. In another embodiment, the number of slices taken may be in a range of 20 slices to 100 slices. The segmentation process may utilize any suitable segmentation method, such as for example, texture-based segmentation, thresholding-based interactive segmentation, region-based object segmentation, and/or polygon-based manual tracing. In one embodiment, an "edge measure" based interactive segmentation known as "livewire" is used.

Figure 17:
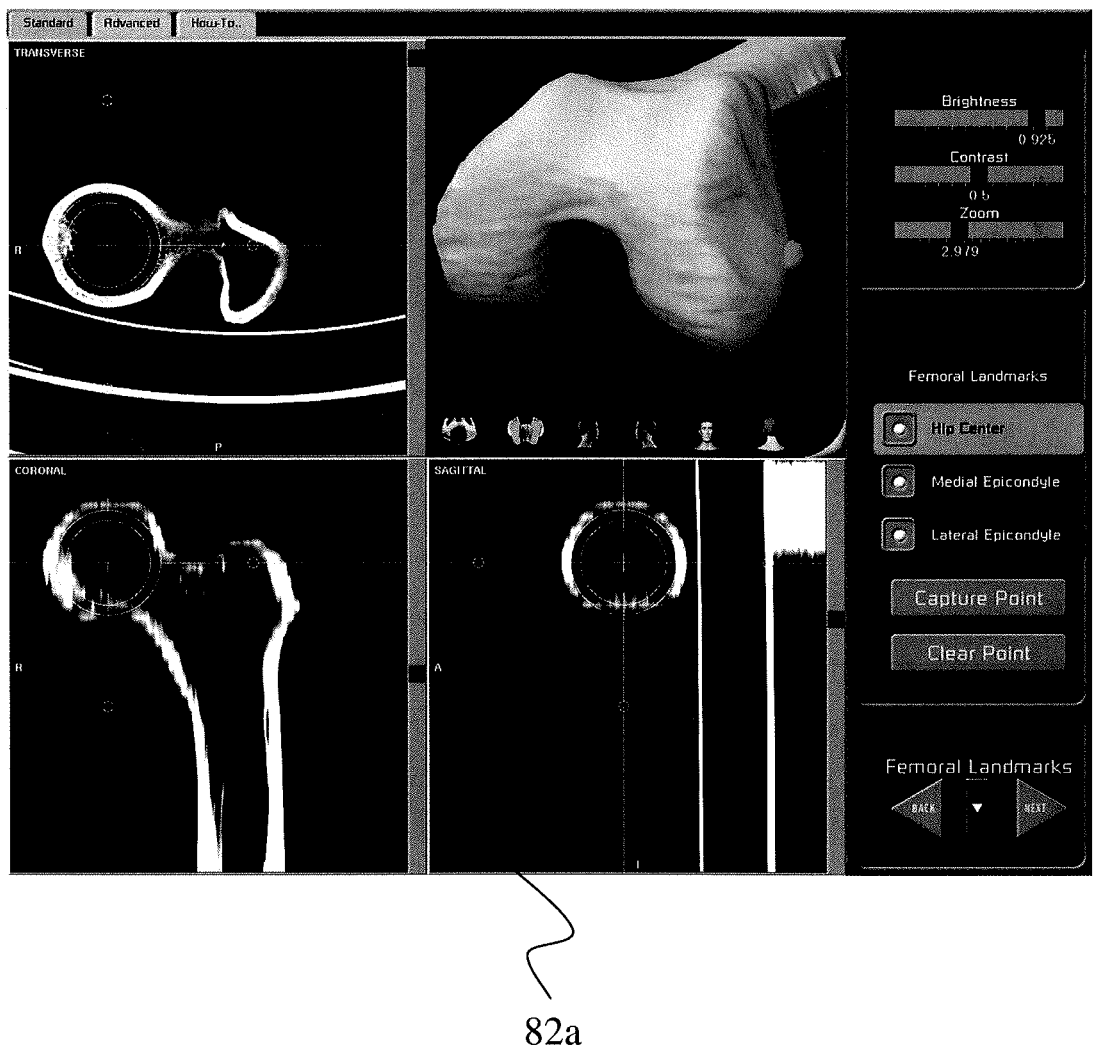
FIG. 17 is a view of an embodiment of a surgical navigation screen showing a landmark selection step according to the present invention.
Figure 18:
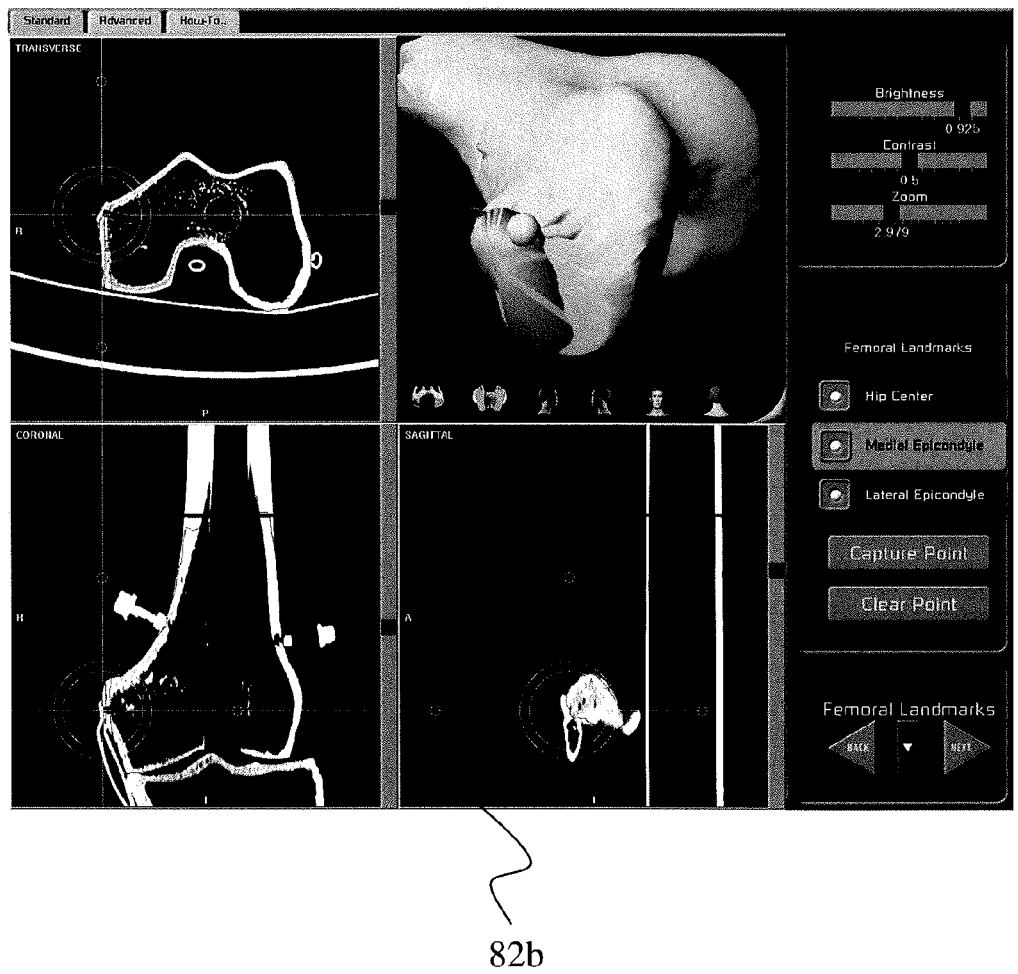
FIG. 18 is a view of an embodiment of a surgical navigation screen showing a landmark selection step according to the present invention.
Figure 19:
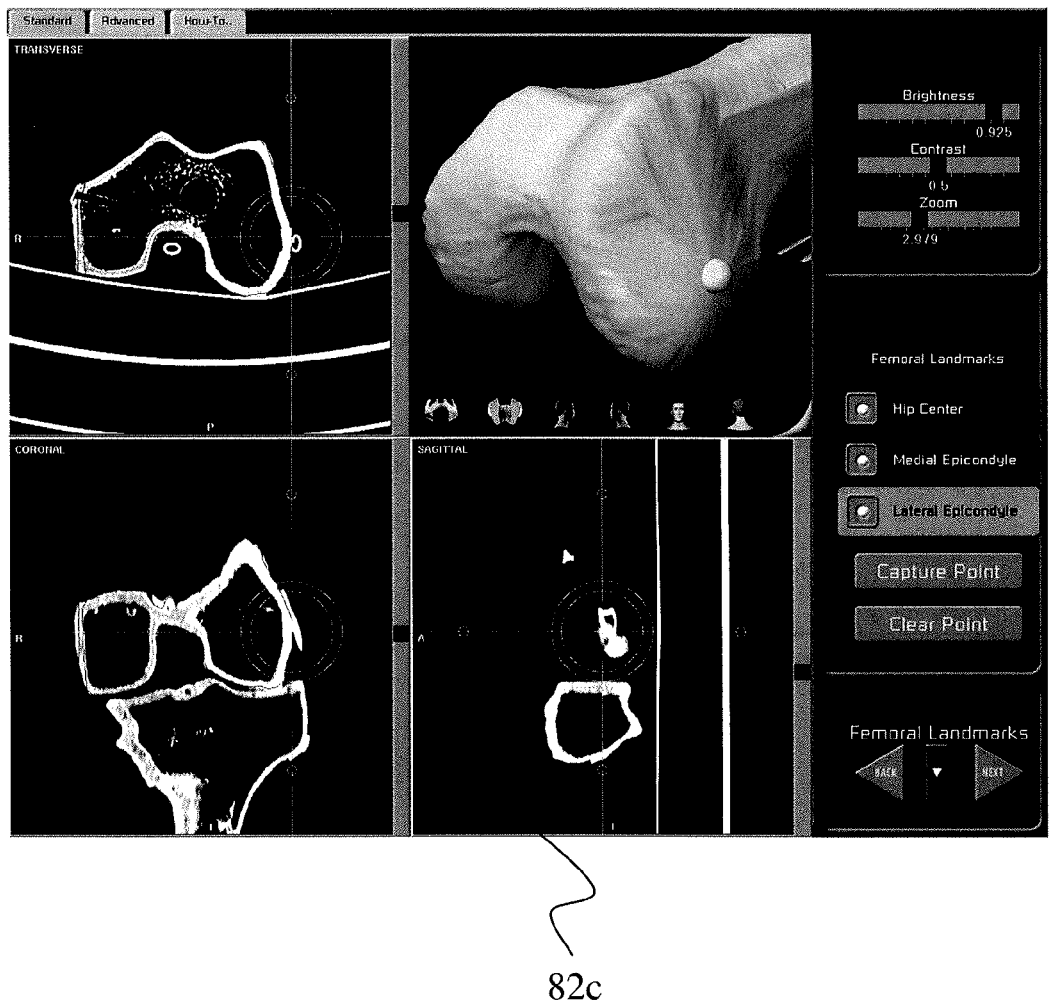
FIG. 19 is a view of an embodiment of a surgical navigation screen showing a landmark selection step according to the present invention.
Figure 20:
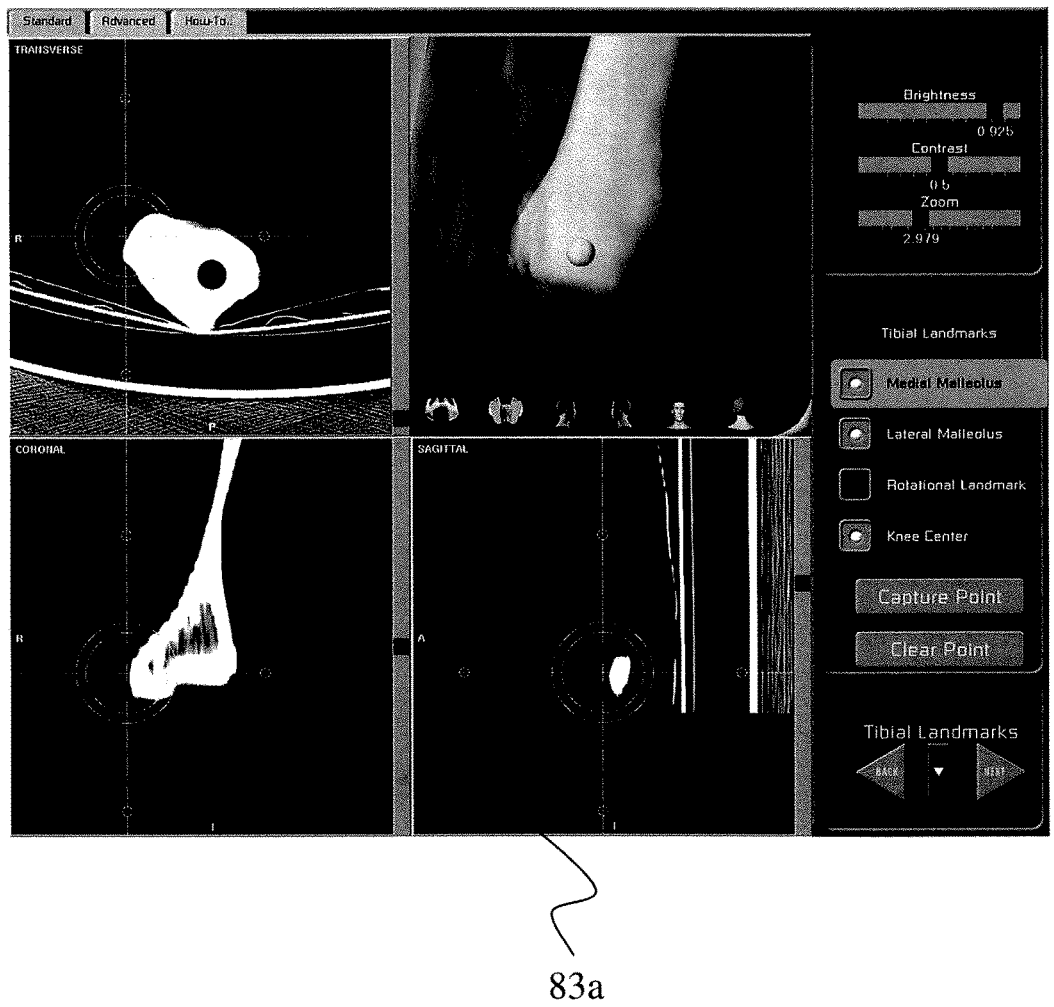
FIG. 20 is a view of an embodiment of a surgical navigation screen showing a landmark selection step according to the present invention.
Figure 21:
FIG. 21 is a view of an embodiment of a surgical navigation screen showing a landmark selection step according to the present invention.

In steps S3 and S4, the user designates landmarks on the representation of the first bone and the representation of the second bone. For example, in step S3, the user may designate femoral landmarks on an image of the femur F. The femoral landmarks are used by the surgical system 10 to associate (or register) the patient's physical anatomy with the representation of the anatomy (e.g., diagnostic images, models generated from segmentation, anatomical models, etc.). As shown in FIGS. 17 to 19, the surgical system 10 generates screens 82a, 82b, and 82c, respectively, to guide the user in specifying the femoral landmarks. For example, the surgical system 10 may direct the user to specify a hip center (FIG. 17), a medial epicondyle (FIG. 18), and a lateral epicondyle (FIG. 19). In one embodiment, the user may select the femoral landmarks on a displayed image using a mouse or touch screen. In another embodiment, the computer may be programmed to determine the location of the femoral landmarks in the images, for example, using algorithms designed to locate distinguishing features in the diagnostic images.

Figure 22:
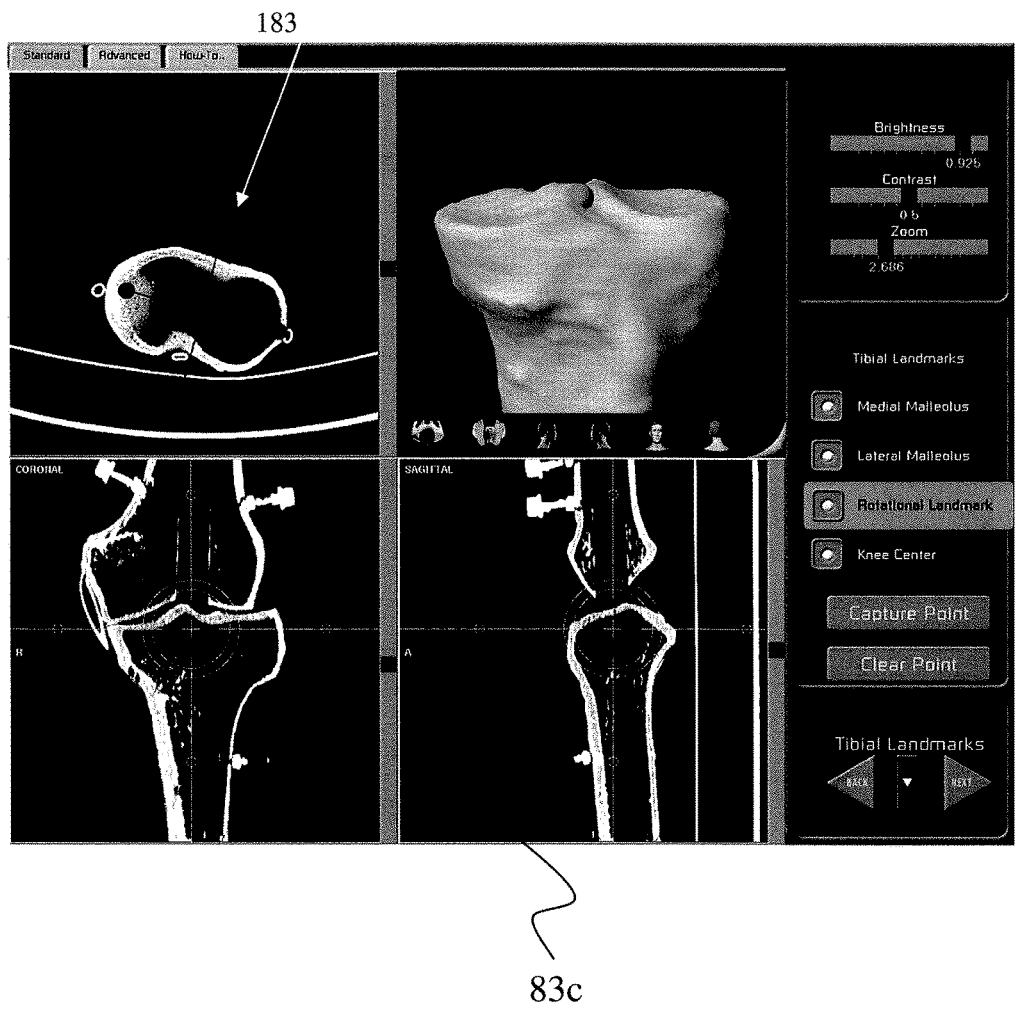
FIG. 22 is a view of an embodiment of a surgical navigation screen showing a landmark selection step according to the present invention.
Figure 23:
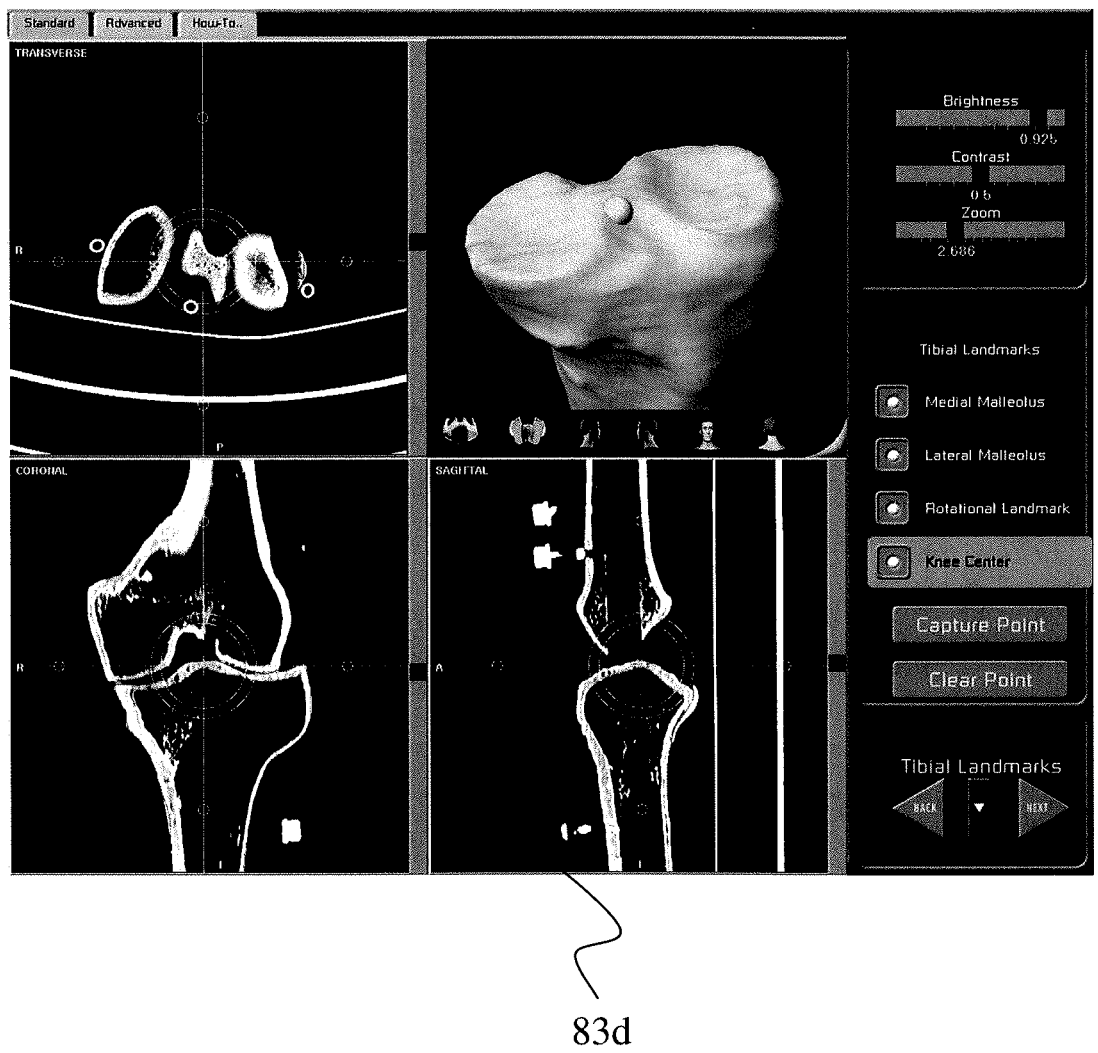
FIG. 23 is a view of an embodiment of a surgical navigation screen showing a landmark selection step according to the present invention.
Figure 35:
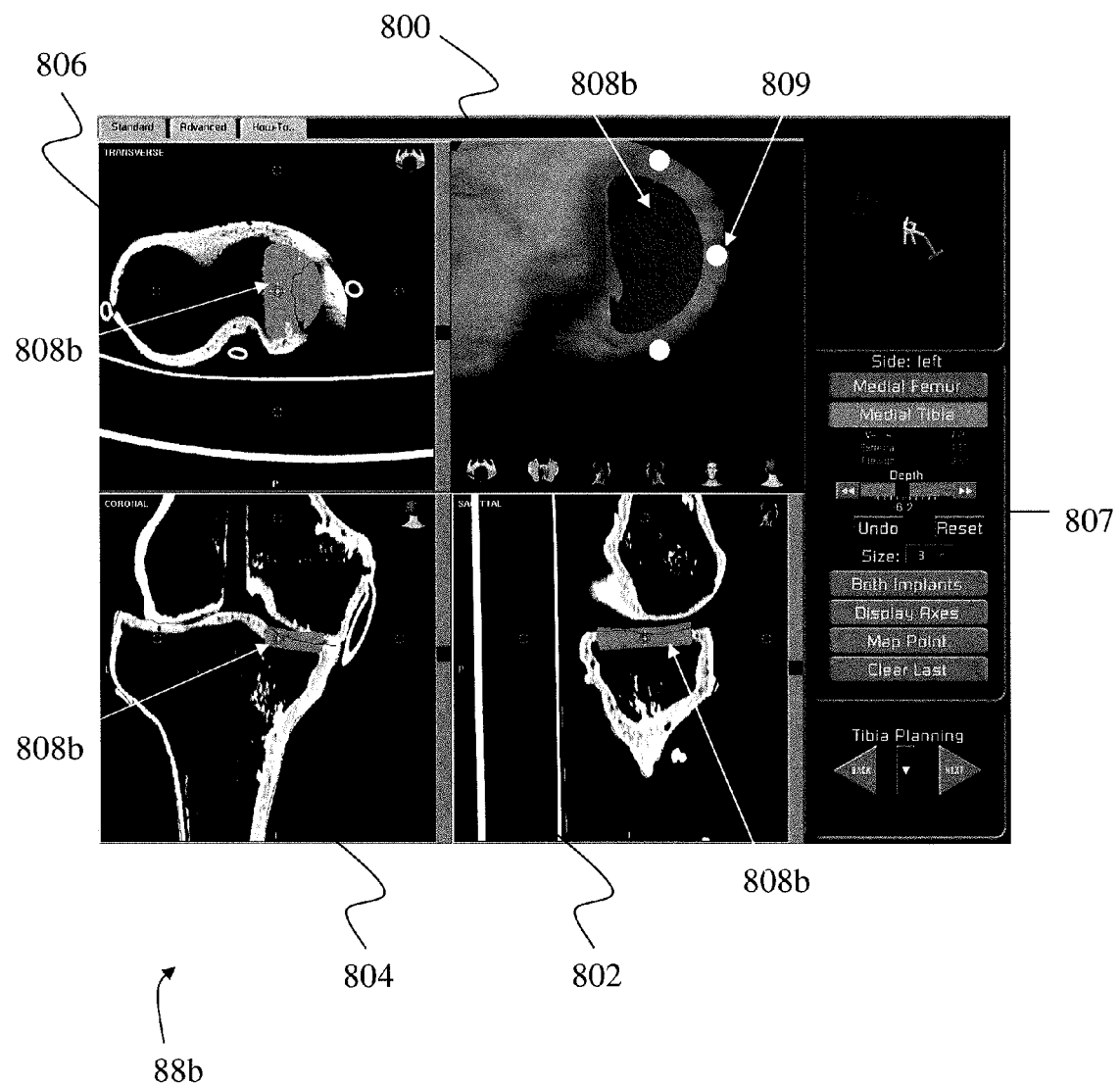
FIG. 35 is a view of an embodiment of a surgical navigation screen showing an implant placement planning step according to the present invention.

Similarly, in step S4, the user may designate tibial landmarks on an image of the tibia T. The tibial landmarks are used by the surgical system 10 to associate (or register) the patient's physical anatomy with the representation of the anatomy (e.g., diagnostic images, models generated from segmentation, anatomical models, etc.). As shown in FIGS. 20 to 23, the surgical system 10 generates screens 83a, 83b, 83c, and 83d, respectively, to guide the user in specifying the tibial landmarks. For example, the surgical system 10 may direct the user to specify a medial malleolus (FIG. 20), a lateral malleolus (FIG. 21), a rotational landmark (FIG. 22), and a knee center (FIG. 23). As shown in FIG. 22, the rotational landmark may be, for example, intersecting axes 183 that the user adjusts to be parallel to the anterior and posterior portions of the transverse view of the anatomy in the screen 83c. The rotational landmark enables the surgical system 10 to account for any rotation of the leg L in the diagnostic image (e.g., if the CT scan was taken with the leg L leaning to the side rather than in exact anterior-posterior alignment) and to adjust the transverse view so that the anterior and posterior portions are aligned (e.g., as shown in a frame 806 of FIG. 35). In one embodiment, the user may select the tibial landmarks on a displayed image using a mouse or touch screen. In another embodiment, the computer may be programmed to determine the tibial landmarks, for example, using algorithms designed to locate distinguishing features in the diagnostic images.

In step S5, a homing process initializes the position sensors (e.g., encoders) of the haptic device 30 to determine an initial pose of the arm 33. Homing may be accomplished, for example, by manipulating the arm 33 so that each joint encoder is rotated until an index marker on the encoder is read. The index marker is an absolute reference on the encoder that correlates to a known absolute position of a joint. Thus, once the index marker is read, the control system of the haptic device 30 knows that the joint is in an absolute position. As the arm 33 continues to move, subsequent positions of the joint can be calculated based on the absolute position and subsequent displacement of the encoder. The surgical system 10 may guide the user through the homing process by providing instructions regarding the positions in which the user should place the arm 33. The instructions may include, for example, images displayed on the display device 23 showing the positions into which the arm 33 should be moved.

Figure 24:
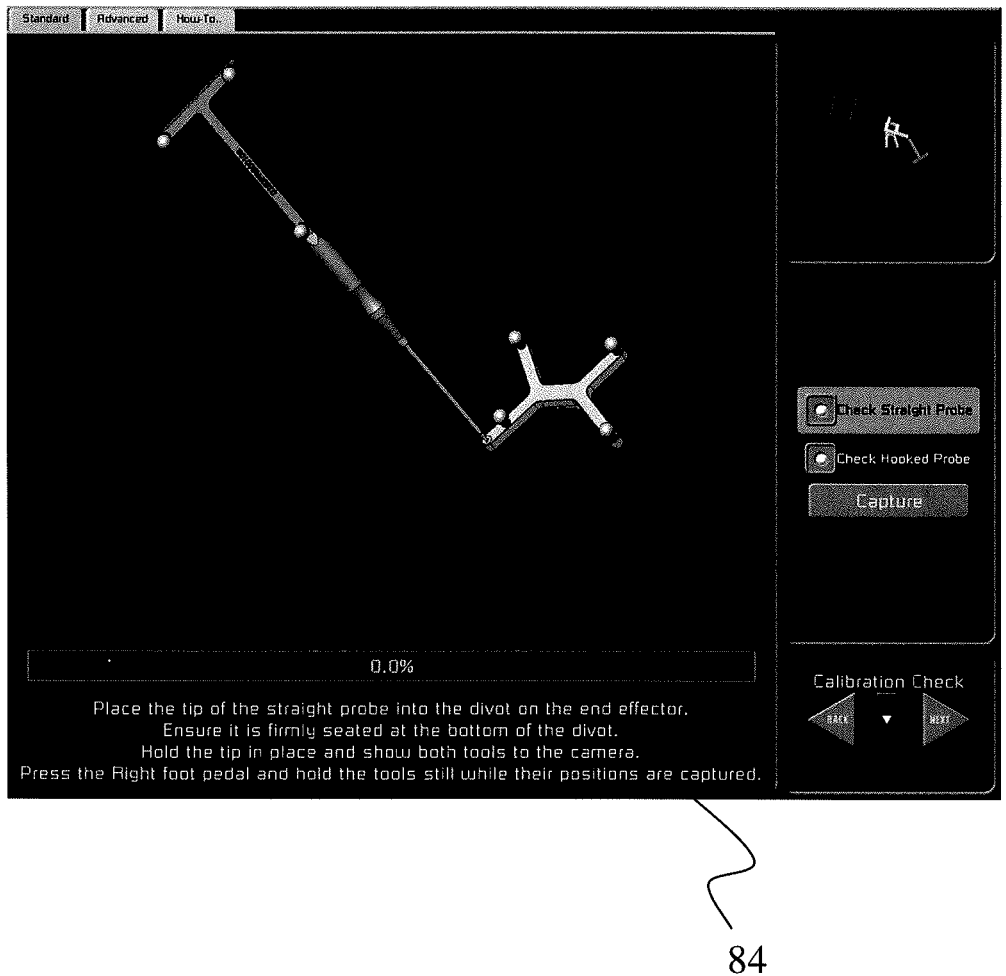
FIG. 24 is a view of an embodiment of a surgical navigation screen showing a probe calibration verification step according to the present invention.

In step S6, an instrument (e.g., a registration probe such as the instrument 150) is checked to verify that the instrument is calibrated. For example, step S6 may be used to verify that a registration probe has a proper physical configuration. As discussed above in connection with the instrument tracker 49, calibration of a probe that includes the instrument tracker 49 may be accomplished by inserting a tip of the probe into the divot 47a of the end effector tracker 47, holding the tip in place, and detecting the instrument tracker 49 and the end effector tracker 47 with the detection device 41. The detection device 41 acquires pose data, and the surgical system 10 compares an actual geometric relationship between the trackers 49 and 47 to an expected geometric relationship between the trackers 49 and 47. Deviation between the actual and expected geometric relationships indicates one or more physical parameters of the probe is out of calibration. As shown in FIG. 24, during the verification process, the surgical system 10 may display a screen 84 showing a graphical representation of the probe, the instrument tracker 49, and the end effector tracker 47 on the display device 23.

Prior to step S7, the patient arrives in the operating room. As shown in FIG. 1, the patient (only a leg L is shown) is positioned on an operating table 102, and the haptic device 30 is positioned relative to the patient so that the haptic device 30 can attain a variety of poses useful for the procedure. To achieve an appropriate level of sterility, the haptic device 30 may be sterilized in any suitable manner.

For example, the end effector 35 and the tool 50 may be sterilized using conventional sterilization processes, and other portions of the haptic device 30 may be sterilized and/or covered with a sterile covering or drape. In one embodiment, the arm 33 and the base 32 of the haptic device 30 are covered with a sterile plastic wrapping, and the platform 39 is covered with a sterile drape.

To elevate the leg L of the patient and enable the leg L to be bent at different angles, the leg L may be supported or braced in a leg holder (or support device) that can be moved into various positions. In one embodiment, the leg holder is a manually adjustable leg holder 62. As shown in FIG. 14A, the leg holder 62 includes a first portion 62a and a second portion 62b slidably disposed on a base 64 and connected at a hinge 62c. The base 64 includes a locking mechanism (not shown) for fixing the first and second portions 62a and 62b in position. The leg L may be secured on the leg holder 62 in any suitable manner, such as, for example, using one or more straps 63. Alternatively or in addition to tracking a pose of the bones of the leg L (e.g., with the anatomy trackers 43a and 43b or the mechanical tracking system 240), a pose of the leg holder 62 may be tracked (e.g., with position sensors, a non-mechanical tracking system, or a mechanical tracking system as described above). If only the leg holder 62 is tracked, the leg L should be sufficiently secured to the leg holder 62 (e.g., with the straps 63) so as to prevent relative motion between the leg L and the leg holder 62. In operation, to move the leg L, the user manipulates the leg L (or the leg holder 62) so that the first and second portions 62a and 62b slide along the base 64 and articulate about the hinge 62c. Articulation about the hinge 62c causes an angle a of the leg holder 62 to either increase or decrease. The leg holder 62 is preferably configured so that the angle a can be adjusted from approximately 0° to approximately 180°. As a result, the leg L can be moved between a fully extended position and a fully flexed position. As the leg L moves, an incision 128 (e.g., a minimally invasive incision) made on a side of the patient's knee shifts along the leg L. Shifting of the incision 128 enables the surgeon to use the same incision to insert instruments to sculpt both a proximal end of the tibia T and a distal end of the femur F. As a result, multiple incisions may be avoided, and a size of the incision 128 can be kept small.

In another embodiment, the leg holder 62 may be automated, for example, by the addition of position sensors (e.g., encoders) and a motor controlled by the computer 21 and/or the computer 31. The motor may enable the leg holder 62 to be fully automated or may simply perform a power-assist function to aid the user in positioning the leg holder 62. One advantage of fully automating the leg holder 62 is that an automated leg holder can be controlled by the surgical system 10 to autonomously move the leg L to a correct position, which spares the user the difficulty of physically maneuvering the leg L and guessing the correct position for the leg L. For example, a process for controlling an automatic leg holder (or support device) may include placing a first bone (e.g., the tibia T) and/or a second bone (e.g., the femur F) in the leg holder 62 and actuating the leg holder 62 to move the first bone and/or the second bone from a first position to a second position. The process may also include the steps of determining an actual pose of the first bone and/or the second bone (e.g., from the anatomy trackers 43a and 43b), determining a desired pose of the first bone and/or the second bone, and actuating the leg holder 62 to move the first bone and/or the second bone from the actual pose to the desired pose. As the leg holder 62 moves, the surgical system 10 can monitor the position of the first bone and/or the second bone. When the first bone and/or the second bone is in the desired pose, the process stops. In addition to tracking the position of the first and second bones, the position of the leg holder 62 may be monitored (e.g., using position sensors on the leg holder 62).

Figure 14B:
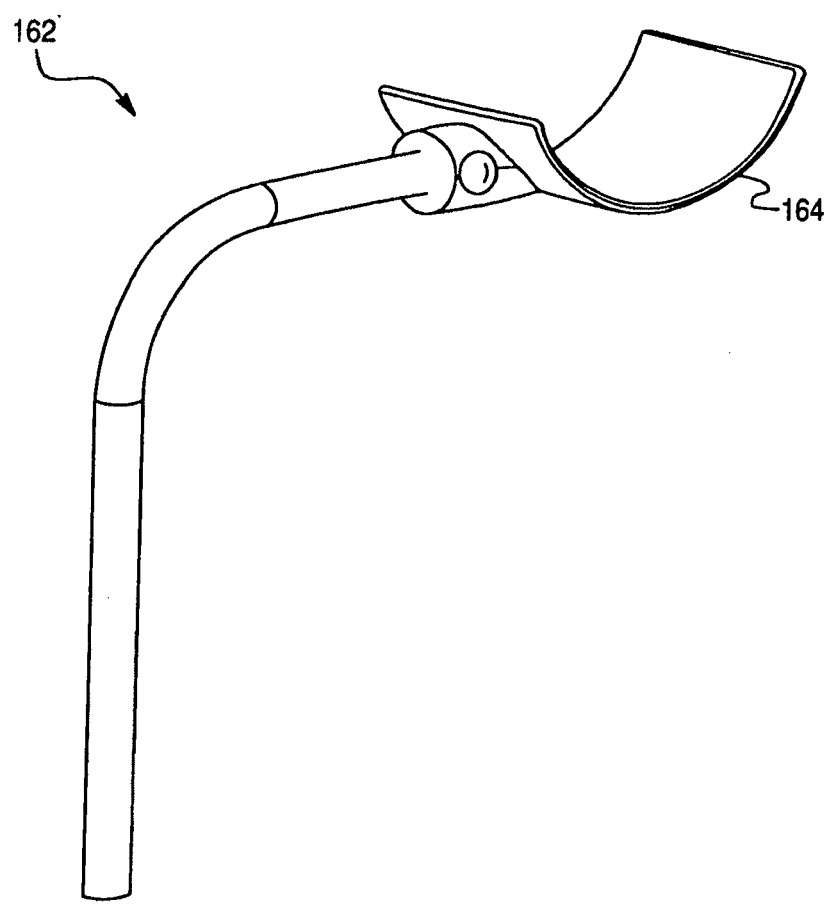
FIG. 14B shows an embodiment of a leg holder according to the present invention.

In another embodiment, as shown in FIG. 14B, the surgical system 10 includes a leg holder 162. During a surgical procedure, the leg holder 162 may be mounted on the operating table 102 or other suitable structure. An upper portion of the leg L of the patient rests in the leg holder 162 on a support 164 so that the lower portion of the leg L is freely suspended. Such an approach is advantageous because gravitational forces acting on the suspended portion of the leg L pull open the knee joint to thereby provide greater access to the joint.

Figure 25:
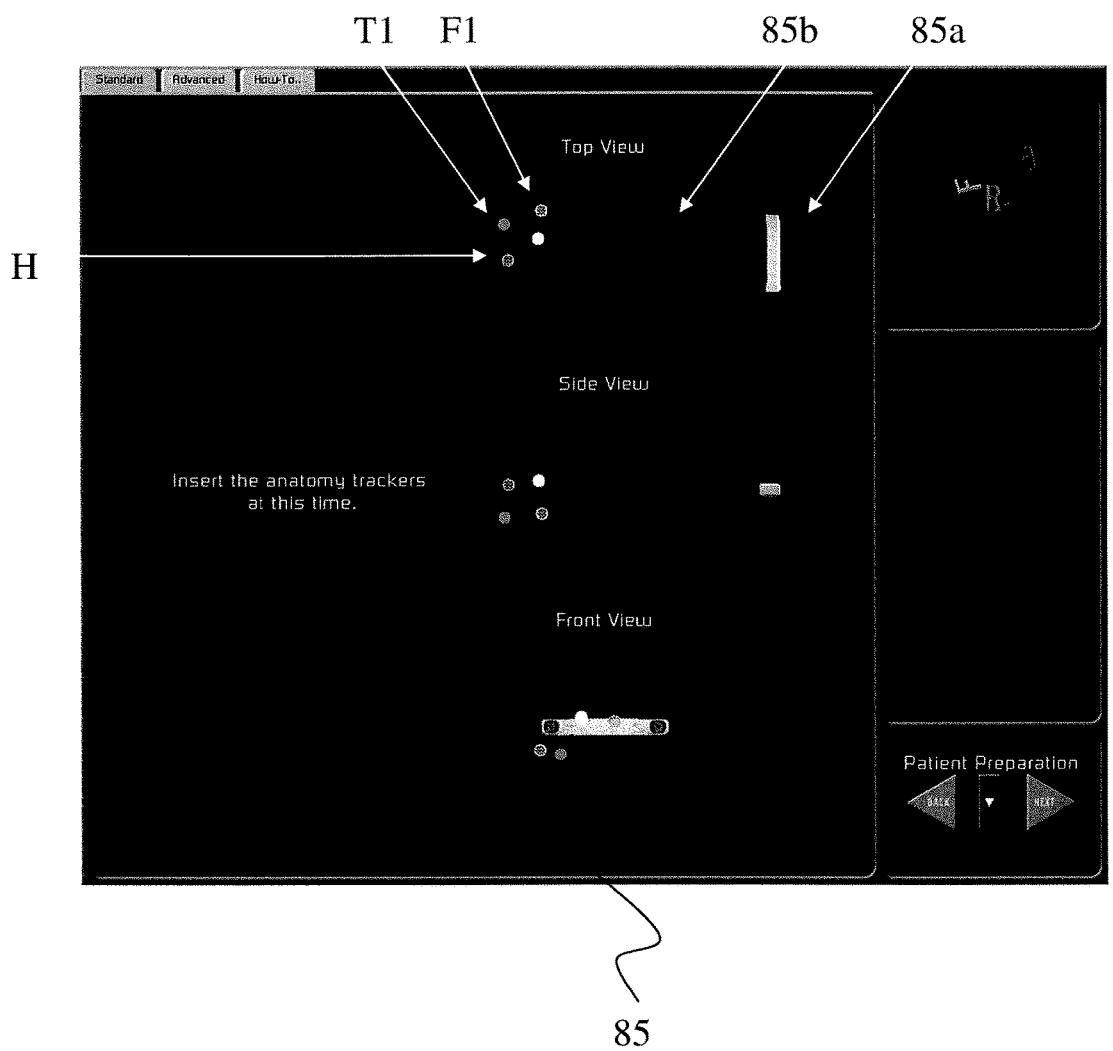
FIG. 25 is a view of an embodiment of a surgical navigation screen showing an anatomy tracker installation step according to the present invention.

In step S7, the surgical system 10 prompts the user to attach the anatomy trackers 43a and 43b to the patient. As shown in FIG. 25, the surgical system 10 may also generate a screen 85 to enable the user to optimize positioning of tracked objects with respect to the detection device 41. For example, the screen 85 may include a representation 85a of the detection device 41 and a representation 85b of a field of view of the detection device 41. The screen may also display a representation F1 of the anatomy tracker 43a, a representation T1 of the anatomy tracker 43b, a representation H of the haptic device tracker 45, and/or a representation of any other trackable element in relation to the field of view 85a of the detection device 41. In one embodiment, each of the representations F1, T1, and H is displayed in a different color to enable the user to distinguish between each of the tracked objects. In another embodiment, the representations F1, T1, and H1 may change to a different color when the tracked object is near a boundary of the field of view of the detection device 41. In this manner, the user may determine whether tracked objects are sufficiently positioned within the field of view of the detection device 41.

In one embodiment, once the anatomy trackers 43a and 43b are attached, a range of motion (ROM) of the knee joint is captured (e.g., by moving the knee joint through the ROM while tracking the anatomy trackers 43a and 43b with the tracking system 40). The captured ROM data may be used to assess relative placement of the femoral and tibial implants. For example, the ROM data augmented by registration of the physical patient to the preoperative image data allows the user to plan relative implant positions consistent with a current condition of the patient's soft tissue (e.g., based on disease state, age, weight, current ROM, etc.). In one embodiment, implant depth can be planned so that the installed implants fill the pre-existing joint gap (i.e., the gap existing preoperatively between the tibia T and the femur F) in the knee of the patient. In addition, other important parameters such as, for example, adequate contact, anterior and posterior coverage, and proper relative rotation of the implant pair can be evaluated throughout the ROM of the knee joint. In this way, comprehensive placement planning for both implants can be performed before cutting any bone. The ROM data may also be used (e.g., during the implant planning steps S10 and S13) to display relative positions of the femoral and tibial implants at extension, flexion, and various angles between extension and flexion on the display device 23.

Figure 26:
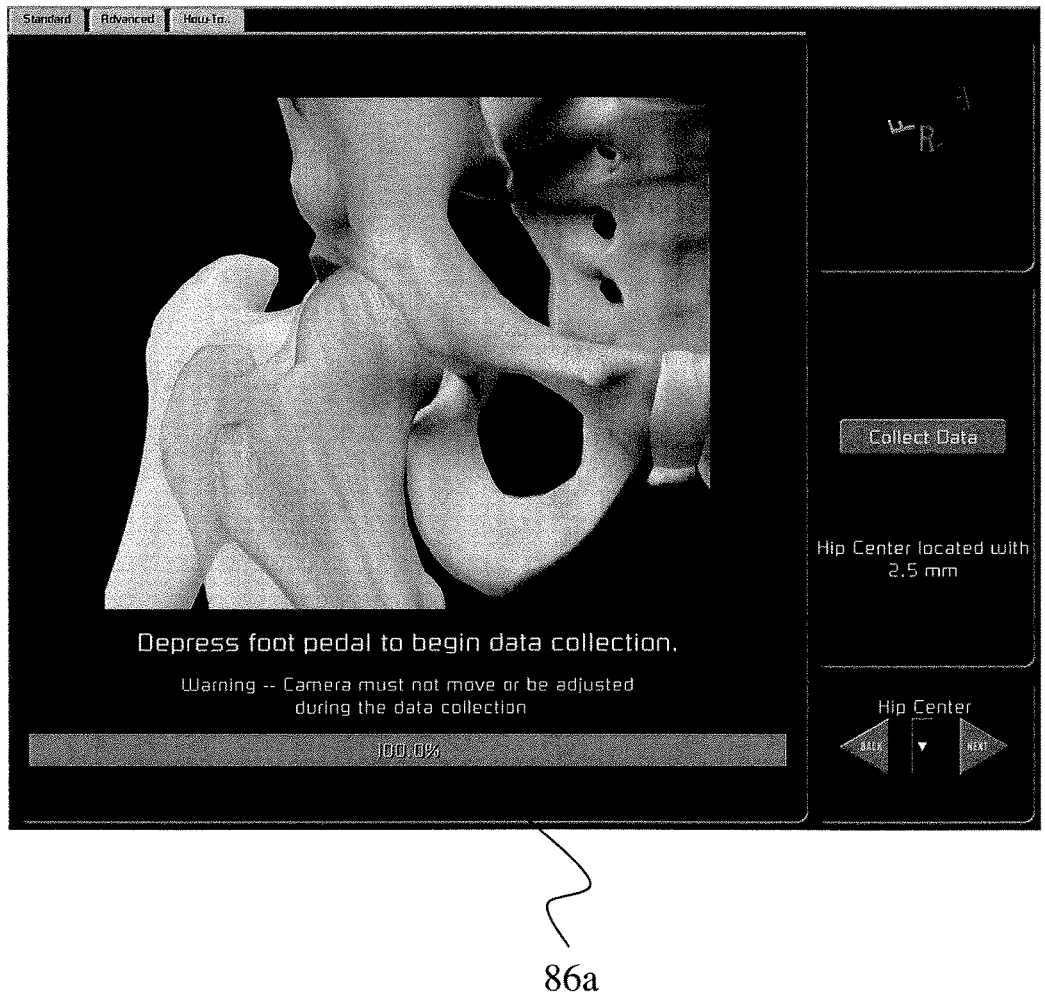
FIG. 26 is a view of an embodiment of a surgical navigation screen showing a registration step according to the present invention.
Figure 27:
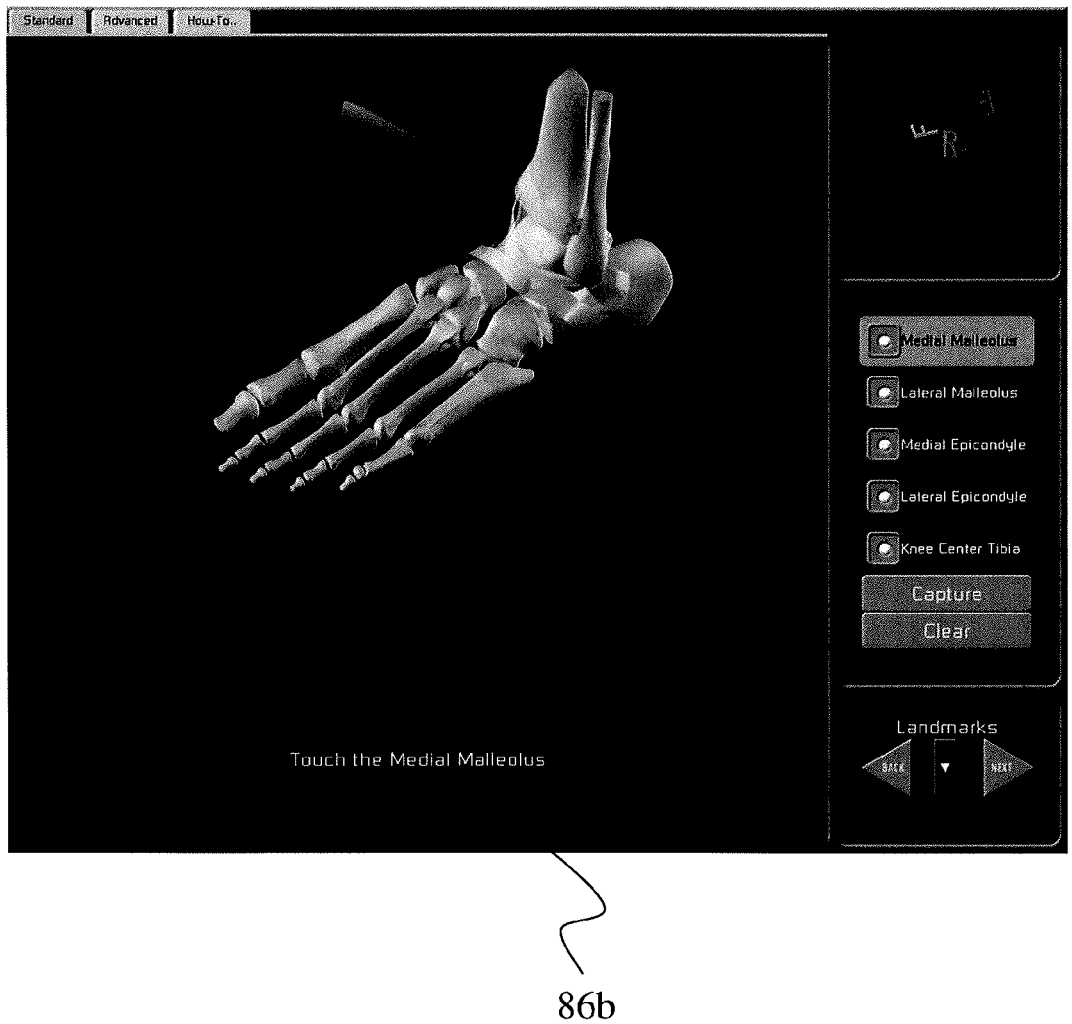
FIG. 27 is a view of an embodiment of a surgical navigation screen showing a registration step according to the present invention.
Figure 28:
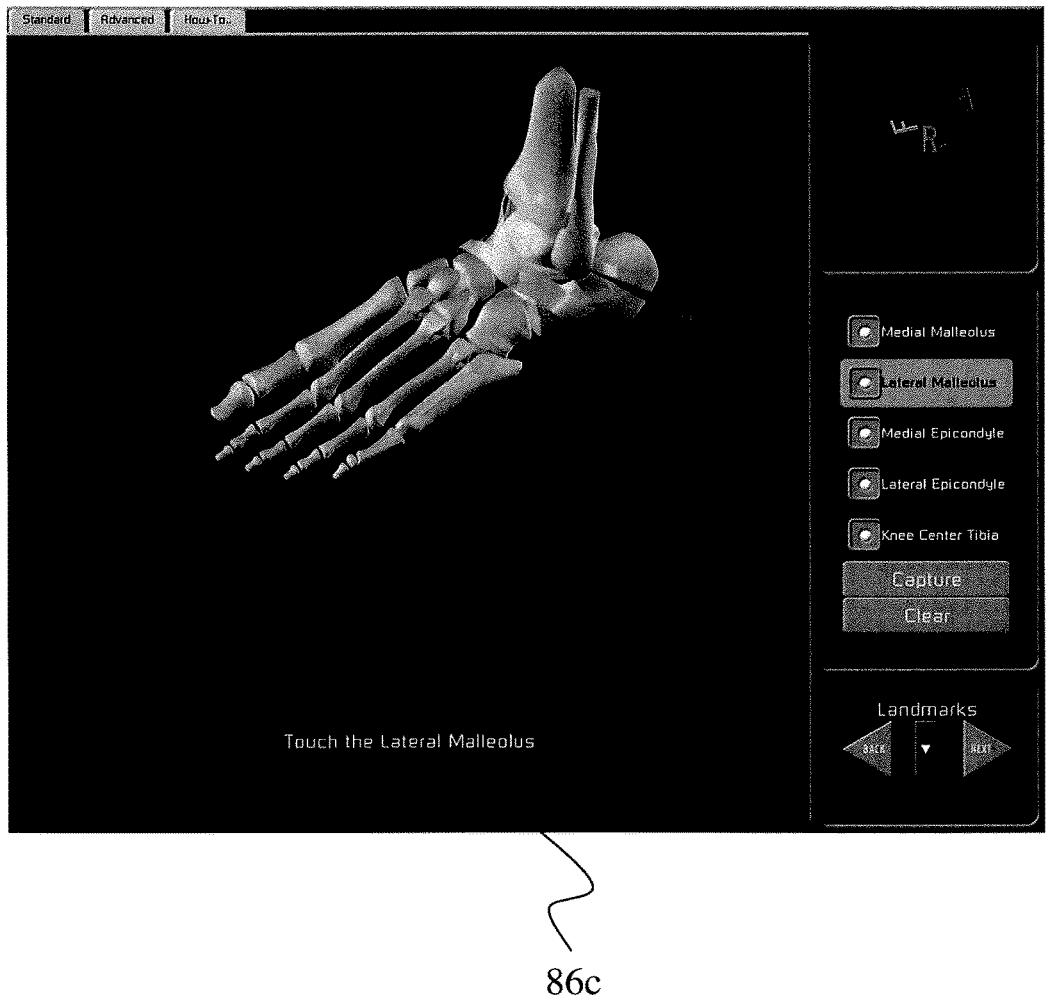
FIG. 28 is a view of an embodiment of a surgical navigation screen showing a registration step according to the present invention.
Figure 32:
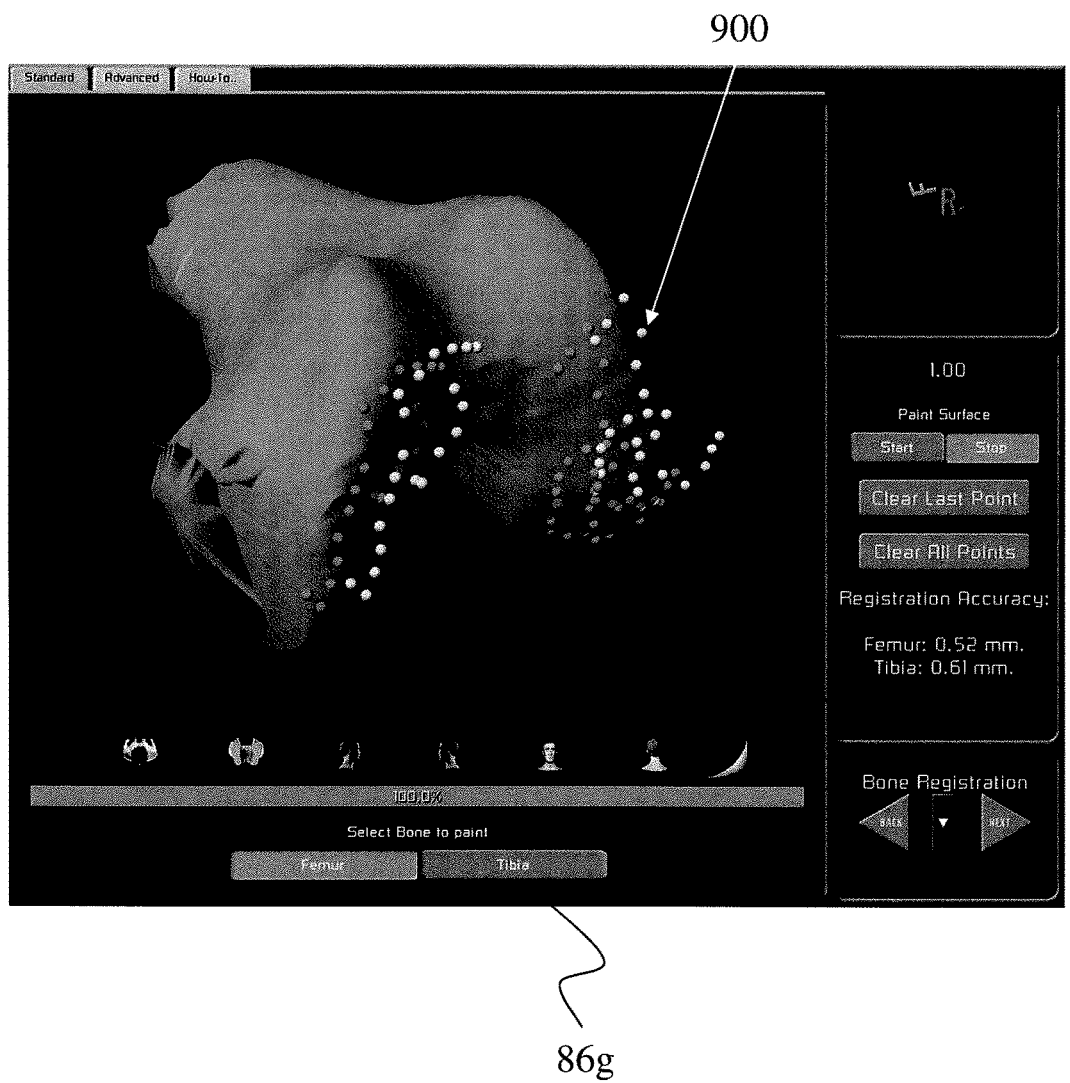
FIG. 32 is a view of an embodiment of a surgical navigation screen showing a registration step according to the present invention.
Figure 33:
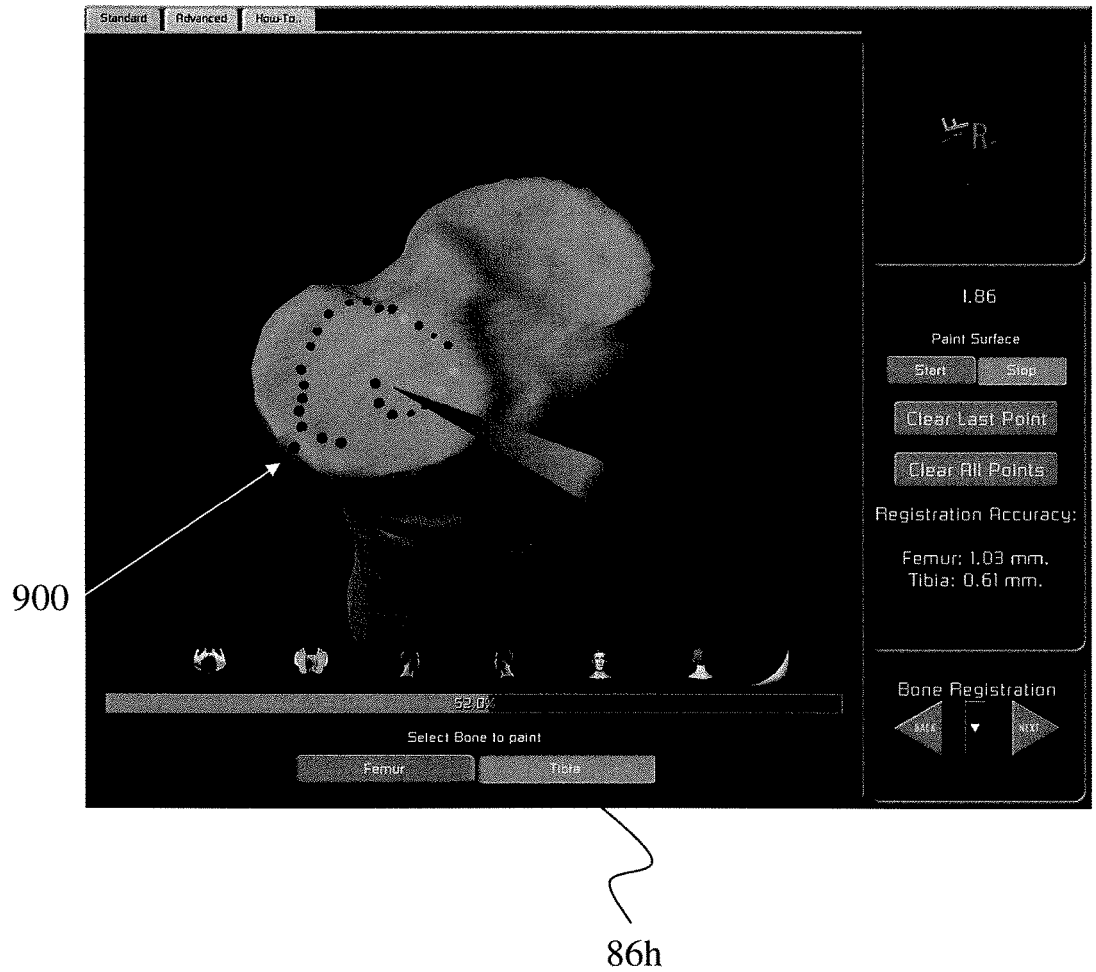
FIG. 33 is a view of an embodiment of a surgical navigation screen showing a registration step according to the present invention.

After the anatomy trackers 43a and 43b are fixed to the patient, the process proceeds to step S8 in which the patient's physical anatomy is registered to the representation of the anatomy. For example, the femur F and the tibia T of the patient may be registered in standard fashion using a paired-point/surface match approach based on the femoral and tibial landmarks specified in steps S3 and S4, respectively. The surgical system 10 generates screens to guide the user through the registration process. For example, a screen 86a (FIG. 26) instructs the user to rotate the femur F to find a center of a hip of the leg L. In one embodiment, the surgical system 10 determines the hip center by determining a center of a pivot point of the femur F based on motion of the anatomy tracker 43a during the rotation of the femur F. Screens 86b, 86c, 86d, 86e, and 86f (shown in FIGS. 27, 28, 29, 30, and 31, respectively) instruct the user to point a registration probe to various anatomical landmarks (e.g., medial malleolus, lateral malleolus, medial epicondyle, lateral epicondyle, posterior border of anterior cruciate ligament (ACL) attachment, etc.) and to select the landmarks. For example, the user may place a tip of a tracked registration probe on the relevant landmark and select the landmark with a foot pedal or other input device 25. When the user selects the landmark, the detection device 41 acquires data related to the pose of the registration probe, which is then used to calculate the location of the landmark. Based on the landmark pose data and the landmark designations in the diagnostic images (in steps S3 and S4), the surgical system 10 registers the physical anatomy to the diagnostic images by determining a correspondence between the physical landmarks on the patient and the landmarks in the diagnostic images. The accuracy of this landmark-based registration may be improved by acquiring surface data for the femur F and the tibia T. For example, the surgical system 10 may generate a screen 86g (FIG. 32) instructing the user to touch points on (or "paint") a surface of a distal end of the femur F with the registration probe. As the user paints the surface (e.g., by inserting a tip of the registration probe through the incision 128), the surgical system 10 periodically acquires a position of the probe tip and displays the acquired tip positions on the screen 86g as dots 900. For bone surfaces that are overlaid with cartilage, a sharp probe may be used to pierce the cartilage and collect points on the surface of the bone (as opposed to points on the surface of the cartilage). Similarly, the surgical system 10 generates a screen 86h (FIG. 33) and instructs the user to paint a surface of a proximal end of the tibia T with the registration probe. As the user paints the surface (e.g., by inserting the probe tip through the incision 128), the surgical system 10 periodically acquires a position of the probe tip and displays the acquired tip positions on the screen as the dots 900. As with the femur, a sharp probe may be used to pierce any cartilage so that points on the surface of the bone (as opposed to the surface of the cartilage) are collected. Additionally, a hooked probe may be used to facilitate the collection of points at a posterior margin of the tibial plateau.

Figure 34:
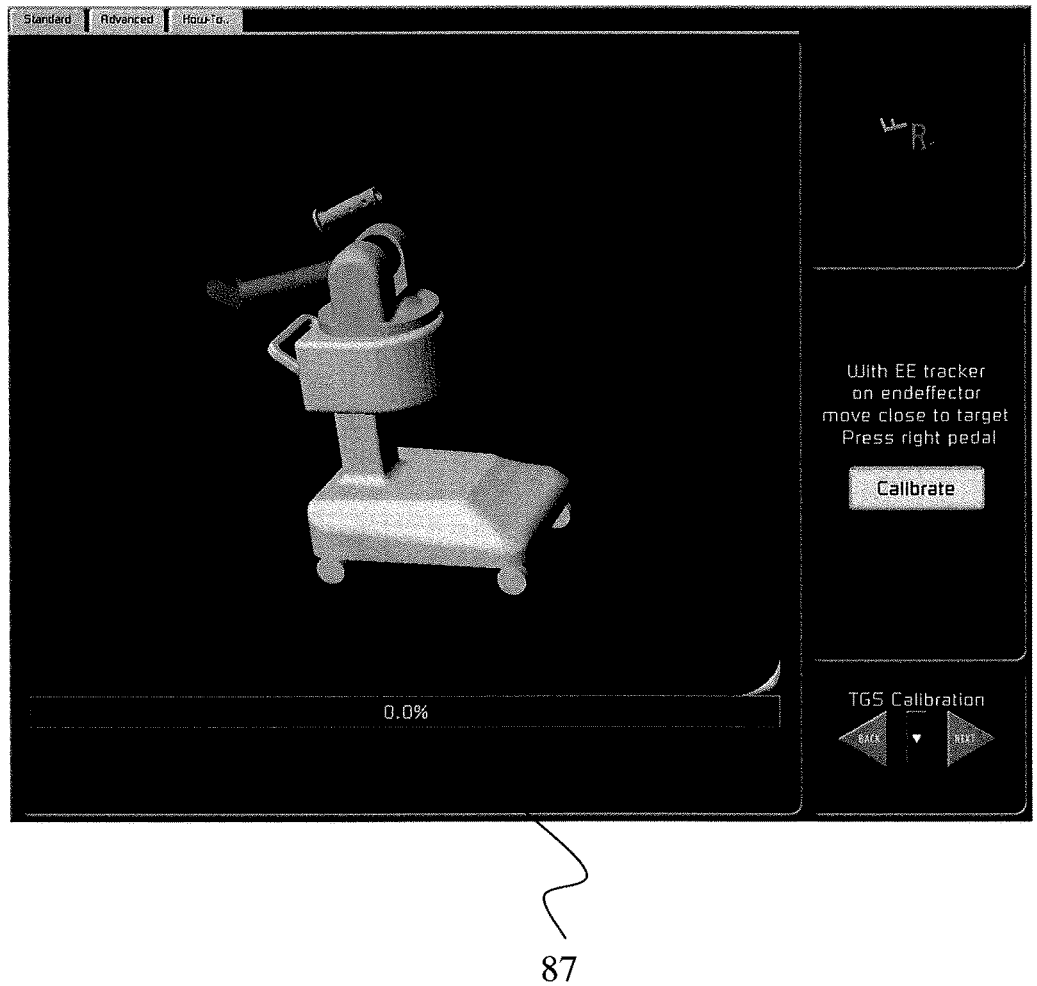
FIG. 34 is a view of an embodiment of a surgical navigation screen showing a haptic device calibration step according to the present invention.

In step S9, the haptic device 30 is calibrated to establish a geometric relationship between a coordinate frame of reference of the haptic device 30 and the haptic device tracker 45. If the haptic device tracker 45 is fixed in a permanent position on the haptic device 30, calibration is not necessary because the geometric relationship between the tracker 45 and the haptic device 30 is fixed and known (e.g., from an initial calibration during manufacture or setup). In contrast, if the tracker 45 can move relative to the haptic device 30 (e.g., if the arm 34 on which the tracker 45 is mounted is adjustable) calibration is necessary to determine the geometric relationship between the tracker 45 and the haptic device 30. The surgical system 10 initiates the calibration process by generating a screen 87 (shown in FIG. 34) instructing the user to calibrate the haptic device 30. Calibration involves securing the haptic device tracker 45 in a fixed position on the haptic device 30 and temporarily affixing the end effector tracker 47 to the end effector 35. The end effector 35 is then moved to various positions in a vicinity of the anatomy (e.g., positions above and below the knee joint, positions medial and lateral to the knee joint) while the tracking system 40 acquires pose data for the trackers 47 and 45 relative to the tracking system 40 in each of the positions. In addition, the surgical system 10 determines a pose of the end effector 35 relative to the haptic device 30 based on data from the position sensors in the arm 33. Using the acquired data, the surgical system 10 is able to calculate the geometric relationship between the haptic device tracker 45 and a coordinate frame of reference of the haptic device 30. The end effector tracker 47 may then be removed from the haptic device 30. During surgery, the surgical system 10 can determine a pose of the tool 50 based on (a) a known geometric relationship between the tool 50 and the end effector 35, (b) a pose of the end effector 35 relative to the haptic device 30 (e.g., from the position sensors in the arm 33), (c) the geometric relationship between the haptic device 30 and the haptic device tracker 45 determined during calibration, and (d) the global or gross position of the haptic device 30 (e.g., from the pose of the haptic device tracker 45 relative to the tracking system 40). The calibration process of step S9 need not be performed if the haptic device tracker 45 has not moved with respect to the haptic device 30 since the previous calibration and the previously acquired calibration data is still reliable.

In step S10, the user plans bone preparation for implanting a first implant on a first bone. In a preferred embodiment, the first bone is the tibia T, the first implant is the tibial component 74, and bone preparation is planned by selecting a location on a proximal end of the tibia T where the tibial component 74 will be installed. To facilitate implant planning, the surgical system 10 generates a screen 88b (shown in FIG. 35) that includes various views of representations of the first and second bones (i.e., the tibia T and the femur F, respectively). For example, the screen 88b may include a frame 800 showing a three-dimensional rendering, a frame 802 showing a sagittal view, a frame 804 showing a coronal view, and a frame 806 showing a transverse view. Additionally, a frame 807 may display selection buttons and data relative to implant placement and selection, such as, for example, implant size, depth, internal/external angle, varus/valgus angle, flexion angle, etc. Additionally, a mechanical axis of the femur F (e.g., an axis from the hip center or center of the femoral head to the knee center) and/or a mechanical axis of the tibia T (e.g., an axis from the knee center to the ankle center) may be displayed to aid in implant planning. The user can select and display multiple different slices or three-dimensional reconstructions of the images and can overlay a contour representing a surface of the tibia T (or the femur F) on the slice images to facilitate implant planning. In one embodiment, the surgical system 10 proposes an appropriately sized tibial implant and placement location and associates a representation (or implant model) 808b of the tibial implant with the representation of the tibia T. To visually aid the user, the surgical system 10 may also superimpose the representation 808b of the tibial implant on the representation of the tibia T. The user has the option to modify the proposed placement. For example, the user may change the size, anterior/posterior position, medial/lateral position, and rotations of the implant model 808b (e.g., by dragging or adjusting the implant model 808b with a mouse). Changes made to the implant model 808b in one of the frames causes the implant model 808b in the remaining frames to automatically update. When the user completes tibial implant planning, the surgical system 10 stores the chosen location. Implant planning may be repeated and adjusted as desired at any time during the surgical procedure, such as, for example, prior to, during, and/or after bone preparation.

The location of the tibial component 74 may be selected, for example, based on surgical judgment, to generally center the tibial component 74 on the tibial plateau, to position the tibial component 74 on hard bone to avoid subsidence over time, to position the tibial component 74 a desired distance from one or more landmarks, and/or based on a cartilage surface identified by a tracked tool. In one embodiment, the user selects a location for the tibial component 74 by moving the implant model 808b (shown in FIG. 35) to the general implantation area. Using the transverse view in the frame 806, the user adjusts the implant model 808b rotationally so that the flat side of the implant model 808b is approximately parallel to the anterior cruciate ligament (ACL) and posterior cruciate ligament (PCL) attachment points. An internal/external angle dimension (designated "External") in the frame 807 displays the resulting internal/external angle. Using the coronal view in the frame 804, the user adjusts the varus/valgus angle of the implant model 808b. A varus/valgus angle (designated "Varus") dimension in the frame 807 displays the resulting varus/valgus angle. Using the sagittal view in the frame 802, the user adjusts the posterior slope of the implant model 808b. A flexion angle dimension (designated "Flexion") in the frame 807 displays the resulting flexion angle. The user may adjust a depth of the implant model 808b in the tibia T by adjusting a depth bar (designated "Depth") in the frame 807. The user may also change the size of the implant model 808b using a size selection box (designated "Size") in the frame 807. To aid in positioning of the implant model 808b, the user may display the mechanical axes using a button (designated "Display Axes") in the frame 807. The frame 807 may also include a button (designated "Both Implants") to enable the user to display the tibial and femoral implants on the screen 88b simultaneously.

In a preferred embodiment, soft tissue in the joint gap of the knee is taken into account when selecting a placement for the tibial component 74. For example, the first implant (i.e., the tibial component 74) may be planned so that a top surface of the tibial component 74 is aligned with a top surface of cartilage in the joint gap. Such an approach advantageously preserves the natural configuration of the joint space which may improve implant performance and longevity. In this embodiment, a height of a cartilage surface above the first bone (i.e., the tibia T) is detected, a representation of the first bone and a representation of the height of the cartilage surface are created, and bone preparation for implanting the first implant on the first bone is based at least in part on the detected height of the cartilage surface. For example, the top surface of the cartilage may be detected (or mapped) by placing a tip of a tracked probe at a point on the top surface of the cartilage and selecting the point with a button (designated "Map Point") in the frame 807. The representation of the height of the cartilage surface may include a numerical representation (e.g., a distance from the first bone to the cartilage surface) and/or a visual representation (e.g., mapped points may be displayed as points 809 in the frame 800). Several cartilage points may be mapped (e.g., an anterior point, a posterior point, a medial point, etc.). The user aligns at least a portion of the representation of the first implant (i.e., the implant model 808b) with the representation of the height of the cartilage surface (i.e., the points 809), for example, by adjusting the depth of the implant model 808b so that the upper edges of the implant model 808b align with the mapped cartilage points 809. In this embodiment, therefore, the surgical system 10 associates the representation of the first implant with the representation of the first bone based at least in part on a detected location of cartilage in a region of the first bone. In this manner, the depth of the tibial component may be selected based on a thickness of the cartilage on the tibial plateau. Thus, the surgical system 10 enables the user to determine a placement of the tibial component 74 that aligns the top surface of the tibial component 74 with the top surface of the cartilage prior to any bone cutting.

If desired, in step S10, the user may also preoperatively plan an initial placement of the second implant (i.e., the femoral component 72) on the second bone (i.e., the femur F). Preferably, however, step 10 includes only preoperative planning of the first implant (i.e., the tibial component 74). Femoral planning is delayed until after sculpting (step S11) and trialing (step S12) of the tibia T so that the size, internal/external rotation, and medial/lateral position of the femoral component can be determined based on the position of the tibial trial in relation to the femur F.

Steps S11 to S15 encompass the bone preparation process. In step S11, the first bone (e.g., the tibia T) is prepared to receive the first implant (e.g., the tibial component 74) by manipulating the tool 50 to sculpt the first bone. In step S12, a trial implant is fitted to the prepared feature on the first bone. In step S13, an initial placement of the second implant (e.g., the femoral component) is planned (or a previously planned placement of the second implant may be revisited and adjusted). In step S14, the second bone (e.g., the femur F) is prepared to receive the second implant after preparation of the first bone. In step S15, a trial implant is fitted to the prepared features on the second bone.

Bone preparation (or sculpting) may be accomplished, for example, using a spherical burr to sculpt or contour the bone so that a shape of the bone substantially conforms to a shape of a mating surface of the implant. The user has the option to prepare either the femur F or the tibia T first. In a preferred embodiment, the tibia T is prepared first (step S11), and the tibial trail implant is fitted to the prepared surface of the tibia T (step S12). Placement of the femoral component 72 is then planned (step S13) followed by preparation of the femur F (step S14). Such an approach is advantageous because the user can plan placement of the femoral component 72 based on a physical relationship between the tibial trial implant and the femur F at various flexions of the leg. Additionally, prior to sculpting the tibia T and the femur F, a portion (e.g., a 3 mm thick section) of the medial posterior condyle of the femur F is preferably removed with a sagittal saw. Removing this portion of the posterior condyle reduces the likelihood of bone impingement of the posterior condyle on the tibial component 74 and provides additional workspace in the knee joint.

Throughout surgical procedure, the surgical system 10 monitors movement of the anatomy to detect movement of the anatomy and makes appropriate adjustments to the programs running on the computer 21 and/or the computer 31. In one embodiment, the surgical system 10 adjusts the representation of the anatomy in response to the detected movement. For example, the surgical system 10 adjusts the representation of the first bone (i.e., the tibia T) in response to movement of the first bone and adjusts the representation of the second bone (i.e., the femur F) in response to movement of the second bone. The surgical system 10 can also adjust a virtual object associated with the anatomy in response to the detected movement of the anatomy. For example, the virtual object may include a virtual boundary that comprises a representation of an implant (e.g., the virtual boundary may correspond to a shape of a surface of the implant). When bone preparation is planned, the surgical system 10 associates the representation of the implant with the representation of the bone on which the implant is to be implanted. During the surgical procedure, the surgical system 10 adjusts the virtual boundary in response to movement of the bone.

Figure 36:
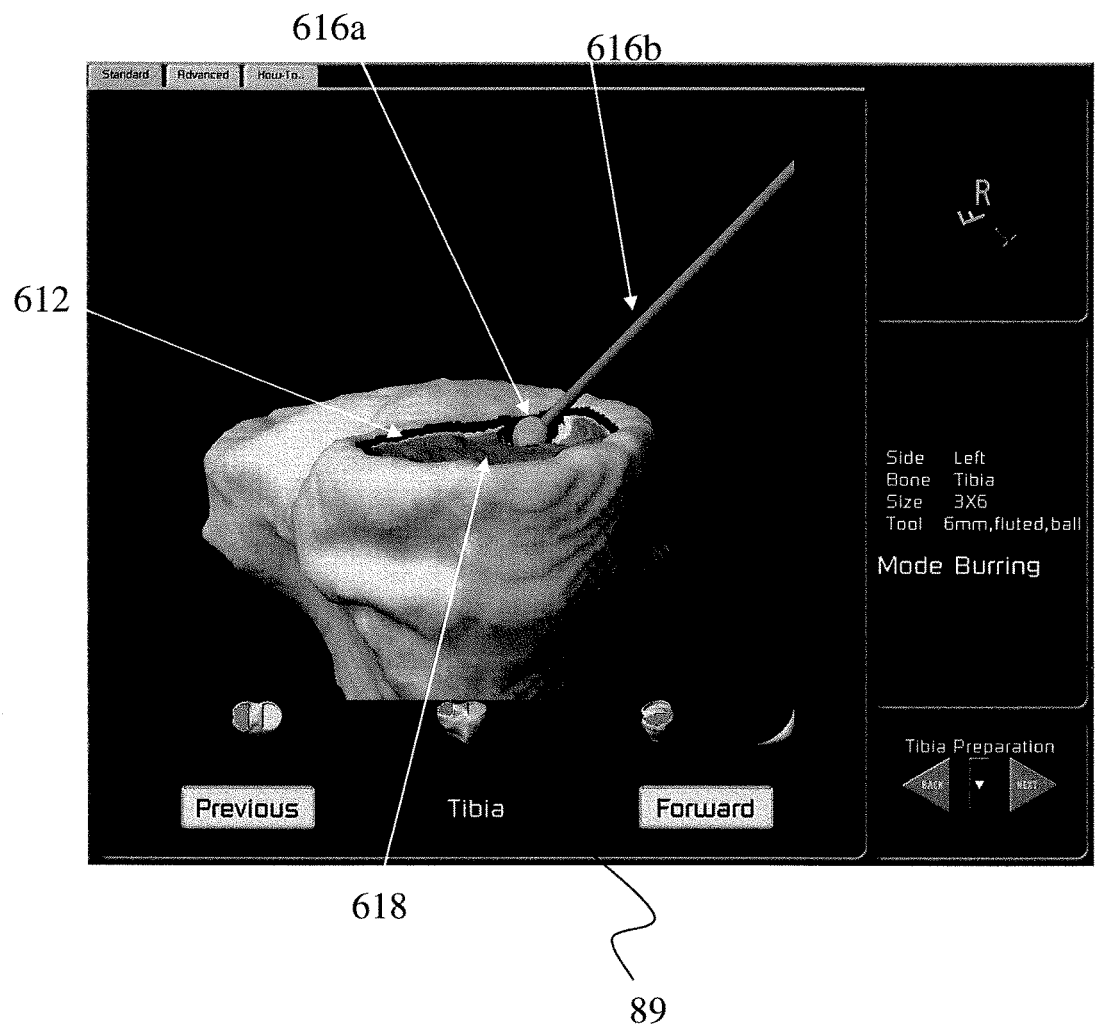
FIG. 36 is a view of an embodiment of a surgical navigation screen showing a bone preparation step according to the present invention.

In step S11, the first bone is prepared to receive the first implant by manipulating the tool 50 to sculpt the first bone. In one embodiment, the tibia T is prepared by forming the medial tibial pocket feature on the proximal end of the tibia T. Upon installation of the tibial component 74, the medial tibial pocket feature will mate with the surface 74a of the tibial component 74 (shown in FIG. 10B). As shown in FIG. 36, the surgical system 10 displays a screen 89 showing a graphical representation of the tibia T including, for example, an representation 612 of a portion 618 of bone to be removed and a graphical representation of the tool 50 showing a tool tip 616a and a tool shaft 616b. The screen 89 may optionally display a position of the opposite bone (i.e., the second bone or femur F) to guide the user in avoiding accidental cutting of a surface of the opposite bone. The portion 618 of bone to be removed is preferably colored a different color from the surrounding bone. For example, the portion 618 may be colored green while the surrounding bone is colored white. The haptic device 30 enters the approach mode in which a haptic object (e.g., the haptic object 300 shown in FIG. 1, the haptic object 310 shown in FIG. 9) in the form of an approach path assists the user in guiding the tip of the tool 50 through the incision 128 and toward the feature of interest on the patient (i.e., the portion of bone on the patient's anatomy corresponding to the portion 618 graphically represented on the screen 89). In the approach mode, the tool 50 is disabled to avoid accidental cutting as the tool 50 traverses the incision 128 and is navigated to the feature of interest. The surgical system 10 automatically places the haptic device 30 in the haptic (or burring) mode, for example, when the tip of the tool 50 approaches a predefined point related to the feature of interest. When the haptic device 30 is placed in the haptic mode, the surgical system 10 also initiates an occlusion detection algorithm.

The occlusion detection algorithm is a safety feature that turns off power to the tool 50 if either the haptic device tracker 45 or one of the anatomy trackers 43a or 43b is at any time occluded while the haptic device 30 is in the haptic (or burring) mode. If an occluded state is detected, the occlusion detection algorithm may also cause a warning message to be displayed on the display device 23, an audible alarm to sound, and/or power to the tool 50 to be shut off. Thus, the occlusion detection algorithm prevents the tool 50 from damaging the anatomy when the tracking system 40 is not able to track a relative position of the tool 50 and the anatomy. For example, in one embodiment, if the occlusion detection algorithm detects an occluded state, the surgical system 10 determines whether the tool 50 is touching a haptic boundary of a haptic object. If the tool 50 is not in contact with a haptic boundary, the occlusion detection algorithm places the haptic device 30 in the free mode so that the tool 50 will move with the patient and, if necessary, can be withdrawn from the patient. When the occluded state ends (e.g., when an occluded tracker again becomes visible), the surgical system 10 places the haptic device 30 in the approach mode so that the user may resume the procedure. In contrast, if the surgical system 10 determines that the tool 50 is touching the haptic boundary during the occluded state, the occlusion detection algorithms waits for a predetermined period of time (e.g., 1 second) to see if the occluded tracker becomes visible. If the haptic device tracker 45 and the anatomy trackers 43a and 43b all become visible within the predetermined period of time, the haptic (or burring) mode is resumed. Otherwise, the haptic device 30 is placed in the free mode so that the tool 50 will move with the patient and, if necessary, can be withdrawn from the patient. As before, when the occluded state ends (e.g., when an occluded tracker again becomes visible), the surgical system 10 places the haptic device 30 in the approach mode so that the user may resume the procedure.

Figure 37:
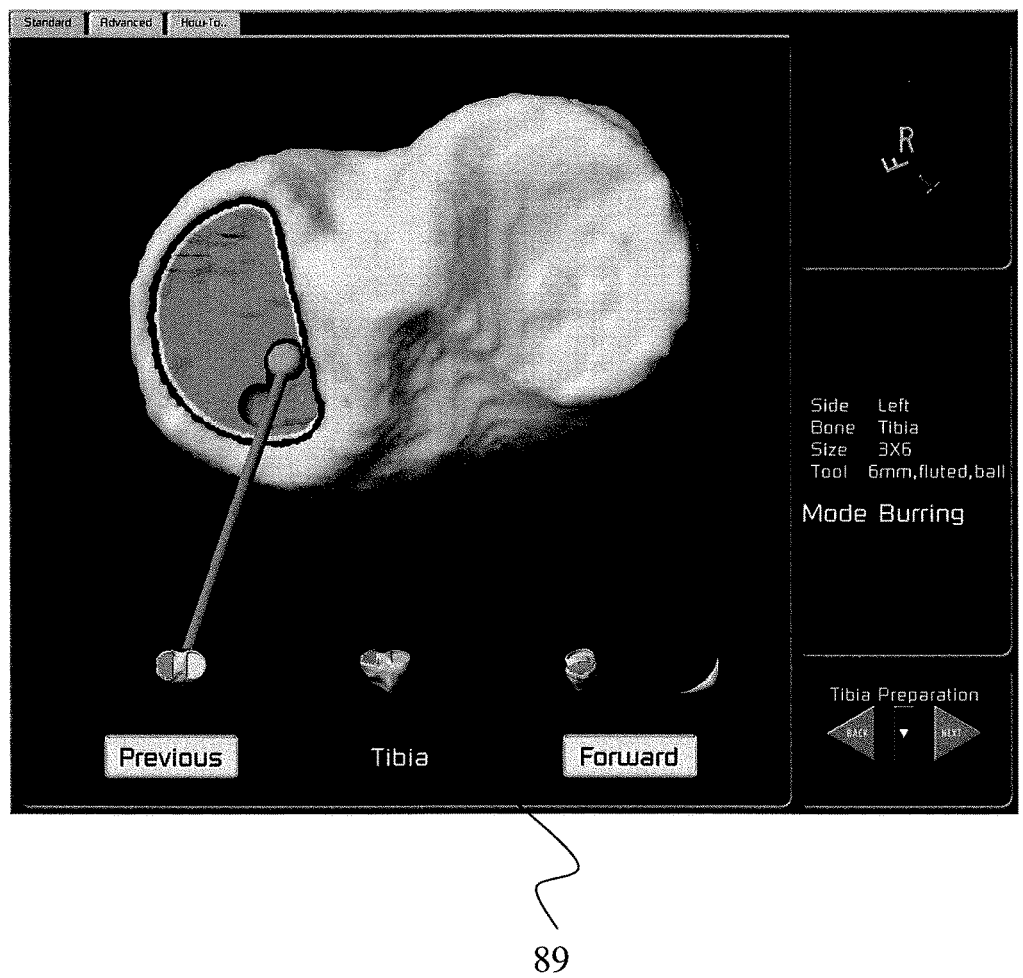
FIG. 37 is a view of an embodiment of a surgical navigation screen showing a bone preparation step according to the present invention.

Once the haptic device 30 enters the haptic mode, the user may proceed with bone sculpting. To sculpt the bone, the user manipulates the haptic device 30 by moving a portion of the haptic device 30 (e.g., the tool 50) in a region of the anatomy (e.g., the bone). As best seen in FIG. 37, as the user removes material from the bone with the tool 50, the surgical system 10 updates the image of the tibia T on the screen 89 to show a depth to which bone has been removed. During the bone removal process, the haptic device 30 imparts force feedback to the user, for example, based on a haptic object (e.g., the haptic object 206 in FIG. 9) having a shape and volume corresponding to the portion 618 of bone to be removed. For the medial tibial surface feature, a boundary of the haptic object may substantially correspond, for example, to the surface 74a (shown in FIG. 10b) of the tibial component 74 that will mate with the sculpted surface of the tibia T. The force feedback encourages the user to keep the tip of the tool 50 within the boundaries of the haptic object. For example, the force feedback may constrain the tool 50 against penetrating at least a portion of the haptic object, such as a virtual boundary. Although the haptic object is virtual and the tool 50 moves in physical space, the surgical system 10 associates the anatomy, the haptic object, and the haptic device 30 with the representation of the anatomy. Thus, the haptic object and the tool 50 are both in registration with the physical anatomy of the patient. As a result, the virtual haptic object is able to bound or constrain movement of the physical tool 50.

In addition to haptically guiding the user in the bone sculpting process, the surgical system 10 may also provide visual feedback to the user. For example, when the tool 50 reaches a desired cutting depth in a particular location of the portion 618, the color of the particular location may change from green to white to indicate that no more bone should be removed from that location. Similarly, if the tool 50 cuts beyond the desired cutting depth, the color of the particular location may change from white to red to alert the user that the cut is too deep. To further reduce the possibility of damage to healthy tissue, the surgical system 10 may also be programmed to disable power to the tool 50 should the user cut too deeply. When sculpting of the medial tibial pocket feature is complete, the user may signal (e.g., using a foot pedal or other input device 25) that he is ready to proceed to forming the next feature or that he wishes to withdraw the tool 50. The tool 50 may be withdrawn at any time during the sculpting process even if the feature is not complete. For example, the user may wish to withdraw the tool 50 to replace the tool tip, irrigate the surgical site, perform a trail reduction, revisit implant planning, address a problem that has arisen, or the like. If the user signals that he wants to withdraw the tool 50, the occlusion detection algorithm is halted and the haptic device 30 is placed in the free mode to enable withdrawal of the tool 50.

Step S12 is a trial reduction process in which the first implant (i.e., the tibial component 74) or a trial implant (e.g., a tibial trial) is fitted to the first bone (i.e., the prepared medial tibial pocket feature on the tibia T). The user assesses the fit of the tibial component or the tibial trial and may make any desired adjustments, such as, for example, repeating implant planning and/or bone sculpting to achieve an improved fit.

Figure 38:
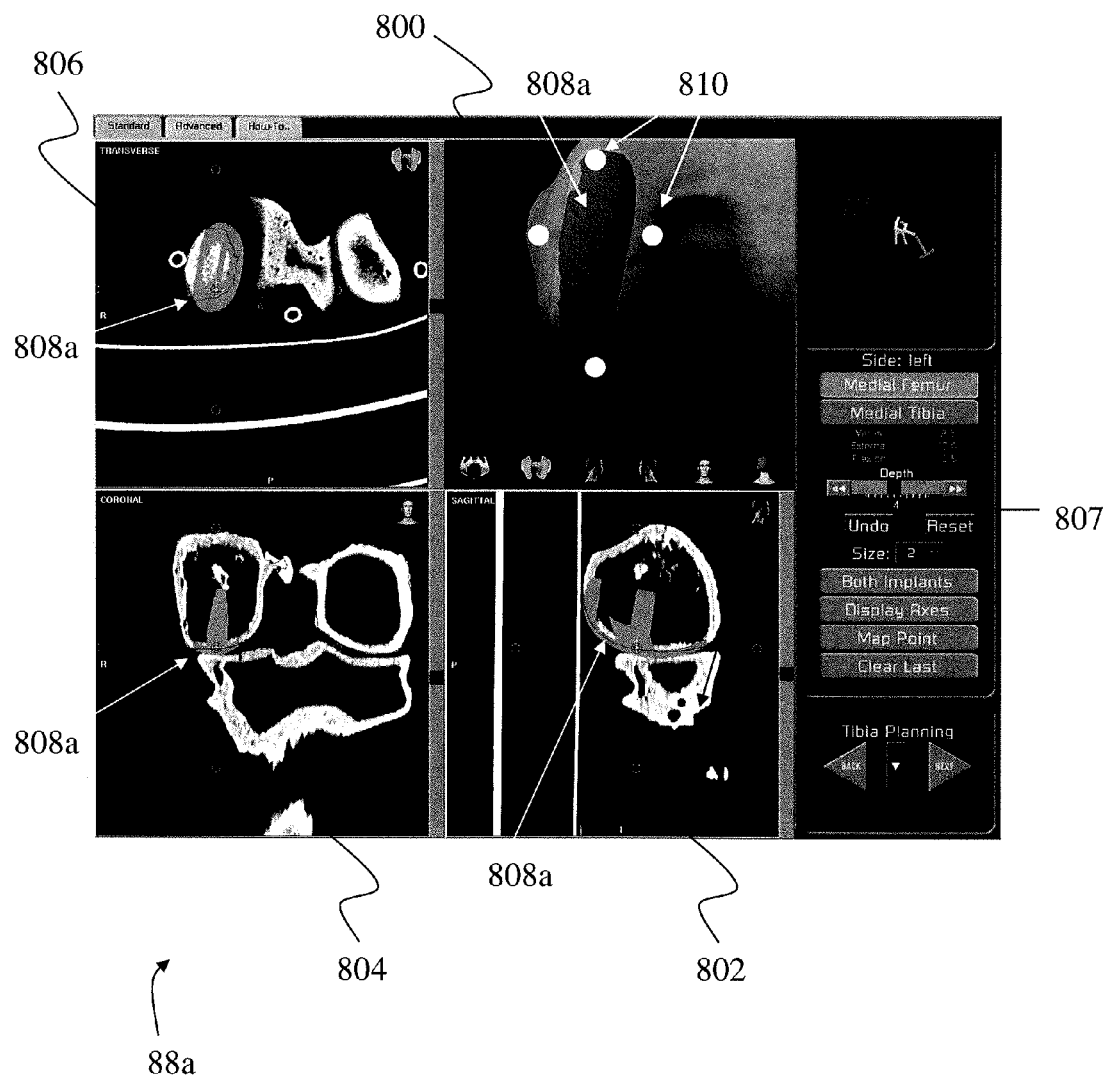
FIG. 38 is a view of an embodiment of a surgical navigation screen showing an implant placement planning step according to the present invention.

In step S13, the user plans bone preparation for implanting a second implant on a second bone after preparing the first bone. In a preferred embodiment, the second bone is the femur F, the second implant is the femoral component 72, and bone preparation is planned by selecting a location on a distal end of the femur F where the femoral component 72 will be installed. If the femoral component 72 has been previously planned (e.g., in step S10), the prior placement may be revisited and adjusted if desired. As in step S10, the surgical system 10 facilitates implant planning by generating a screen 88a (shown in FIG. 38). The screen 88a is similar to the screen 88b (shown in FIG. 35) used for planning of the tibial component 74 except the frames 800, 802, 804, 806, and 807 include images, data, and selection buttons relevant to placement of the femoral component 72, including a representation (or implant model) 808b of the second implant (i.e., the femoral component 72).

The location of the femoral component 72 may be determined, for example, relative to the position of pre-existing implants and surrounding structures. These points may be mapped using a tracked tool in the same manner as the cartilage points in step S10 above. The mapped points may include points on anatomic structures in the joint (e.g., bone, nerves, soft tissue, etc.) and/or points on pre-existing implants in the joint (e.g., edges, corners, surfaces, verification features, divots, grooves, centerline markings, etc.). The pre-existing implants may include, for example, the first implant (i.e., the tibial component 74), a trial implant (e.g., the tibial trial), and/or an existing implant from a prior surgery. The points may be selected with the leg L at various angles from full extension to full flexion. For example, points may be mapped with the leg L in full extension, at 90°, and in full flexion. In one embodiment, the knee joint is moved to a first position (e.g., one of flexion and extension), the user identifies a first point corresponding to a first location in the joint when the joint is in the first position, the knee joint is moved to a second position (e.g., the other of flexion and extension), and the user identifies a second point corresponding to a second location in the joint when the joint is in the second position. The surgical system 10 displays the first and second points in the frame 800 on the screen 88a as points 810. The points 810 aid the user in visualizing placement of the second implant (i.e., the femoral component 72). Thus, the user is able to plan bone preparation for implanting the second implant on the second bone based at least in part on the first and second points.

In one embodiment, the size and position of the femoral component 72 are determined by mapping a first point at a centerline on an anterior edge of the tibial trial implant with the leg in extension and a second point at the centerline on the anterior edge of the tibial trial implant with the leg in flexion. The extension point is used to size the femoral component 72. For example, the size of the femoral component 72 may be selected so that the tibial component 74 will not ride off an anterior edge of the femoral component 72 as the knee moves into extension. The flexion and extension points together are used to determine the internal/external rotation of the femoral component 72 to ensure that the femoral component 72 properly rides on the tibial component 74 (e.g., based on the patient's natural range of motion and joint kinematics). For example, a centerline of a representation of the second implant (e.g., a representation of the keel 72c of the femoral component 72) may be aligned with the flexion and extension points. Optionally, a point on the posterior "cut" edge may be used to determine the posterior placement of the femoral component 72. In this embodiment, the user selects a location for the femoral component 72 by moving the implant model 808a (shown in FIG. 38) to the general implantation area. Using the transverse view in the frame 806, the user adjusts the implant model 808a rotationally so that a centerline of the implant model 808a aligns with the mapped points 810 representing the centerline of the tibial trial implant in extension and flexion. An internal/external angle dimension (designated "External") in the frame 807 displays the resulting internal/external angle. Using the coronal view in the frame 804, the user adjusts the varus/valgus angle of the implant model 808a. A varus/valgus (designated "Valgus") angle dimension in the frame 807 displays the resulting varus/valgus angle. Using the sagittal view in the frame 802, the user adjusts the posterior rotation of the implant model 808a. A flexion angle dimension (designated "Flexion") in the frame 807 displays the resulting flexion angle. In one embodiment, the posterior rotation is adjusted so that the stem of the femoral component 72 is within a range of approximately 5° to approximately 8° of the anatomical axis of the bone image. The user may adjust a distal depth of the implant model 808a in the femur F by adjusting a depth bar (designated "Depth") in the frame 807. The user may also change the size of the implant model 808a using a size selection box (designated "Size") in the frame 807. In this manner, the representation of the second implant (the implant model 808a) is associated with the representation of the second bone (i.e., the femur F) based at least in part on a detected location of the first implant on the first bone (i.e., the tibia T).

Figure 39:
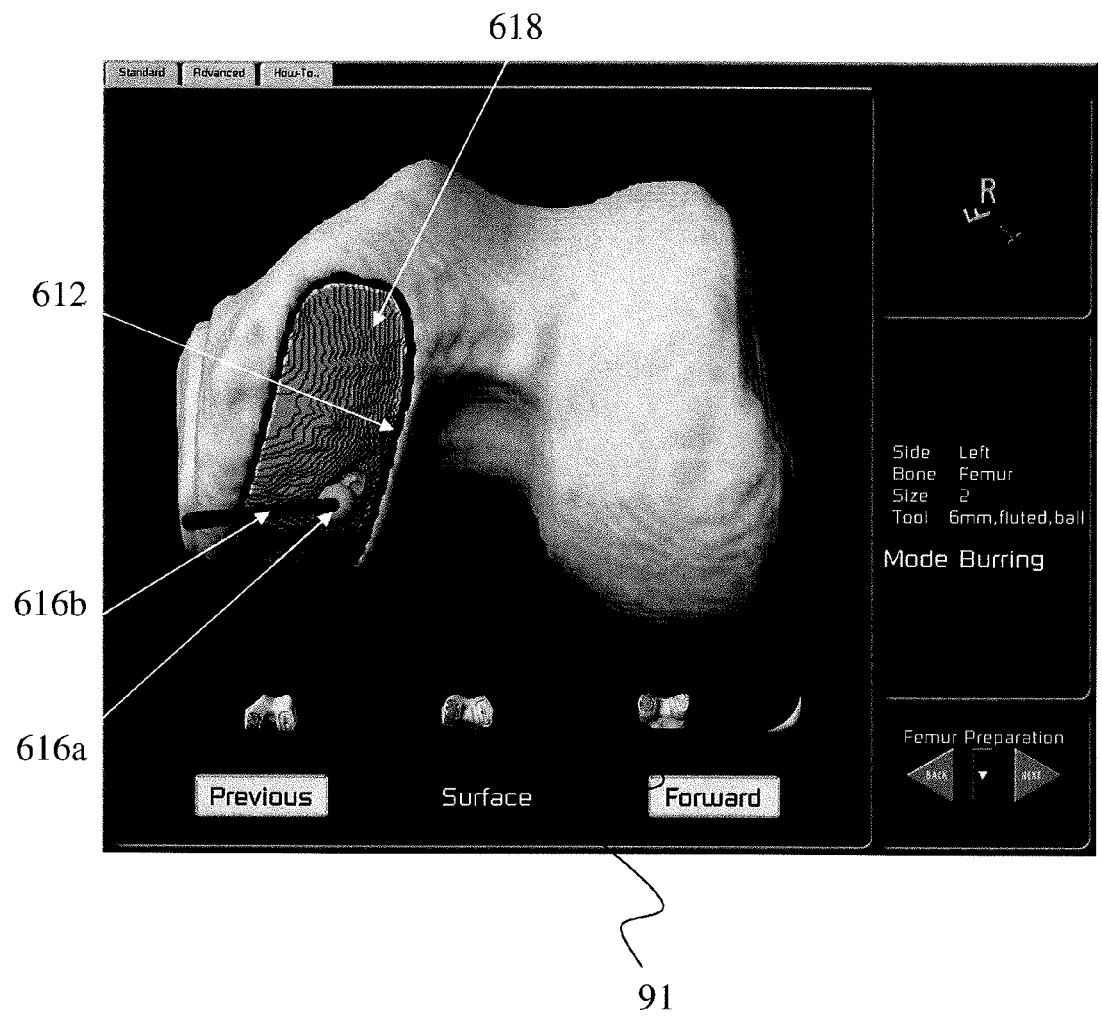
FIG. 39 is a view of an embodiment of a surgical navigation screen showing a bone preparation step according to the present invention.

In step S14, the second bone is prepared to receive the second implant by manipulating the tool 50 to sculpt the second bone. In one embodiment, the femur F is prepared by forming the medial femoral surface, post, and keel features on the distal end of the femur F. Upon installation of the femoral component 72, the medial femoral surface, post, and keel features will mate with a surface 72a, a post 72b, and a keel 72c, respectively, of the femoral component 72 (shown in FIG. 10A). Preparation of the femoral features is substantially similar to the preparation of the medial tibial surface feature. As shown in FIG. 39, the surgical system 10 displays a screen 91 showing a graphical representation of the femur F. As with the screen 89 for tibia preparation, the screen 91 includes the representation 612 of the portion 618 of bone to be removed and a graphical representation of the tool 50 showing the tool tip 616a and a tool shaft 616b. The screen 91 may optionally display a position of the opposite bone (i.e., the tibia T) to guide the user in avoiding accidental cutting of a surface of the opposite bone. As before, the portion 618 of bone to be removed is preferably colored a different color from the surrounding bone. The haptic device 30 enters the approach mode in which a haptic object (e.g., the haptic object 300 in FIG. 1, the haptic object 310 in FIG. 9) in the form of an approach path assists the user in guiding the tip of the tool 50 through the incision 128 and toward the feature of interest on the patient (i.e., the portion of bone on the patient's anatomy corresponding to the portion 618 graphically represented on the screen 91). The surgical system 10 automatically places the haptic device 30 in the haptic (or burring) mode, for example, when the tip of the tool 50 approaches a predefined point related to the feature of interest. When the haptic device 30 is placed in the haptic mode, the surgical system 10 also initiates the occlusion detection algorithm.

Once the haptic device 30 enters the haptic mode, the user may proceed with bone sculpting. As shown in FIG. 39, as the user removes bone with the tool 50, the surgical system 10 updates the image of the femur F on the screen 91 to show a depth to which bone has been removed. During the bone removal process, the haptic device 30 imparts force feedback to the user, for example, based on a haptic object (e.g., a haptic object 208 shown in FIG. 9) having a shape and volume corresponding to the portion 618 of bone to be removed. For the medial femoral surface feature, a boundary of the haptic object may substantially correspond, for example, to the surface 72*a* (shown in FIG. 10A) of the femoral component 72 that will mate with the sculpted surface of the femur F. The force feedback encourages the user to keep the tip of the tool 50 within the boundaries of the haptic object.

During sculpting, the user may desire to change the tool 50. For example, in one embodiment, the user uses a 6 mm burr to form most of the medial femoral surface feature and a 2 mm to sculpt the "corners" (e.g., regions where a vertical wall of the feature transitions to a horizontal bottom of the feature). To replace the burr, the user signals that he wants to withdraw the tool 50. In response, the occlusion detection algorithm is halted and the haptic device 30 is placed in the free mode to enable withdrawal of the tool 50. Once the burr has been replaced, the haptic device 30 may be placed in the approach mode to enable the user to direct the tool 50 to the surgical site to finish forming the medial femoral surface feature. In a preferred embodiment, prior to recommencing sculpting, the user touches the tool 50 (or a tracked probe) to a mark that was placed on the bone (e.g., the femur F or the tibia T) during the initial registration in step S8. The mark functions as a check point that enables the surgical system 10 to verify proper system configuration. For example, the check point can be used to verify that the tracking system 40 is properly configured (e.g., trackers still properly aligned relative to the anatomy, not blocked or occluded, etc.), that that the tool 50 is correctly installed (e.g., property seated, shaft not bent, etc.), and/or that any other object is properly mounted, installed, set up, etc. If the check reveals a problem with the system configuration (e.g., one of the trackers was bumped by the user during the tool change and is now misaligned), registration (step S8) must be repeated. This check point verification may be performed anytime the user desires to validate the system configuration such as when the tool 50 is withdrawn from and then reinserted into the patient. When sculpting of the medial femoral surface feature is complete, the user may signal (e.g., using a foot pedal or other input device 25) that he is ready to proceed to forming the medial femoral post feature. In one embodiment, prior to forming the medial post feature, the user replaces the 2 mm burr used to form the corners of the medial femoral surface feature with a 4 mm burr.

The process for sculpting the medial femoral post feature is substantially similar to the process for sculpting the medial femoral surface feature. As with the femoral surface feature, the surgical system 10 displays the screen 91 (shown in FIG. 39) showing the graphical representation of the femur F, the representation 612 of the portion 618 of bone to be removed, a representation of the tool 50 showing a representation the tool tip 616*a* and a representation of the tool shaft 616*b*, and optionally a representation of the opposite bone (i.e., the tibia T). As before, the portion 618 of bone to be removed is preferably colored a different color from the surrounding bone. In one embodiment, the surgical system 10 displays only the representation of the tip 616*a* of the tool 50 in the screen 91. However, due to the criticality of an approach angle of the tool 50 in forming the post and keel features, the surgical system 10 preferably indicates an allowable angle of inclination of the shaft of the tool 50 when the post and keel features are being sculpted. For example, the representation of the shaft 616*b* may be displayed so that the user is able to see how the shaft 616*b* is oriented with respect to the anatomy. Thus, the user can determine whether the shaft is rubbing against a previously sculpted bone wall (or other object) as the user sculpts deeper portions of the femoral features. A numerical value of a tool angle (e.g., an angle of inclination) may also be shown the screen 91. The surgical system 10 may also include a haptic object shaped so as to constrain an angle of the shaft of the tool 50 to a predetermined value. In one embodiment, the predetermined value is such that the shaft of the tool 50 remains substantially perpendicular to a plane of bone into which the tool 50 is cutting. For example, the predetermined value may be in a range of about 80° to about 90° from the plane of bone into which the tool 50 is cutting. The screen 91 may also include a graphical depiction of the haptic object that constrains the shaft and may change the color of the haptic object (e.g., to red) if the tool angle exceeds the predetermined value. Additionally or alternatively, the tool 50 may include a sleeve disposed about the shaft and/or the tip of the tool 50 that prevents the rotating shaft and/or tip from coming into direct contact with bone.

The haptic device 30 enters the approach mode in which a haptic object (e.g., the haptic object 300 in FIG. 1, the haptic object 310 shown in FIG. 9) in the form of an approach path assists the user in guiding the tip of the tool 50 toward the feature of interest on the patient (i.e., the portion of bone on the patient's anatomy corresponding to the portion 618 graphically represented on the screen 91). The surgical system 10 automatically places the haptic device 30 in the haptic (or burring) mode, for example, when the tip of the tool 50 approaches a predefined point related to the feature of interest. If the occlusion detection algorithm was previously halted (e.g., to withdraw the tool 50 after formation of the femoral surface feature), the surgical system 10 initiates the occlusion detection algorithm when the haptic device 30 enters the haptic mode.

Once the haptic device 30 enters the haptic mode, the user may proceed with bone sculpting. As the user removes bone with the tool 50, the surgical system 10 updates the image of the femur F on the screen 91 to show a depth to which bone has been removed. During the bone removal process, the haptic device 30 imparts force feedback to the user, for example, based on a haptic object having a shape and volume corresponding to the portion 618 of bone to be removed. For the medial femoral post feature, a boundary of the haptic object may substantially correspond, for example, to a surface of the post 72*b* (shown in FIG. 10A) of the femoral component 72 that will mate with the sculpted surface of the femur F. When the medial femoral post feature is complete, the user may signal (e.g., using a foot pedal or other input device 25) that he is ready to proceed to forming the medial femoral keel feature. In one embodiment, prior to forming the keel feature, the user replaces the 4 mm burr with a straight burr. As discussed above in connection with the corners of the medial femoral surface feature, to replace the burr, the user signals that he needs to withdraw the tool 50. In response, the occlusion detection algorithm is halted and the haptic device 30 is placed in the free mode to enable withdrawal of the tool 50. Once the burr has been replaced, the user may proceed with forming the medial femoral keel feature. Preferably, the user performs the above-described check point verification prior to recommencing bone sculpting.

The process for sculpting the medial femoral keel feature is substantially similar to the process for sculpting the medial femoral surface and post features. As with the femoral surface and post features, the surgical system 10 displays the screen 91 (shown in FIG. 39) showing the graphical representation of the femur F, the representation 612 of the portion 618 of bone to be removed, a graphical representation of the tool 50 showing the tool tip 616*a* and a tool shaft 616*b*, and optionally a representation of the opposite bone (i.e., the tibia T). As before, the portion 618 of bone to be removed is preferably colored a different color from the surrounding bone. Additionally, as discussed above in connection with the medial femoral post feature, the screen 91 may include features that enable the user to monitor tool angle to avoid damaging surrounding bone with the rotating shaft of the tool 50.

The haptic device 30 enters the approach mode in which a haptic object (e.g., the haptic object 300 in FIG. 1, the haptic object 310 shown in FIG. 9) in the form of an approach path assists the user in guiding the tip of the tool 50 through the incision 128 and toward the feature of interest on the patient (i.e., the portion of bone on the patient's anatomy corresponding to the portion 618 graphically represented on the screen 91). The surgical system 10 automatically places the haptic device 30 in the haptic (or burring) mode, for example, when the tip of the tool 50 approaches a predefined point related to the feature of interest. When the haptic device 30 enters the haptic mode, the surgical system 10 also initiates the occlusion detection algorithm. Once the haptic device 30 enters the haptic mode, the user may proceed with bone sculpting. As the user removes bone with the tool 50, the surgical system 10 updates the image of the femur F on the screen 91 to show a depth to which bone has been removed. During the bone removal process, the haptic device 30 imparts force feedback to the user, for example, based on a haptic object having a shape and volume corresponding to the portion 618 of bone to be removed. For the medial femoral keel feature, a boundary of the haptic object may substantially correspond, for example, to a surface of the keel 72*c* (shown in FIG. 10A) of the femoral component 72 that will mate with the sculpted surface of the femur F. When the medial femoral keel feature is complete, the user may signal (e.g., using a foot pedal or other input device 25) that he is ready to withdraw the tool 50 from the patient. In response, the surgical system 10 halts the occlusion detection algorithm and places the haptic device 30 in the free mode to enable retraction of the tool 50.

Step S15 is a trial reduction process in which the second implant (i.e., the femoral component 72) or a trial implant (e.g., a femoral trial) is fitted to the prepared medial femoral surface, post, and keel features on the femur F. The user assesses the fit of the femoral component 72 or the femoral trial and may make any desired adjustments, such as, for example, repeating implant planning and/or bone sculpting to achieve an improved fit. In step S15, adjustments may also be made to the tibia T. To facilitate trial reduction, the surgical system 10 may generate a screen (not shown) that graphically represents the tracked movement of the femur F and the tibia T and displays measurements, such as, for example, flexion, varus/valgus, and internal/external rotation angles. Additionally, the femoral and/or tibial trial implants may include intrinsic features (e.g., divots, markings, etc.) that can be touched with a tracked probe after the trial implant is fitted to the bone to enable the surgical system 10 to verify placement of the trial implant. The intrinsic features may also be used to key a position of one implant to another implant (e.g., in the case of a modular implant). When the user is satisfied with the fit of the trial implants, the user may proceed with installation of the femoral component 72 and the tibial component 74 and completion of the surgical procedure.

Thus, embodiments of the present invention provide a haptic guidance system and method that may replace direct visualization in minimally invasive surgery, spare healthy bone in orthopedic joint replacement applications, enable intraoperative adaptability and planning, and produce operative results that are sufficiently predictable, repeatable, and/or accurate regardless of surgical skill level.

Other embodiments of the invention will be apparent to those skilled in the art from consideration of the specification and practice of the invention disclosed herein. It is intended that the specification and examples be considered as exemplary only.

What is claimed is:

1. A method of operating a surgical system comprising:
manually manipulating a surgical instrument;
tracking a position of the surgical instrument and a position of an anatomy of a patient using a detection device, wherein the positions of the surgical instrument and the anatomy are tracked relative to a reference point within a coordinate frame of reference of the detection device;
associating a virtual object with an anatomy of a patient, wherein the virtual object is representative of a cutting boundary;
wherein the surgical instrument and the anatomy move independently of the other and relative to the reference point;
determining, based on the tracked position of the anatomy, that the anatomy has moved relative to the reference point;
maintaining registration between the anatomy and the virtual object when the anatomy has moved relative to the reference point by automatically adjusting the cutting boundary relative to the reference point in response to the determined movement of the anatomy;
providing haptic feedback to a user manually manipulating the surgical instrument to constrain the surgical instrument from penetrating the adjusted cutting boundary; and
providing visual information to the user, wherein the visual information comprises a representation of a desired portion of material to be removed by the surgical instrument in a first color that is updated to represent a portion of the desired material actually removed by the surgical instrument in a second color, based on the tracked position of the surgical instrument, and wherein the visual information further comprises a representation of a portion of material actually removed that exceeds the desired portion of material to be removed in a third color.

2. The method of claim 1, wherein the surgical instrument is a cutting tool.

3. The method of claim 2, wherein the cutting boundary defines a cutting surface relative to the anatomy.

4. The method of claim 1, wherein the haptic feedback is provided based on a relationship between the anatomy and at least one of a position, an orientation, a velocity and an acceleration of at least a portion of the surgical instrument.

5. The method of claim 1, wherein the step of associating a virtual object with the anatomy includes:
creating a virtual representation of the anatomy;
registering the virtual representation of the anatomy to the anatomy; and
associating the virtual object with the virtual representation of the anatomy.

6. The method of claim 1, wherein the step of associating the virtual object with the anatomy of the patient includes associating the virtual object with a bone of the patient.

7. The method of claim 6, wherein the bone is a femur.

8. The method of claim 6, wherein the bone is a tibia.

9. The method of claim 1, wherein at least a portion of the cutting boundary includes material to be removed from the anatomy.

10. The method of claim 1, wherein the step of providing haptic feedback to the user includes controlling an actuator of the surgical system.

11. A method of operating a surgical system, comprising:
manually manipulating a surgical instrument;
tracking a position of the surgical instrument and a position of an anatomy of a patient using a detection device, wherein the positions of the surgical instrument and the anatomy are tracked relative to a reference point within a coordinate frame of reference of the detection device;
wherein the surgical instrument and the anatomy move independently of the other and relative to the reference point;
creating a virtual representation of the anatomy;
registering the virtual representation of the anatomy to the anatomy;
associating a virtual object with the virtual representation of the anatomy, the virtual object being representative of a cutting boundary;
creating a representation of the virtual object, representing a desired portion of material to be removed from the anatomy in a first color;
updating the representation of the desired portion of material to be removed with a representation of a portion of the material actually removed by the tool in a second color, based on the tracked position of the surgical instrument;
updating the representation of the virtual object, representing a portion of material actually removed that exceeds the desired portion of material to be removed in a third color;
determining, based on the tracked position of the anatomy, that the anatomy has moved relative to the reference point;
maintaining registration between the anatomy and the virtual object when the anatomy has moved relative to the reference point by automatically adjusting the cutting boundary relative to the reference point in response to the determined movement of the anatomy; and
controlling the surgical system to provide haptic feedback to a user manually manipulating the surgical instrument to constrain the surgical instrument from penetrating the adjusted cutting boundary.

12. The method of claim 11, wherein the surgical instrument is a cutting tool and the cutting boundary defines a cutting surface relative to the anatomy.

13. The method of claim 11, wherein the step of controlling the surgical instrument includes providing haptic feedback to a user.

14. The method of claim 13, wherein the haptic feedback is provided based on a relationship between the anatomy and at least one of a position, an orientation, a velocity and an acceleration of at least a portion of the surgical instrument.

15. The method of claim 11, wherein the step of associating the virtual object with the anatomy of the patient includes associating the virtual object with a bone of the patient.

16. The method of claim 15, wherein the bone is a femur.

17. The method of claim 15, wherein the bone is a tibia.

18. The method of claim 11, wherein the step of controlling the surgical system to constrain the surgical instrument includes controlling an actuator of the surgical system.

19. A surgical apparatus comprising:
a surgical instrument configured to be manually manipulated by a user to perform a procedure on a patient; and
a computer system programmed:
to track a position of the surgical instrument and a position of an anatomy of a patient using a detection device, wherein the positions of the surgical instrument and the anatomy are tracked relative to a reference point within a coordinate frame of reference of the detection device;
to associate a virtual object with an anatomy of the patient, wherein the virtual object is representative of a cutting boundary;
wherein the computer system is programmed to track the surgical instrument and the anatomy that move independently of the other and relative to the reference point;
to determine, based on the tracked position of the anatomy, that the anatomy has moved relative to the reference point;
to maintain registration between the anatomy and the virtual object when the anatomy has moved relative to the reference point by automatically adjusting the cutting boundary relative to the reference point in response to the determined movement of the anatomy;
to provide haptic feedback to a user manually manipulating the surgical instrument to constrain the tool from penetrating the adjusted cutting boundary; and
to provide visual information to the user, wherein the visual information comprises a representation of a desired portion of material to be removed by the surgical instrument in a first color that is updated to represent a portion of the desired material actually removed by the surgical instrument in a second color, based on the tracked position of the surgical instrument, and wherein the visual information further comprises a representation of a portion of material actually removed that exceeds the desired portion of material to be removed in a third color.

20. The apparatus of claim 19, wherein the haptic feedback is provided based on a relationship between the anatomy and at least one of a position, an orientation, a velocity and an acceleration of at least a portion of the surgical instrument.

21. The apparatus of claim 19, wherein the computer system is programmed to provide haptic feedback to the user by controlling an actuator of the surgical apparatus.

* * * * *